(12) United States Patent
Kiso

(10) Patent No.: US 7,312,188 B2
(45) Date of Patent: Dec. 25, 2007

(54) PEPTIDE DERIVATIVES HAVING β-SECRETASE INHIBITORY ACTIVITY

(76) Inventor: Yoshiaki Kiso, 15-26, Inaba-cho, Ibaraki-shi, Osaka-fu (JP)

( * ) Notice: Subject to any disclaimer, the term of this patent is extended or adjusted under 35 U.S.C. 154(b) by 49 days.

(21) Appl. No.: 10/546,914

(22) PCT Filed: Feb. 27, 2004

(86) PCT No.: PCT/JP2004/002438

§ 371 (c)(1),
(2), (4) Date: Aug. 25, 2005

(87) PCT Pub. No.: WO2004/076478

PCT Pub. Date: Sep. 10, 2004

(65) Prior Publication Data

US 2007/0004637 A1    Jan. 4, 2007

(30) Foreign Application Priority Data

Feb. 28, 2003   (JP) .............................. 2003-052926

(51) Int. Cl.
*A61K 38/00* (2006.01)
*A61K 38/03* (2006.01)
(52) U.S. Cl. .................... 514/2; 424/185.1; 424/193.1; 530/300
(58) Field of Classification Search ...................... None
See application file for complete search history.

(56) References Cited

U.S. PATENT DOCUMENTS

| 4,666,887 A * | 5/1987 | De Barbieri ................. 514/18 |
| 6,187,905 B1 | 2/2001 | Hurst et al. |
| 2002/0115616 A1 | 8/2002 | Boyd et al. |
| 2003/0130484 A1* | 7/2003 | Gordon et al. ............. 530/350 |

FOREIGN PATENT DOCUMENTS

| JP | 02-101098 | 4/1990 |
| JP | 11-349597 | 12/1999 |
| JP | 2003-502342 | 1/2001 |
| JP | 2002-322198 | 11/2002 |
| WO | 00/77030 | 12/2000 |

OTHER PUBLICATIONS

Parkinson's Disease in Merck manual.*
Dementia in Merck manual.*
Mattson MP, Pathways towrads and away from Alzheimer's disease.*
J. Marcinkeviciene et al., "Mechanism of Inhibition of β-Site Amiloid Precursor Protein-Cleaving Enzyme (BACE), by a Statine-Based Peptide", J. Biol. Chem., vol. 276, No. 26, pp. 23790-23794, 2001.
Y. Hayashi et al., "An Approach for Peptidic Aspartic Protease Inhibitors using Ala-containing Oligopeptides Independent of the Substrate Sequence", Peptide Science, No. 39, pp. 295-296, Mar. 2003.
D. Shuto et al., "KMI-008, A Novel β-Secretase Inhibitor Containing a Hydroxymethyl Carbonyl Isostere as a Transition-State Mimic: Design and Synthesis of Substrate-Based Octapeptides", Bioorganic & Medical Chemistry Letters, vol. 13, pp. 4273-4276, 2003.
J. Marcinkeviciene et al., "Mechanism of Inhibition of β-Site Amiloid Precursor Protein-Cleaving Enzyme (BACE), by a Statine-Based Peptide", J. Biol. Chem., vol. 276, No. 26, pp. 23790-23794, 2001.
Y. Hayashi et al., "An Approach for Peptidic Aspartic Protease Inhibitors using Ala-containing Oligopeptides Independent of the Substrate Sequence", Peptide Science, No. 39, pp. 295-296, Mar. 2003.
D. Shuto et al., "KMI-008, A Novel β-Secretase Inhibitor Containing a Hydroxymethyl Carbonyl Isostere as a Transition-State Mimic: Design and Synthesis of Substrate-Based Octapeptides", Bioorganic & Medical Chemistry Letters, pp. 4273-4276, Dec. 13, 2003.

* cited by examiner

*Primary Examiner*—Anish Gupta
*Assistant Examiner*—Julie Ha
(74) *Attorney, Agent, or Firm*—Wenderoth, Lind & Ponack, L.L.P.

(57) ABSTRACT

Provided are excellent β-secretase inhibitors, that is, compounds represented by the general formula (1) or prodrugs thereof:

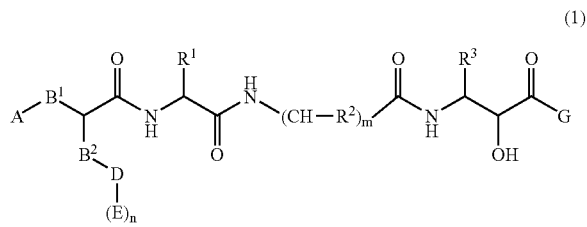

wherein A is amino or protected amino; $B^1$ and $B^2$ are each a single bond, alkylene of 1 to 3 carbon atoms, or the like; D is a single bond, —NHCO, or the like; E is —COOH, tetrazole ring, or the like; n is an integer of 1 to 3; m is an integer of 1 to 3; G is hydroxyl, a group represented by the general formula (2), or the like:

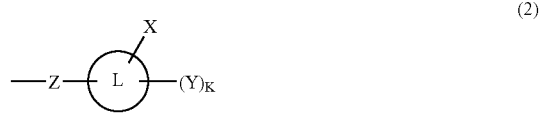

in which Z is —NH, -Asp-Ala-NH—, -Asp-Ala-, -Asp-NH—, or the like; L is a 5- to 10-membered ring optionally containing a heteroatom and/or unsaturated bond; X is —COOH, tetrazole ring, or the like; Y is hydrogen, —COOH, or the like; and k is an integer of 1 to 4; and $R^1$, $R^2$, and $R^3$ are each alkyl of 1 to 6 carbon atoms, or the like.

10 Claims, No Drawings

SEQUENCE LISTING

<160> NUMBER OF SEQ ID NOS: 95

<210> SEQ ID NO 1
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-5-
      methylhexanoic acid

<400> SEQUENCE: 1

Glu Val Asn Xaa Asp Ala Glu Phe
1               5

<210> SEQ ID NO 2
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 2

Glu Val Asn Xaa Asp Ala Glu Phe
1               5

<210> SEQ ID NO 3
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 3

Glu Val Asp Xaa Asp Ala Glu Phe
1               5

<210> SEQ ID NO 4
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 4

Glu Val Gln Xaa Asp Ala Glu Phe
1               5

<210> SEQ ID NO 5
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 5

Glu Val Glu Xaa Asp Ala Glu Phe
1               5

<210> SEQ ID NO 6
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 6

Glu Val Met Xaa Asp Ala Glu Phe
1               5

```
<210> SEQ ID NO 7
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 7

Glu Val Leu Xaa Asp Ala Glu Phe
1               5

<210> SEQ ID NO 8
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 8

Glu Val Lys Xaa Asp Ala Glu Phe
1               5

<210> SEQ ID NO 9
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 9

Glu Leu Leu Xaa Asp Ala Glu Phe
1               5

<210> SEQ ID NO 10
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 10

Glu Ile Leu Xaa Asp Ala Glu Phe
1               5

<210> SEQ ID NO 11
<211> LENGTH: 8
<212> TYPE: PRT
<213> ORGANISM: Artificial
<220> FEATURE:
<223> OTHER INFORMATION: Synthetic Construct
<220> FEATURE:
```

<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 11

Glu Phe Leu Xaa Asp Ala Glu Phe
1               5

<210> SEQ ID NO 12
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 12

Glu Met Leu Xaa Asp Ala Glu Phe
1               5

<210> SEQ ID NO 13
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 13

Glu Val Leu Xaa Ala Ala Glu Phe
1               5

<210> SEQ ID NO 14
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 14

Glu Val Leu Xaa Asn Ala Glu Phe
1               5

<210> SEQ ID NO 15
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 15

-continued

```
Glu Val Leu Xaa Glu Ala Glu Phe
1               5
```

<210> SEQ ID NO 16
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 16

```
Glu Val Leu Xaa Gln Ala Glu Phe
1               5
```

<210> SEQ ID NO 17
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (5)..(5)
<223> OTHER INFORMATION: Xaa is (S)-5,5-dimethyl-1,3-thiazolidine-4-
      carboxylic acid

<400> SEQUENCE: 17

```
Glu Val Leu Xaa Xaa Ala Glu Phe
1               5
```

<210> SEQ ID NO 18
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 18

```
Glu Val Leu Xaa Asp Ala Glu Phe
1               5
```

<210> SEQ ID NO 19
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 19

```
Glu Val Leu Xaa Ala Ala Glu Phe
1               5
```

```
<210> SEQ ID NO 20
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 20

Glu Val Leu Xaa Asn Ala Glu Phe
1               5

<210> SEQ ID NO 21
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 21

Glu Val Leu Xaa Glu Ala Glu Phe
1               5

<210> SEQ ID NO 22
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 22

Glu Val Leu Xaa Gln Ala Glu Phe
1               5

<210> SEQ ID NO 23
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (5)..(5)
<223> OTHER INFORMATION: Xaa is (R)-5,5-dimethyl-1,3-thiazolidine-4-
      carboxylic acid

<400> SEQUENCE: 23

Glu Val Leu Xaa Xaa Ala Glu Phe
1               5
```

```
<210> SEQ ID NO 24
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 24

Glu Val Leu Xaa Ala Val Glu Phe
1               5

<210> SEQ ID NO 25
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 25

Glu Val Leu Xaa Ala Leu Glu Phe
1               5

<210> SEQ ID NO 26
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 26

Glu Val Leu Xaa Ala Phe Glu Phe
1               5

<210> SEQ ID NO 27
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 27

Glu Val Leu Xaa Ala Glu Glu Phe
1               5

<210> SEQ ID NO 28
<211> LENGTH: 8
<212> TYPE: PRT
<213> ORGANISM: Artificial
<220> FEATURE:
<223> OTHER INFORMATION: Synthetic Construct
<220> FEATURE:
```

```
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 28

Glu Val Leu Xaa Asp Ala Gln Phe
1               5

<210> SEQ ID NO 29
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 29

Glu Val Leu Xaa Asp Ala Val Phe
1               5

<210> SEQ ID NO 30
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 30

Glu Val Leu Xaa Asp Ala Leu Phe
1               5

<210> SEQ ID NO 31
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 31

Glu Val Leu Xaa Asp Ala Phe Phe
1               5

<210> SEQ ID NO 32
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 32
```

Glu Val Leu Xaa Asp Ala Glu
1               5

<210> SEQ ID NO 33
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 33

Glu Val Leu Xaa Asp Ala
1               5

<210> SEQ ID NO 34
<211> LENGTH: 5
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 34

Glu Val Leu Xaa Asp
1               5

<210> SEQ ID NO 35
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 35

Val Leu Xaa Asp Ala Glu Phe
1               5

<210> SEQ ID NO 36
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is (2R,3S)-3-amino-2-hydroxy-4-
      phenylbutanoic acid

<400> SEQUENCE: 36

Leu Xaa Asp Ala Glu Phe
1               5

<210> SEQ ID NO 37
<211> LENGTH: 5
<212> TYPE: PRT

```
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is (2R,3S)-3-amino-2-hydroxy-4-
      phenylbutanoic acid

<400> SEQUENCE: 37

Xaa Asp Ala Glu Phe
1               5

<210> SEQ ID NO 38
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 38

Gly Val Leu Xaa Asp Ala Glu Phe
1               5

<210> SEQ ID NO 39
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 39

Glu Gly Leu Xaa Asp Ala Glu Phe
1               5

<210> SEQ ID NO 40
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 40

Glu Val Gly Xaa Asp Ala Glu Phe
1               5

<210> SEQ ID NO 41
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
``` phenylbutanoic acid

<400> SEQUENCE: 41

Glu Val Leu Xaa Gly Ala Glu Phe
1               5

<210> SEQ ID NO 42
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 42

Glu Val Leu Xaa Gly Ala Glu Phe
1               5

<210> SEQ ID NO 43
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 43

Glu Val Leu Xaa Asp Ala Gly Phe
1               5

<210> SEQ ID NO 44
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 44

Glu Val Leu Xaa Asp Ala Glu Gly
1               5

<210> SEQ ID NO 45
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is glt Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 45

```
Xaa Leu Xaa Asp Ala Gly Phe
1               5

<210> SEQ ID NO 46
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 46

Gln Val Leu Xaa Asp Ala Gly Phe
1               5

<210> SEQ ID NO 47
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 47

Asp Val Leu Xaa Asp Ala Gly Phe
1               5

<210> SEQ ID NO 48
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is homo Glu
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 48

Xaa Val Leu Xaa Asp Ala Gly Phe
1               5

<210> SEQ ID NO 49
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is (7-methoxycoumarin-4-yl)acetyl Ser
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid
```

```
<400> SEQUENCE: 49

Xaa Leu Xaa Asp Ala Gly Phe
1               5

<210> SEQ ID NO 50
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is (7-methoxycoumarin-4-yl)acetyl Ser
<220> FEATURE:
<221> NAME/KEY: MISC_FEATURE
<222> LOCATION: (12)..(12)
<223> OTHER INFORMATION: Xaa is (2,4-dinitrophenyl) Arg

<400> SEQUENCE: 50

Xaa Glu Val Asn Leu Asp Ala Glu Phe Arg Lys Xaa Arg
1               5                   10

<210> SEQ ID NO 51
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is beta-(tetrazole-5-carbonyl)-Dap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 51

Xaa Leu Xaa Asp Ala Glu
1               5

<210> SEQ ID NO 52
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is beta-(3,5-dicarboxybenzoyl)-Dap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 52

Xaa Leu Xaa Asp Ala Glu
1               5

<210> SEQ ID NO 53
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
```

```
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 4-aminobenzoic acid

<400> SEQUENCE: 53

Glu Val Leu Xaa Asp Xaa
1               5

<210> SEQ ID NO 54
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 2-aminobenzoic acid

<400> SEQUENCE: 54

Glu Val Leu Xaa Asp Xaa
1               5

<210> SEQ ID NO 55
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 3-aminobenzoic acid

<400> SEQUENCE: 55

Glu Val Leu Xaa Asp Xaa
1               5

<210> SEQ ID NO 56
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 56

Glu Val Leu Xaa Asp Phe Glu Phe
1               5

<210> SEQ ID NO 57
<211> LENGTH: 6
<212> TYPE: PRT
```

```
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is beta-(4-carboxybenzoyl)-Dap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 57

Xaa Leu Xaa Asp Ala Glu
1               5

<210> SEQ ID NO 58
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 58

Glu Val Leu Xaa Asp Ala Glu Phe
1               5

<210> SEQ ID NO 59
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is beta-(3-carboxybenzoyl)-Dap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 59

Xaa Leu Xaa Asp Ala Glu
1               5

<210> SEQ ID NO 60
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is alpha-ODap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 60

Xaa Leu Xaa Asp Ala Glu
1               5
```

```
<210> SEQ ID NO 61
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is tert-Leu

<400> SEQUENCE: 61

Glu Val Leu Xaa Asp Xaa Glu Phe
1               5

<210> SEQ ID NO 62
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 2-aminobenzoic acid

<400> SEQUENCE: 62

Glu Val Leu Xaa Asp Ala Xaa
1               5

<210> SEQ ID NO 63
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 2-piperidinecarboxylic acid

<400> SEQUENCE: 63

Glu Val Leu Xaa Asp Xaa
1               5

<210> SEQ ID NO 64
<211> LENGTH: 5
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
```

```
<400> SEQUENCE: 64

Glu Val Leu Xaa Asp
1               5

<210> SEQ ID NO 65
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 2-aminoisobutyric acid

<400> SEQUENCE: 65

Glu Val Leu Xaa Asp Xaa Glu
1               5

<210> SEQ ID NO 66
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 3-aminobenzoic acid

<400> SEQUENCE: 66

Glu Val Leu Xaa Asp Ala Xaa
1               5

<210> SEQ ID NO 67
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 4-aminobenzoic acid

<400> SEQUENCE: 67

Glu Val Leu Xaa Asp Ala Xaa
1               5

<210> SEQ ID NO 68
<211> LENGTH: 7
<212> TYPE: PRT
<213> ORGANISM: Artificial
<220> FEATURE:
<223> OTHER INFORMATION: Synthetic Construct
```

```
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 2-piperidinecarboxylic acid

<400> SEQUENCE: 68

Glu Val Leu Xaa Asp Ala Xaa
1               5

<210> SEQ ID NO 69
<211> LENGTH: 6
<212> TYPE: PRT
<213> ORGANISM: Artificial
<220> FEATURE:
<223> OTHER INFORMATION: Synthetic Construction
<220> FEATURE:
<221> NAME/KEY: MISC_FEATURE
<222> LOCATION: (1)..(1)
<223> OTHER INFORMATION: Xaa is beta-ethoxyoxalyl-Dap Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 69

Xaa Leu Xaa Asp Ala Glu
1               5

<210> SEQ ID NO 70
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 70

Glu Val Leu Xaa Val Ala Glu Phe
1               5

<210> SEQ ID NO 71
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-5-
      methylhexanoic acid

<400> SEQUENCE: 71

Glu Val Leu Xaa Asp Ala Glu Phe
1               5

<210> SEQ ID NO 72
<211> LENGTH: 7
<212> TYPE: PRT
<213> ORGANISM: Artificial
<220> FEATURE:
```

```
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 72

Glu Val Leu Xaa Asp Ala Glu
1               5

<210> SEQ ID NO 73
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is (S)-2-amino-3-(4-thiazole)propanoic acid
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 73

Glu Val Xaa Xaa Asp Ala Glu Phe
1               5

<210> SEQ ID NO 74
<211> LENGTH: 5
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 74

Glu Val Leu Xaa Asp
1               5

<210> SEQ ID NO 75
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is 5-oxalyl-(s)-2,5-diaminopentanoic acid
      Val
<220> FEATURE:
<221> NAME/KEY: MISC_FEATURE
<222> LOCATION: (3)..(3)
<223> OTHER INFORMATION: Xaa is (2R,3S)-3-amino-2-hydroxy-4-
      phenylbutanoic acid

<400> SEQUENCE: 75

Xaa Leu Xaa Asp Ala Glu
1               5

<210> SEQ ID NO 76
<211> LENGTH: 6
<212> TYPE: PRT
```

```
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (6)..(6)
<223> OTHER INFORMATION: Xaa is 4-aminomethylbenzoic acid

<400> SEQUENCE: 76

Glu Val Leu Xaa Asp Xaa
1               5

<210> SEQ ID NO 77
<211> LENGTH: 5
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-5-
      methylhexanoic acid

<400> SEQUENCE: 77

Glu Val Leu Xaa Asp
1               5

<210> SEQ ID NO 78
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (5)..(5)
<223> OTHER INFORMATION: Xaa is (r)-5,5-dimethyl-1,3-thiazolidine-4-
      carboxylic acid

<400> SEQUENCE: 78

Glu Val Leu Xaa Xaa Ala Glu Phe
1               5

<210> SEQ ID NO 79
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 79

Glu Val Leu Xaa Leu Ala Glu Phe
1               5

<210> SEQ ID NO 80
```

```
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 4-aminomethylbenzoic acid

<400> SEQUENCE: 80

Glu Val Leu Xaa Asp Ala Xaa
1               5

<210> SEQ ID NO 81
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 3-piperidinecarboxylic acid

<400> SEQUENCE: 81

Glu Val Leu Xaa Asp Ala Xaa
1               5

<210> SEQ ID NO 82
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 4-piperidinecarboxylic acid

<400> SEQUENCE: 82

Glu Val Leu Xaa Asp Ala Xaa
1               5

<210> SEQ ID NO 83
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-5-
      methylhexanoic acid

<400> SEQUENCE: 83
```

-continued

```
Glu Val Leu Xaa Asp Ala Glu Phe
1               5
```

<210> SEQ ID NO 84
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 4-aminocycloheanecarboxylic acid

<400> SEQUENCE: 84

```
Glu Val Leu Xaa Asp Ala Xaa
1               5
```

<210> SEQ ID NO 85
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 85

```
Glu Val Leu Xaa Asp Ala Glu
1               5
```

<210> SEQ ID NO 86
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 86

```
Glu Ala Leu Xaa Asp Ala Glu Phe
1               5
```

<210> SEQ ID NO 87
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 87

```
Glu Val Leu Xaa Asp Ala Arg
1               5
```

```
<210> SEQ ID NO 88
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 88

Glu Val Leu Xaa Pro Ala Glu Phe
1               5

<210> SEQ ID NO 89
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is (2S)-2-amino-2-(3-tetrhydrofuranyl)
      acetic acid
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 89

Glu Val Xaa Xaa Asp Ala Glu Phe
1               5

<210> SEQ ID NO 90
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 90

Glu Val Leu Xaa Asp Ala
1               5

<210> SEQ ID NO 91
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (7)..(7)
<223> OTHER INFORMATION: Xaa is 4-aminobutanoic acid

<400> SEQUENCE: 91

Glu Val Leu Xaa Asp Ala Xaa
```

```
1               5
```

<210> SEQ ID NO 92
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid
<220> FEATURE:
<221> NAME/KEY: MISC_FEATURE
<222> LOCATION: (5)..(5)
<223> OTHER INFORMATION: Xaa is (R)-1,3,-thiazolidine-4-carboxylic acid

<400> SEQUENCE: 92

```
Glu Val Leu Xaa Xaa Ala Glu Phe
1               5
```

<210> SEQ ID NO 93
<211> LENGTH: 5
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 93

```
Glu Val Leu Xaa Asp
1               5
```

<210> SEQ ID NO 94
<211> LENGTH: 8
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is (2R,3S)-3-amino-2-hydroxy-4-
      phenylbutanoic acid

<400> SEQUENCE: 94

```
Glu Val Val Xaa Asp Ala Glu Phe
1               5
```

<210> SEQ ID NO 95
<211> LENGTH: 6
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is beta-(3,4-dihydroxybenzoyl)Dap Val
<220> FEATURE:
<221> NAME/KEY: MISC_FEATURE
<222> LOCATION: (3)..(3)

```
<223> OTHER INFORMATION: Xaa is (2R,3S)-3-amino-2-hydroxy-4-
      phenylbutanoic acid

<400> SEQUENCE: 95

Xaa Val Xaa Asp Ala Glu
1               5
```

PEPTIDE DERIVATIVES HAVING β-SECRETASE INHIBITORY ACTIVITY

This application is a U.S. national stage of International Application No. PCT/JP2004/002438 filed Feb. 27, 2004.

TECHNICAL FIELD

The present invention relates to a peptide derivative having excellent β-secretase inhibitory activity.

BACKGROUND ART

Alzheimer's disease (abbreviated as AD) is a neurodegenerative disease characterized by dementia. Ad insidiously develops in old age and gradually progresses to dementia. AD is pathologically characterized by large amount of senile plaques and neurofibrillary tangles (abbreviated as NFT) observed in the cerebral cortex and hippocampus, and by cerebral atrophy due to deciduation of neuron.

Senile plaque has, as a main component, an amyloid fiber comprising of an extracellularly sedimented amyloid β-peptide (abbreviated as Aβ). The appearance of AB is extremely specific for AD and aging. Senile plaque is a pathological change which is seen at the earliest stage of the disease's progression. Therefore, an understanding of the mechanism of formation and sedimentation of Aβ has a very important significance in elaborating the morbid state of AD.

Aβ includes, two main molecular species; Aβ 40 that ends at the 40$^{th}$ amino acid residue Val; and Aβ 42 which is larger by two residues (Ile, Ala). Among the Aβ secreted from cells, about 90% is Aβ 40, and 10% is Aβ 42. However, Aβ 42 exhibits aggregating property which is far greater than that of Aβ 40. Aggregated Aβ 42 entangles with Aβ 40 to form amyloids. In addition, because Aβ 40 accumulated during the initial stage of plaque formation, it has been suggested that the accumulation of Aβ 40 was strongly associated with the development of AD.

Aβ is produced by cleavage of an amyloid precursor protein (abbreviated as APP) by two kinds of proteases. APP is a type I transmembrane protein consisting of about 700 residues, with Aβ contained in its extracellular region at a transmembrane region. A protease that is involved in the production of Aβ from APP is called "secretase". A secretase that cuts (cleaves) the amino terminal of Aβ is a "β secretase"; a secretase that cuts the carboxyl terminal is a "γ secretase"; and a secretase that cuts the carboxyl terminal of the 16$^{th}$ Lys in the interior of Aβ is an "α secretase". In an amyloidogenic pathway, APP is cut with a β secretase to produce a secretion-type APP β (sAPP β) and a carboxyl terminal fragment called β-stub. A γ secretase cuts this fragment to produce Aβ and a γ-stub. In a non-amyloidogenic pathway, an α secretase cuts APP to produce secretion-type APPα (sAPPα) and a carboxyl terminal fragment called α-stub. A γ secretase cuts this fragment to produce p3 and γ-stub. These two pathways both exist in the normal state. The majority of Aβ that is produced as a physiological molecule is secreted extracellularly.

One of the current mainstream strategies is to target secretase as a point of action for preventing or treating AD. Among them, particular attentions are paid for β and γ secretases since direct effects can be readily observed. In recent years, pharmaceutical enterprises and venture companies vigorously progress in the development of secretase inhibitors.

In 1999, it has been reported by some laboratories that β secretase is a β-site APP cleaving enzyme called BACE1 (also referred to as BACE, Asp2, or memapsin2).

Since BACE1 is an aspartic acid protease, based on the substrate transition state concept established by the study on the same class of protease inhibitor such as renin and HIV, various β secretase inhibitors have been reported in recent years. Swedish variant-type APP readily produces Aβ. A peptide-based inhibitor mimics Swedish APP by forming a substrate transition state analogue at a β secretage cleaving site. Tung et al. determined the IC$_{50}$ value of 30 nM in a 14 residue peptide (P10-P4' statV) in which a hydroxyethylcarbonylisostere (statine) structure was introduced into a substrate cleaving site of β secretase. They reported that other substrate transition state analogues (AHPPA, ACHPA) can also inhibit β secretase (for example, see Nature, 402, 537-540 (1999), J. Med. Chem., 45, 259-262 (2002)). Ghosh et al. searched various compounds containing hydroxyethyleneisostere, and discovered that OM 99-2 had strong inhibitory activity (Ki=1.6 nM) (for example, see WO 01/00665, J. Am. Chem. Soc. 122, 3522-3523 (2000). Based on X-ray crystal structural analysis of an enzyme-OM99-2 complex (for example, see Science 290, 150-153 (2000)), they synthesized derivatives, and found a smaller inhibitor having equipotent activity (for example, see J. Med. Chem., 44, 2865-2868 (2001)).

However, in considering an acting site of a β-secretase inhibitor, a drug needs to pass through the blood-brain barrier. There are many points to be considered such as a molecular size and hydrophilic/hydrophobic balance. In addition, since substrate specificity greatly differs from previous aspartic acid proteases (for example, see Biochemistry, 40, 10001-10006 (2001)), it is expected that the design of inhibitors is very difficult. Furthermore, in order to be physiologically active, it is necessary for the inhibitor to be able to pass through the blood-brain barrier. For this reason, compounds in which the molecular weight is relatively small, and stability in blood is excellent are desired. Designing compounds with such features are thought to be difficult.

DISCLOSURE OF THE INVENTION

The development of a compound that has excellent β-secretase inhibitory activity and is satisfactory as a medicament is solicited.

The present inventors synthesized an octapeptide in which an HMC isostere was introduced into a β-secretase cleaving site of Sweden variant APP, and optimized each site of the octapeptide. Thereafter, they examined the minimum molecular size at which BACE1 inhibitory activity could be maintained, studied correlations between structure and activity, and derived the present compound that had excellent activity. Thus the present invention was completed.

BEST MODE FOR CARRYING OUT THE INVENTION

That is, the present invention relates to a compound represented by the general formula (1):

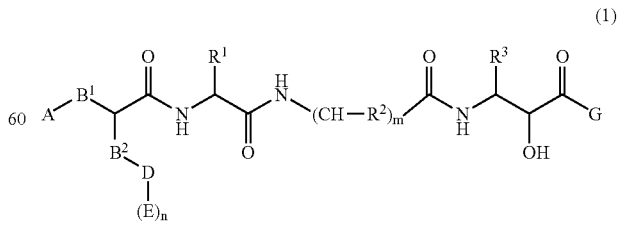

wherein A is amino group or amino group protected with a protecting group which can be degraded in a living body, $B^1$ and $B^2$ are each a single bond or optionally substituted alkylene of 1 to 3 carbon atoms optically substituted with $R^4$, in which $R^4$ is halogen atom; alkyl of 1 to 6 carbon atoms; alkenyl of 2 to 6 carbon atoms; alkynyl of 2 to 6 carbon atoms; cycloalkyl of 3 to 7 carbon atoms; optionally substituted heterocycle; optionally substituted aralkyl; or optionally substituted aryl, and the substituent thereof is alkyl of 1 to 6 carbon atoms, alkenyl of 2 to 6 carbon atoms, alkynyl of 2 to 6 carbon atoms, cycloalkyl of 3 to 7 carbon atoms, or aryl, D is a single bond, —NHCO— or NHCO—$R^5$—, in which $R^5$ is alkylene of 1 to 6 carbon atoms; alkenylene of 2 to 6 carbon atoms; alkynylene of 2 to 6 carbon atoms; cycloalkylene of 3 to 7 carbon atoms; optionally substituted heterocycle; optionally substituted aralkylene; or optionally substituted arylene, and the substituent thereof is halogen atom, alkyl of 1 to 6 carbon atoms, alkenyl of 2 to 6 carbon atoms, alkynyl of 2 to 6 carbon atoms, cycloalkyl of 3 to 7 carbon atoms, or aryl, E is —COOH, a group equivalent to COOH, hydrogen atom, hydroxyl group, amino group, halogen atom, or —COOCH$_3$, n is an integer of 1 to 3, m is an integer of 1 to 3, G is hydroxyl group, amino acid residue, a peptide constituted of 4 to 2 amino acids, or a group of the formula:

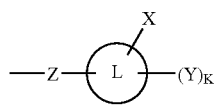

in which Z is —NH—, -Asp-Ala-NH—, -Asp-Ala-, —NH-CZ$^1$(Z$^2$)-, -Asp-NH—, -Asp-NH-CZ$^1$(Z$^2$)-, or —NH-CZ$^1$(Z$^2$)-CZ$^1$(Z$^2$)-, Ring L is a 5- to 10-membered ring optionally containing a heteroatom and/or unsaturated bond;

$Z^1$ and $Z^2$ are each hydrogen atom, hydroxyl group, amino group, cyano group, nitro group, alkyl of 1 to 6 carbon atoms, or halogen atom, X is hydrogen atom, —COOH, a group equivalent to COOH, —CONHR$^6$, —OCH$_2$COOR$^6$, —OCH$_2$CONHR$^6$, hydroxyl group, —PO$_4$H, —SO$_3$H, -CZ$^1$(Z$^2$)-X', or a group of the formula:

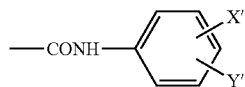

in which X' is hydrogen atom, —COOH, a group equivalent to COOH, —CONHR$^6$, —OCH$_2$COOR$^6$, —OCH$_2$CONHR$^6$, hydroxyl group, —PO$_4$H, or SO$_3$H, Y and Y' are each hydrogen atom, —COOH, a group equivalent to COOH, —CONHR$^6$, —OR$^6$, —PO$_4$H, —SO$_3$H, halogen atom, or methyl, in which $R^6$ is alkyl of 1 to 4 carbon atoms optionally substituted with halogen atom, or hydrogen atom, k is an integer of 1 to 4, and, $R^1$, $R^2$ and $R^3$ are each —COOH, a group equivalent to COOH, alkyl of 1 to 6 carbon atoms, alkenyl of 2 to 6 carbon atoms, alkynyl of 2 to 6 carbon atoms, cycloalkyl of 3 to 7 carbon atoms, or alkyl of 1 to 6 carbon atoms substituted with any of phenyl, phenylthio, alkylthio of 1 to 6 carbon atoms, COOH or heterocycle, provided that the phenyl, the phenylthio and the heterocycle may be substituted with alkyl of 1 to 6 carbon atoms, hydroxyl group, nitro, halogen atom, —SO$_3$H or —PO$_4$H or a pharmaceutically acceptable salt thereof, or a prodrug thereof.

The present invention relates to a compound in which, in the general formula (1), $B^1$ and $B^2$ are each a single bond or alkylene of 1 to 3 carbon atoms optionally substituted with $R^4$, in which $R^4$ is halogen atom; alkyl of 1 to 6 carbon atoms; alkenyl of 2 to 6 carbon atoms; alkynyl of 2 to 6 carbon atoms; cycloalkyl of 3 to 7 carbon atoms; optionally substituted heterocycle; optionally substituted aralkyl; or optionally substituted aryl, and the substituent thereof is alkyl of 1 to 6 carbon atoms, alkenyl of 2 to 6 carbon atoms, alkynyl of 2 to 6 carbon atoms, cycloalkyl of 3 to 7 carbon atoms, or aryl, D is a single bond, —NHCO— or —NHCO—$R^5$—, in which $R^5$ is alkylene of 1 to 6 carbon atoms; arkenylene of 2 to 6 carbon atoms; alkynylene of 2 to 6 carbon atoms; cycloalkylene of 3 to 7 carbon atoms; optionally substituted heterocycle; optionally substituted aralkylene; or optionally substituted arylene, and the substituent thereof is halogen atom, alkyl of 1 to 6 carbon atoms, alkenyl of 2 to 6 carbon atoms, alkynyl of 2 to 6 carbon atoms, cycloalkyl of 3 to 7 carbon atoms, or aryl, E is —COOH or a group equivalent to COOH, hydrogen atom, hydroxyl group, amino group, halogen atom, or —COOCH$_3$, n is an integer of 1 to 3, m is 1, G is hydroxyl group, or a group of the formula:

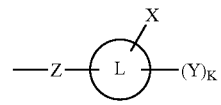

in which Z is —NH—, -Asp-Ala-NH—, -Asp-Ala-, —NH-CZ$^1$(Z$^2$)-, -Asp-NH—, -Asp-NH-CZ$^1$(Z$^2$)-, or —NH-CZ$^1$(Z$^2$)-CZ$^1$(Z$^2$), Ring L is a 5- to 10-membered ring optionally containing a heteroatom and/or unsaturated bond, $Z^1$ and $Z^2$ are each a hydrogen atom, hydroxyl group, amino group, cyano group, nitro group, alkyl of 1 to 6 carbon atoms, or halogen atom, X is hydrogen atom, —COOH, a group equivalent to COOH, —CONHR$^6$, —OCH$_2$COOR$^6$, —OCH$_2$CONHR$_6$, hydroxyl group, —PO$_4$H, —SO$_3$H, -CZ$^1$(Z$^2$)-X', or a group of the formula:

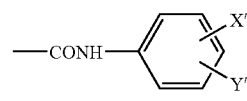

in which X' is hydrogen atom, —COOH, a group equivalent to COOH, —CONHR$^6$, —OCH$_2$COOR$^6$, —OCH$_2$CONHR$^6$, hydroxyl group, —PO$_4$H, or —SO$_3$H, Y and Y' are each hydrogen atom, —COOH, a group equivalent to COOH, —CONHR$^6$, —OR$^6$, —PO$_4$H, —SO$_3$H, halogen atom, or methyl, $R^6$ is alkyl of 1 to 4 carbon atoms optionally substituted with halogen atom, or hydrogen atom, k is an integer of 1 to 4, and $R^1$, $R^2$ and $R^3$ are each alkyl of 1 to 6 carbon atoms, alkenyl of 2 to 6 carbon atoms, alkynyl of 2 to 6 carbon atoms, cycloalkyl of 3 to 7 carbon atoms, or alkyl of 1 to 6 carbon atoms substituted with any of phenyl, phenylthio, alkylthio of 1 to 6 carbon atoms, or heterocycle, provided that the phenyl, phenylthio and heterocycle may be substituted with alkyl of 1 to 6 carbon atoms, hydroxyl group, nitro, halogen atom, —$SO_3H$ or —$PO_4H$, or a pharmaceutically acceptable salt thereof, or a prodrug thereof.

The present invention relates to a compound in which, in the general formula (1), $B^1$ is a single bond or methylene, $B^2$ is a single bond or alkylene of 1 to 3 carbon atoms, D is a single bond, —NHCO—, a group of the formula:

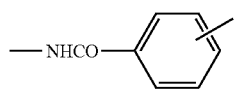 or 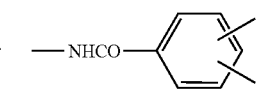

in which the benzene ring is optionally substituted with halogen atom, amino group, alkyl of 1 to 6 carbon atoms, alkenyl of 2 to 6 carbon atoms, alknyl of 2 to 6 carbon atoms, cycloalkyl of 3 to 7 carbon atoms or aryl, a group of the following formula:

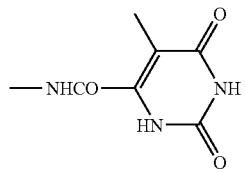

or a group of the following formula:

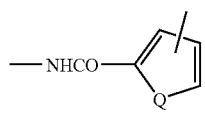

in which Q is oxygen atom or NH,

E is hydrogen atom, hydroxyl group, amino group, halogen atom, —COOH, —$COOCH_3$, or tetrazole ring, n is an integer of 1 to 2, m is 1, $R^1$ is alkyl of 1 to 6 carbon atoms, alkenyl of 2 to 6 carbon atoms, alkynyl of 2 to 6 carbon atoms, cycloalkyl of 3 to 7 carbon atoms, or aryl, $R^2$ is alkyl of 1 to 6 carbon atoms, phenyl, naphthyl, isobutyl, 2-carbamoylethyl, 2-methylthioethyl, methylthiomethyl, 2-ethylthioethyl, ethylthiomethyl, naphthylmethyl, phenethyl, 4-thiazoylmethyl, 4-imidazolylmethyl, 3-tetrahydrofuranyl, 3-indolylmethyl, cyclohexylmethyl, or benzyl in which the benzene ring may be substituted with halogen atom, hydroxyl group, or alkyloxy group of 1 to 6 carbon atoms, and G is any one of the group represented by the following formulas:

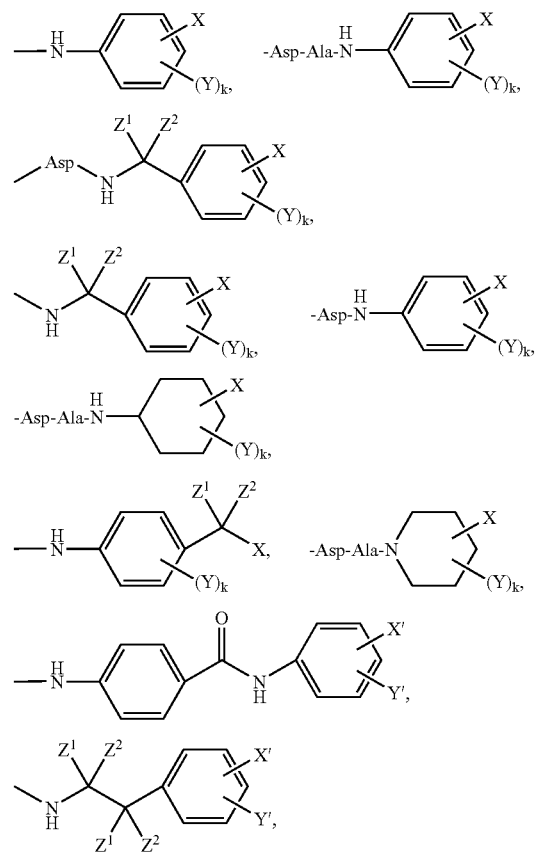

in which X and X' are each hydrogen atom, —COOH, —$CONHR^6$, —$OCH_2COOR^6$, —$OCH_2CONHR^6$, hydroxy group, —$PO_4H$, —$SO_3H$ or tetrazole ring, Y and Y' are each hydrogen atom, —COOH, —$CONHR^6$, —$OR^6$, —$PO_4H$, —$SO_3H$, halogen atom, methyl or terazole ring, $R^6$ is alkyl of 1 or 2 carbon atoms optionally substituted with halogen atom, or hydrogen atom, k is an integer of 1 or 2, and $Z^1$ and $Z^2$ are each hydrogen atom, hydroxyl group, amino group, cyano group, nitro group, alkyl of 1 to 6 carbon atoms, or halogen atom, or a pharmaceutically acceptable salt thereof, or a prodrug thereof.

The present invention relates to a compound in which, in the general formula (1), $B^1$ is a single bond, $B^2$ is alkylene of 1 or 2 carbon atoms, D is a single bond, —NHCO—, or a group of the following formula:

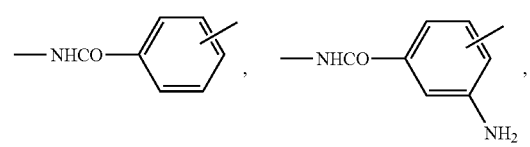

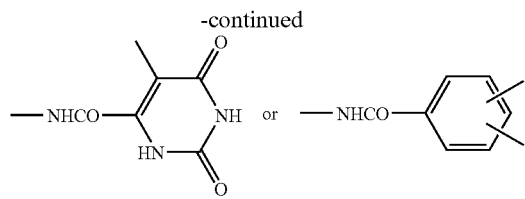

E is hydrogen atom, hydroxyl gourp, halogen atom, —COOH or tetrazole ring, n is an integer of 1 or 2, m is 1, $R^1$ is isopropyl, $R^2$ is isobutyl or cyclohexylmethyl, $R^3$ is benzyl, isobutyl, phenylthiomethyl or cyclohexylmethyl, and G is any one of the group represented by the following formulas:

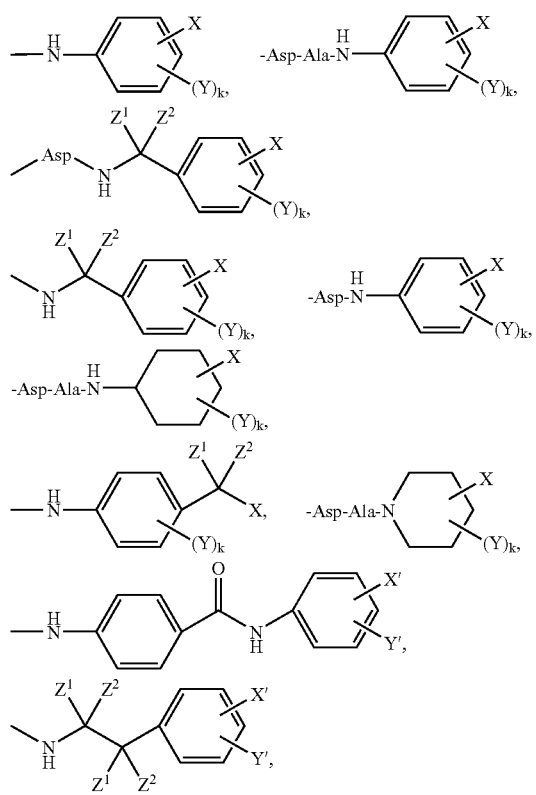

in which X and X' are each COOH, $CONH_2$, hydroxyl group, $OCH_2COOH$ or tetrazole ring, Y and Y' are each hydrogen atom, COOH, $CONH_2$, halogen atom, methyl or a tetrazole ring, k is an integer of 1 or 2, and $Z^1$ and $Z^2$ are each hydrogen atom, or a pharmaceutically acceptable salt thereof, or a prodrug thereof.

The present invention relates to a compound in which, in the general formula (1), a partial structure other than G is a group of the formula:

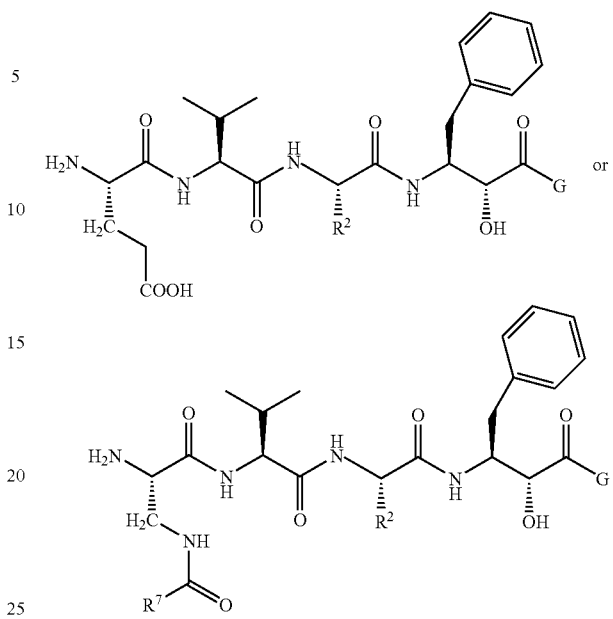

in which $R^2$ is isobutyl or cyclohexylmethyl, $R^7$ is a group of the following formula:

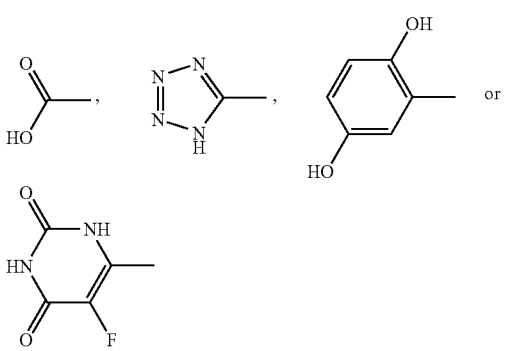

and

G is the following formula:

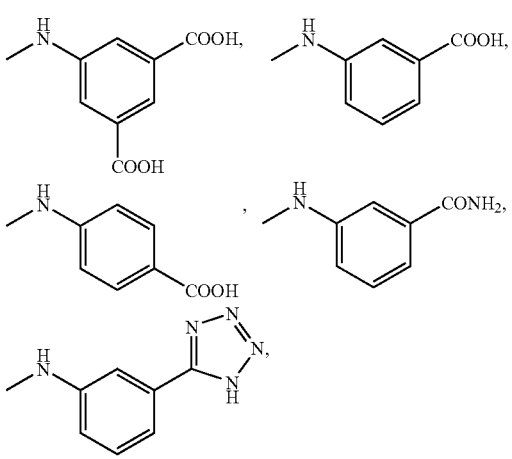

-continued

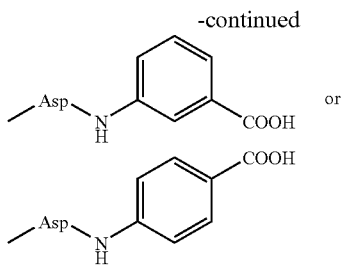

or a pharmaceutically acceptable salt thereof, or a prodrug thereof.

It is preferred that the molecular weight of the compound represented by the general formula (1) is 1100 or less.

The present invention also relates to a β-secretase inhibitor containing the above compound as an active ingredient.

The present invention relates to an agent for preventing or treating (i) neurodegenerative disease, (ii) neuropathy in cerebrovascular disease, head trauma·spinal damage, encephalitis sequela, or cerebral palsy, (iii) memory disorder, or (iv) mental disease associated with β-secretase containing the above compound as an active ingredient.

The present invention relates to an agent for preventing or treating (i) neurogenerative disease, (ii) neuropathy in cerebrovascular disease, head trauma·spinal damage, encephalitis sequela, or cerebral palsy, (iii) memory disorder or (iv) mental disease by promoting secretion of sAPPα, or promoting secretion of sAPPα, and inhibiting production·secretion of a βamyloid protein, or inhibiting production·secretion of a βamyloid protein, containing the aforementioned compound as an active ingredient.

The present invention relates to an agent for treating the neurodegenerated disease, Alzheimer's disease or Parkinson's disease, containing the aforementioned compound as an active ingredient.

The present invention relates to an agent for promoting sAPPα secretion containing the aforementioned compound as an active ingredient.

The present invention relates to an agent for inhibiting production secretion of a βamyloid protein.

The present invention relates to a neurotrophic factor-like acting agent containing the aforementioned compound as an active ingredient.

The present invention relates to an agent for preventing or treating neuropathy or mental disease in head trauma·spinal damage, encephalitis sequela, or cerebral palsy containing the aforementioned compound as an active ingredient.

The present invention relates to the use of a β-secretase inhibitor of the aforementioned compound in the preparation of a sAPPα secretion promoter, a neurotrophic factor-like acting agent, or an agent for preventing or treating neuropathy, memory disorder or mental disease head trauma·spinal damage, encephalitis sequela, or cerebral palsy.

The present invention also relates to a method for treating (i) neurogenerative disease, (ii) neuropathy in cerebrovascular disease, head trauma·spinal damage, encephalitis sequela, or cerebral palsy, (iii) memory disorder, or (iv) mental disease associated with β-secretase, which comprises administering an effective amount of a β-secretase inhibitor containing the aforementioned compound as an active ingredient to a mammal.

As used herein, the "alkyl of 1 to 6 carbon atoms" include straight or branched alkyl of 1 to 6 carbon atoms, specifically, methyl, ethyl, n-propyl, 2-propyl, n-butyl, 2-butyl, isobutyl, 3-methyl-2-propyl, 1,1-dimethylethyl, n-pentyl, and n-hexyl, preferably, methyl, ethyl, n-propyl, and 2-propyl.

The "alkenyl of 2 to 6 carbon atoms" includes vinyl, 2-propenyl, 1-propenyl, 2-butenyl, 1-butenyl, and 2-methyl-1-propenyl.

The "alkynyl of 2 to 6 carbon atoms" includes ethynyl, 2-pronynyl, 2-bunynyl, 3-butynyl, 2-pentynyl, 3-pentynyl, and 4-pentynyl.

The "cycloalkyl of 3 to 7 carbon atoms" includes cyclopropyl, cyclobutyl, cyclopentyl, cyclohexyl, and cyclopentyl.

The "aryl" includes phenyl, and naphthyl, preferably phenyl.

The "heterocycle" includes a heterocycle having an unsaturated bond such as an aromatic heterocycle and a saturated heterocycle. Examples of the aromatic heterocycle include a 5- to 10-membered aromatic ring containing 1 to 3 heteroatoms such as pyridyl, pyrimidyl, pyridazyl, thienyl, furyl, pyrrolyl, imidazolyl, oxazolyl, isooxazolyl, thiazolyl, isothiazolyl, triazolyl, indolyl, benzothiazolyl, quinazolyl, and isoquinazolyl, preferably pyridyl, pyrimidyl, thienyl, pyrrolyl, indolyl, benzothiazolyl, and isoquinazolyl, particularly preferably pyridyl, pyrimidyl, and thienyl. Examples of the saturated heterocycle include piperidinyl, pyrrolydinyl, piperazinyl, imidazolyl, morpholinyl, thiomorpholinyl, and tetrafuryl.

The "Ring L" includes a cycloalkyl ring such as cyclohexyl and cyclopentyl; an aromatic ring such as phenyl and naphthyl, an unsaturated heterocycle such as aromatic heterocycle; and a saturated heterocycle. Examples of the aromatic heterocycle include pyridyl, pyrimidyl, pyridazyl, thienyl, furyl, pyrrolyl, imidazolyl, oxazolyl, isooxazolyl, thiazolyl, isothiazolyl, triazolyl, indolyl, benzothiazolyl, quinazolyl, and isoquinazolyl, preferably pyridyl, thienyl, pyrrolyl, indolyl, and benzothiazolyl, particularly preferably pyridyl, and thienyl. Examples of the saturated heterocycle include piperidinyl, pyrrolydinyl, piperazinyl, imidazolyl, morpholinyl, thiomorpholinyl, and tetrafuryl.

The "aralkyl" represents alkyl of 1 to 6 carbon atoms substituted with aryl, specifically, benzyl, phenethyl, phenylpropyl, phenylbutyl, and naphthylmethyl, preferably benzyl, and phenethyl.

The "a group equivalent to COOH" includes hydroxamic acid, acyl-cyanamide, tetrazole, oxooxadiazole, oxothiadiazole, thioxooxadiazole, oxooxathiadiazole, mercaptoazole, sulfinylazole, sulfonylazole, isooxazole, isothiazole, hydroxythiadiazole, hydroxyl-γ-pyrone, phosphinic acid, phosphonic acid, phosphonamide, sulfonamide, and acylsulfonamide, preferably tetrazole.

The "prodrug" refers to a compound which is hydrolyzed in a living body, and reproduces the compound of the present invention. The prodrug of the present invention includes compounds which are prepared by any procedure for converting into a prodrug known to a person skilled in the art. For example, when the compound of the present invention has a carboxyl group or an amino group, compounds in which those groups are derived into an ester group or an amide group easily hydrolizable in a living body correspond to a prodrug. When a compound has a carboxyl group, examples of the prodrug include compounds in which the carboxyl group is introduced into alkyl such as methyl, and ethyl, alkyloxyalkyl such as methyloxymethyl, ethyloxymethyl, 2-methyloxyethyl, and 2-methyloxyethyloxymethyl, acyloxymethyl such as pivaloyloxymethyl, acetyloxymethyl, cyclohexylacetyloxymethyl, and 1-methylcyclohexylcarbonyloxymethyl, alkoxycarbonylalkyl such as ethyloxycarbonyloxy-1-ethyl, or cycloalkyloxycarbonyalkyl such as cyclohexyloxycarbonyloxy-1-ethyl. When a compound has an amino group, examples of a prodrug include compounds in which an amino group is introduced into acetamide.

The compound (1) which is an active ingredient of a medicament of the present invention can be formed in a pharmaceutically acceptable salt thereof. Examples of the pharmaceutically acceptable salt include an acid addition salt and a base addition salt. Examples of the acid addition salt include inorganic acid salts such as hydrochloride, hydrobromide, sulfate, etc. and organic acid salts such as citrate, oxalate, malate, tartarate, fumarate, maleate, etc. and examples of a base addition salt include inorganic base salts such as a sodium salt, a calcium salt, etc. and organic base salts such as a meglumine salt, a trishydroxymethylaminomethane salt, etc. In addition, the present invention includes a hydrate and a solvate of the compound (1) or a pharmaceutically acceptable salt thereof.

The compound of the present invention or a pharmaceutically acceptable salt thereof can be prepared by the following method or a similar method.

Since the compound of the present invention has a peptidic linkage(s), each amino acid unit can be prepared by the method which is conventionally used in peptide chemistry, for example, the method described in "The Peptides", vol., by Schroder and Luhker, Academic Press, New York, U.S.A (1966), and "Base and Experiment of Peptide Synthesis" by Nobuo Izumiya, et al., Maruzen (1985), and the compound of the present invention, for example, can be prepared using a liquid phase method shown by the following scheme and a solid phase method shown by the following scheme II.

Scheme I (liquid phase method)

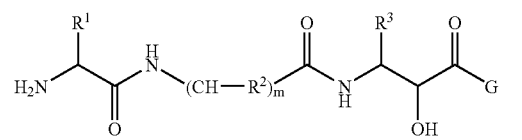

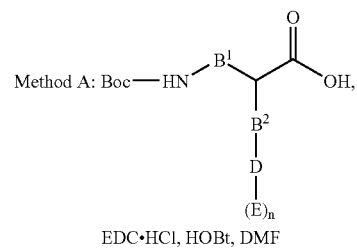

Method A: EDC·HCl, HOBt, DMF

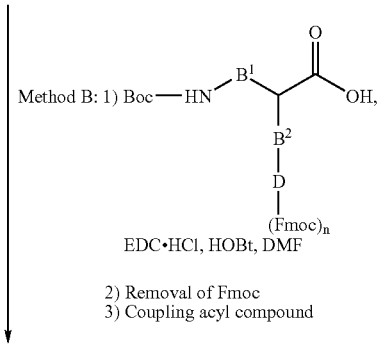

Method B: 1) EDC·HCl, HOBt, DMF
2) Removal of Fmoc
3) Coupling acyl compound

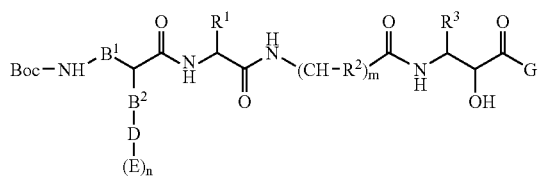

Removal of protecting group (deprotection)

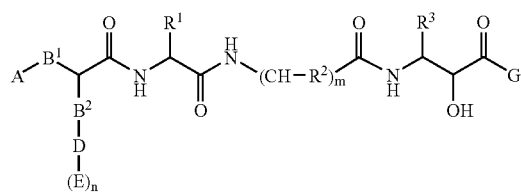

Scheme II (Solid pase method)
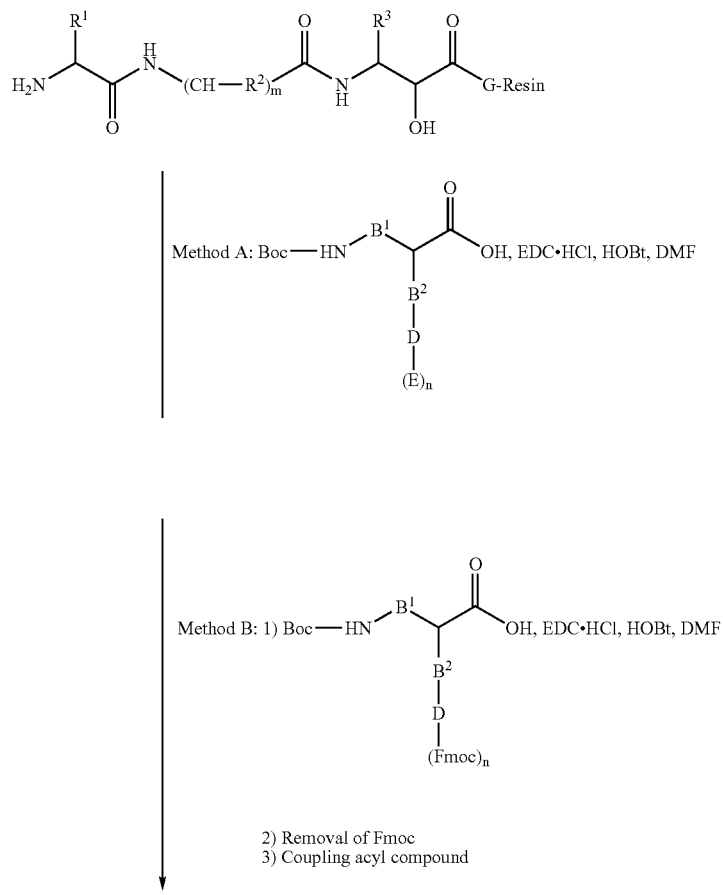
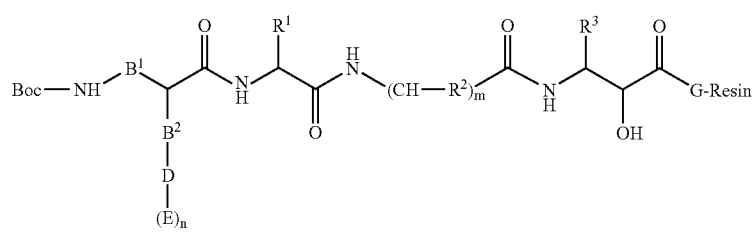
Removal of protecting group (deprotection)
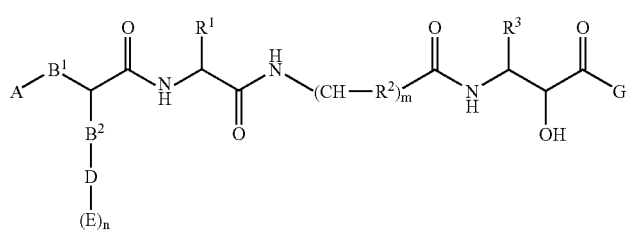

Further, it can be also prepared by the column or batch method.

The formation of a peptidic linkage can be exemplified by the azide, acid chloride, acid anhydride, carbodiimide, carbodiimide-active, active ester, carbonylimidazole, redox, or enzyme method, and a method using Woodward's reagent K. Examples of a condensation reaction in a solid phase method include, as a main method, the acid anhydride, carbodiimide, or active ester method among the aforementioned methods.

Furthermore, when a peptide chain is extended by the solid phase method, the C-terminal amino acid is bound to a support such as a resin which is insoluble in the organic solvent used. Herein, a resin in which a functional group is introduced for the purpose of binding an amino acid to a resin, an entity in which a spacer is inserted between a resin and a functional group, and a resin in which a chain referred to as a handle, which is cut at various places depending on the conditions, can also be used depending on the purpose. Examples of such a resin include Wong resin, 2-chlorotrityl resin, halomethyl resin such as chloromethyl resin, oxymethyl resin, and C-terminal amidated resin.

Furthermore, before these condensation reactions are performed, a carboxyl group, an amino group, a hydroxyl group, or an amidino group not involved in the condensation reaction can be protected by conventional means. Conversely, a carboxyl group and an amino group directly involved in the condensation reaction can be activated.

To protect a functional group not involved in the condensation reaction, the functional group can be protected with a protecting group which is usually used in organic chemistry, or a protecting group described, for example, in "Protective Groups in Organic Synthesis", by Green, John Wiley & Sons, Inc. (1981).

A condensation reaction used in peptide synthesis is usually performed in a solvent. Examples of solvents include chloroform, dichloromethane, ethyl acetate, N,N-dimethylformamide, dimethyl sulfoxide, pyridine, dioxane, tetrahydrofuran, N-methylpyrrolidone, water, methanol, and a mixture thereof. The condensation rection is carried out at a range of −30 to 50° C. as in conventional cases.

Furthermore, the elimination of a protecting group in the preparation of the present invention can be selected according to the kind of protecting group used as far as the protecting group can be eliminated without influencing on peptidic linkage. Examples include acid treatment with hydrogen chloride, hydrogen bromide, anhydrous hydrogen fluoride, methanesulfonic acid, trifluoromethanesulfonic acid, trifluoroacetic acid, or a mixture thereof, alkali treatment with sodium hydroxide, potassium hydroxide, hydrazine, diethylamine, or piperidine, sodium treatment in liquid ammonia, reduction with palladium carbon, and treatment with a silylating agent such as trimethylsilyl triflate, trimethylsilyl bromide, etc. In a deprotecting reaction by the treatment with the acid or the silylating agent mentioned above, it is preferable to add a cation scavenger such as anisole, phenol, cresol, anisole, thioanisole, ethanedithiol, etc. to efficiently perform the deprotecting reaction. A method for cleaving a peptide of the present invention synthesized by the solid phase method, from a solid phase is also performed according to conventional methods.

The prepared peptide of the present invention can be subjected to conventional separation and purification after completion of the aforementioned series of reactions. For example, by extraction, distribution, re-precipitation, recrystallization, column chromatography, etc., the peptide of the present invention can be obtained in a purer form.

The compound of the present invention or a pharmaceutically acceptable salt thereof has asymmetry in some cases, or has a substituent having an asymmetric carbon in some cases, such that there is an optical isomer. The compound of the present invention includes a mixture of the respective or isolated isomers. Examples of a method for obtaining such optical isomer pure include optical resolution.

As an optical resolution, the compound of the present invention or an intermediate thereof may form a salt with an optically active acid (e.g. monocarboxylic acids such as mandelic acid, N-benzyloxyalanine, lactic acid, etc., dicarboxylic acids such as tartaric acid, o-diisopropylidenetartaic acid, malic acid, etc., sulfonic acids such as camphorsulfonic acid, bromocamphorsulfonic acid, etc.) in an inert solvent (e.g. alcohol solvents such as methanol, ethanol, and 2-propanol, ether solvents such as diethyl ether, ester solvents such as ethyl acetate, aromatic hydrocarbon solvents such as toluene, acetonitrile, and a mixed solvent thereof).

In addition, when the compound of the present invention or an intermediate thereof has an acidic substituent such as a carboxyl group, it may be formed as a salt with optically active amines (e.g. organic amines such as α-phenethylamine, quinine, quinidine, cinchonidine, cinchonine, strychnine, etc.).

Examples of the temperature used to form a salt include a range from room temperature to the boiling point of the solvent. In order to improve optical purity, it is desirable to raise the temperature to near boiling point of the solvent only once. Chemical yield can be improved by cooling before filtering of the precipitated salt, if necessary. It is suitable that an amount of an optically active acid or amine to be used in a range of 0.5 to 2.0 molar equivalents, preferably in a range of around 1 molar equivalent relative to that of the substrate. If necessary, a crystal may be recrystallized in an inert solvent (e.g. alcohol solvents such as methanol, ethanol, and 2-propanol, ether solvents such as diethyl ether, ester solvents such as ethyl acetate, aromatic hydrocarbon solvents such as toluene, and acetonitrile, and a mixed solvent thereof) to obtain an optically active salt having a high purity. If necessary, the resulting salt may be treated with an acid or a base by conventional methods to obtain a free compound.

The treating agent of the present invention can be administered orally or parenterally. When orally administered, the agent can be administered in an administration form which is conventionally used. When administered parenterally, the agent can be administered in a form of an agent for topical application, injection, transdermal agent, or nasal agent.

The above dosage form is formulated into a preparation with a pharmaceutically acceptable excipient or additive by conventional methods. Examples of a pharmaceutically acceptable excipient or additive include a carrier, binder, flavor, buffer, thickener, colorant, stabilizer, emulsifier, dispersant, suspending agent, and antiseptic.

Examples of a pharmaceutically acceptable carrier include magnesium carbonate, magnesium stearate, talc, sugar, lactose, pectin, dextrin, starch, gelatin, tragacanth, methylcellulose, sodium carboxymethylcellulose, low melting point wax, and cacao butter. A capsule can be formulated by putting the present compound together with a pharmaceutically acceptable carrier therein. The treating agent of the present invention can be added by mixing with a pharmaceutically acceptable excipient, or without the excipient into a capsule. A cachet can be prepared by similar methods.

Examples of a liquid preparation for injection include a solution, suspension, emulsion, etc. such as an aqueous solution, or water-propylene glycol solution. The liquid preparation may also be prepared in the form of a solution of polyethylene glycol or/and propylene glycol, which may contain water. A liquid preparation suitable for oral administration can be prepared by adding water to the present compound and, if necessary, adding a colorant, flavor, stabilizer, sweetener, solubilizer, and thickener. A liquid preparation suitable for oral preparation may be prepared by adding the present compound or a pharmaceutically acceptable salt thereof together with a dispersant to water to increase viscosity. Examples of a thickener include pharmaceutically acceptable natural or synthetic gum, resin, methylcellulose, sodium carboxymethylcellulose or known suspending agent, etc.

Examples of an agent for topical application include the aforementioned liquid preparation, and a cream, aerosol, spray, powder, lotion, and ointment. The above agent for topical application can be prepared by mixing the present compound or a pharmaceutically acceptable salt thereof with a pharmaceutically acceptable diluent and carrier that are conventionally used. An ointment or cream is obtained, for example, by formulating into a preparation by adding a thickener and/or a gelling agent to an aqueous or oily base. Examples of a base include water, liquid paraffin, and vegetable oil (peanut oil, castor oil). Examples of a thickener include soft paraffin, aluminum stearate, cetostearyl alcohol, propylene glycol, polyethylene glycol, lanolin, hydrogenated lanolin, beeswax, etc.

A lotion can be prepared by adding one or more kinds of pharmaceutically acceptable stabilizer, suspending agent, emulsifier, diffusing agent, thickener, colorant, and flavor to an aqueous or oily base.

A powder is formulated into a preparation with a base for a pharmaceutically acceptable powder. Examples of a powder include talc, lactose, starch, etc. Drops can be formulated into a preparation from an aqueous or non-aqueous base and one or more kinds of pharmaceutically acceptable diffusing agent, suspending agent, and solubilizer.

The agent for topical application may contain an antiseptic such as methyl hydroxybenzoate, propyl hydroxybenzoate, chlorocresol, and benzalkonium chloride, or a bacteriostat.

A preparation of a liquid spray, a powder or a drop containing the present compound or a pharmaceutically salt thereof as an active ingredient can be administered nasally.

The dose and administration interval are different depending on symptoms, age, weight, and administration form and, when orally administered, usually a range of about 1 to about 500 mg, preferably a range of about 5 to about 100 mg per adult per day which can be administered once or in divided doses. When administered as an injection, a range of about 0.1 to about 300 mg, preferably a range of about 1 to about 100 mg can be administered once or in divided doses.

A process for preparing the present compound will be explained below by Examples.

When the present reaction is performed, the technique of protection and deprotection can be used, if necessary. The technique of protection and deprotection is described in detail in the aforementioned Protective Groups in Organic Synthesis [authored by Green, John Wiley & Sons, Inc. (1981)].

EXAMPLES

The meanings of abbreviations used in Examples are as follows:
Me: methyl group
Boc: tert-butoxycarbonyl group
DIPCDI: diisopropylcarbodiimide
Fmoc: 9-fluorenylmethoxycarbonyl group
HOBT: N-hydroxybenzotriazole
DMF: N,N'-dimethylformamide
Apns: amino acid residue of (2S,3S)-3-amino-2-hydroxy-4-phenylbutanoic acid
DMAP: 4-dimethylaminopyridine
Dap: amino acid residue of L-α,β-diaminopropanoic acid
Pns: amino acid residue of (2R,3S)-3-amino-2-hydroxy-4-phenylbutanoic acid
Nst: amino acid residue of (2R,3S)-3-amino-2-hydroxy-5-methylhexanoic acid
Dmt: (R)-5,5-dimethyl-1,3-thiazolidine-4-carboxylic acid Reference Examples Upon synthesis of the present compound, first, Fmoc-Nst-OH (compound 6) which was a fundamental block, was synthesized according to the method described in the literatures. Namely, using Z-Leo-OH as a raw material, TMSCN was reacted on N-αZ protected aminoaldehyde derived by conventional methods, and the resulting cyanohydrin was introduced into an α-hydroxy-β-amino acid derivative by acid hydrolysis. After being separated and purified into each isomer by column chromatography, the objective compound 6 was obtained via deprotection and 9-fluorenylmethoxycarbonylation. Fmoc-Pns-OH (compound 7) and Fmoc-Apns were synthesized separately as an HMC isostere similar to Nst. Using H-Pns-OH and H-Apns-OH as starting raw materials, 9-fluorenylmethoxycarbonylation was elaborated using the same manner as that described above to obtain the objective product.

Reference Example 1

Introduction of amino acid into 2-chlorotrityl chloride resin (Clt resin)

A Clt resin, Fmoc amino acid derivative (2.5 eq), DCE (2 mL) and DIEA (2.5 eq) were successively added to a reactor under Ar atmosphere, and these were reacted for 2 hours. After completion of the reaction, MeOH (200 μL) and DIEA (0.5 eq) were added and, the mixture was shaken for 20 minutes. Thereafter, the mixture was thoroughly washed with DMF, CHCl$_3$ and MeOH, and the resin was dried under vacuum. Using the dry resin, a substitution rate was calculated.

Reference Example 2

Introduction of amino acid into Wang resin

Wang resin was added to a reactor, and the resin was adopted with DMF. Then, an Fmoc amino acid derivative (3 eq), DMF (2 mL), DIPCDI (3 eq) and DMAP (0.1 eq) were added to react for 90 minutes. After the reaction, the reaction was thoroughly washed with DMF, CHCl$_3$ and MeOH, and dried under vacuum. Using the dry resin, a substitution rate was obtained.

Reference Example 3

Removal of Nα-amino group

After a protected peptide resin in a reactor was manually shaken with 20% piperidine/DMF for 1 minute, the reaction solution was filtered, 20% piperidine/DMF was newly added thereto, followed by shaking for 20 minutes. After the reaction, the resin was sufficiently washed with DMF and $CHCl_3$ until the filtrate became neutral.

Reference Example 4

Condensation reaction of amino acid

An Fmoc amino acid derivative (2.5 eq), and $HOBt \cdot H_2O$ (2.5 eq) were added to a protected peptide resin in a reactor, followed by dissolution with DMF. Then, DIPCDI (2.5 eq) was added, and the mixture was shaken for 90 minutes. After completion of the reaction, the resin was thoroughly washed with DMF, a part of the resin was taken, and the progress of the reaction was confirmed by Kaiser test. When it was determined that the reaction was not completed, the condensation reaction was repeated.

Reference Example 5

Removal of resin and deprotection

A protected peptide resin was reacted with m-cresol (2.5%), thioanisole (2.5%), $H_2O$ (2.5%) and TFA (92.5%) for 90 minutes. After the resin was distilled off from the reaction solution, ether was added to wash the material, and the supernatant was removed by centrifugation. The resulting crude product was dissolved in water, and lyophilized or dried under vacuum.

Reference Example 6

Fmoc-Nst-OH (6)

H-Nst-OH (250 mg, 1.6 mmol) was dissolved in THF:$H_2O$ (1:2), $K_2CO_3$ (214 mg, 1.6 mmol) and Fmoc-OSu (470 mg, 1.4 mmol) were added under ice-cooling, and the mixture was stirred at room temperature overnight. 1N HCl was added to the reaction solution to adjust pH to 3 or lower, and the solvent was concentrated under reduced pressure. The residue was dissolved in AcOEt. The solution was washed with 1N HCl and brine, and dried over anhydrous $MgSO_4$. The solvent was concentrated under reduced pressure, and the residue was crystallized from n-hexane to obtain the objective product as white crystals.

Yield, 580 mg (98%); mp, 161-164° C.; $[\alpha]^{23}_D$ -22.8° (c=0.50, DMSO); Rt, 29.27 min; 1H NMR (DMSO-$d_6$) δ (ppm); 0.83-0.85 (m, 6H), 1.12-1.37 (m, 2H), 1.42-1.51 (m, 1H), 3.60 (brs, 1H), 3.78 (brs, 1H), 4.19-4.23 (m, 2H), 4.31-4.39 (m, 1H), 6.81 (d, 1H, J=9.3 Hz), 7.31-7.42 (m, 4H), 7.64-7.68 (m, 2H), 7.86-7.89 (m, 2H); TOF-MS m/z: 406.29 $(M+Na)^+$.

Reference Example 7

Fmoc-Pns-OH (7)

Using H-Pns-OH (2.00 g, 10 mmol) as a starting raw material, the title compound was synthesized in the same method as that for Fmoc-Nst-OH.

Yield, 3.76 g (88%); mp, 184-188° C.; $[\alpha]^{24}_D$ -57.4° (c=0.50, dioxane); Rt, 30.32 min; 1H NMR (DMSO-$d_6$) δ (ppm); 2.68-2.76 (m, 1H), 2.82-2.88 (m, 1H), 3.93 (d, 1H, J=2.7 Hz), 4.01-4.17 (m, 4H), 7.10-7.43 (m, 9H), 7.66 (dd, 2H, J=4.8, 6.9 Hz), 7.88 (dd, 2H, J=8.4, 16 Hz); TOF-MS m/z: 440.33 $(M+Na)^+$.

Reference Example 8

Fmoc-Apns-OH

Using H-Apns-OH (661 mg, 3.4 mmol) as a starting raw material, the title compound was synthesized according to the same method as that for Fmoc-Nst-OH.

Yield, 1.20 g (85%); mp, 184-186° C.; [α] 26D -5.80° (c=0.50, dioxane); Rt, 29.75 min; 1H NMR (DMSO-$d_6$) δ (ppm); 2.71-2.74 (m, 2H), 3.95-4.12 (m, 5H), 7.12-7.47 (m, 9H), 7.63 (t, 2H, J=6.6 Hz), 7.87 (d, 2H, J=7.5 Hz); TOF-MS m/z: 440.43 $(M+Na)^+$.

Reference Example 9

Fmoc-Dmt-OH

L-Penicillamine (500 mg, 3.4 mmol) was dissolved in water, and 37% HCHO (750 μL) was added, and the mixture was stirred at room temperature. After 1 hour, $K_2CO_3$ (460 mg, 3.4 mmol) and Fmoc-OSu (790 mg, 2.3 mmol) were added under ice-cooling, and the mixture was stirred at room temperature overnight. 1N HCl was added to the reaction solution to adjust the pH to 3 or lower, and the solvent was concentrated under reduced pressure. The residue was dissolved in AcOEt, and the solution was washed with 1 N HCl, and brine, and dried over anhydrous $Na_2SO_4$. The solvent was concentrated under reduced pressure, and the residue was crystallized from n-hexane to obtain the objective product as white crystals.

Yield, 880 mg (69%); mp, 48-52° C.; $[\alpha]^{28}_D$ -37.8° (c=0.50, DMSO); Rt, 28.06 min; 1H NMR (DMSO-$d_6$) δ (ppm); 1.40 (d, 3H, J=13 Hz), 1.52 (d, 3H, J=7.2 Hz), 4.12-4.38 (m, 4H), 4.56-4.68 (m, 2H), 7.29-7.44 (m, 4H), 7.61-7.68 (m, 2H), 7.87-7.91 (m, 2H); TOF-MS m/z: 406.47 $(M+Na)^+$

Example 1

H-Glu-Val-Asn-Nst-Asp-Ala-Glu-Phe-OH (8)

Using Fmoc-Phe Wang resin (0.520 mmol/g) as the starting resin, and compound 6, the title compound was synthesized according to the aforementioned procedure. The resulting crude product was purified using preparative HPLC to obtain the objective product as a white powder.

Yield, 52%; purity, >98% by analytical HPLC (Rt, 18.68 min); TOF-MS m/z: 967.10 $(M+H)^+$.

Example 2

H-Glu-Val-Asn-Pns-Asp-Ala-Glu-Phe-OH (9)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 73%; purity, >98% by analytical HPLC (Rt, 19.30 min); TOF-MS m/z: 1001.1 $(M+H)^+$.

Example 3

H-Glu-Val-Asp-Pns-Asp-Ala-Glu-Phe-OH (10)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 64%; purity, >98% by analytical HPLC (Rt, 19.28 min); TOF-MS m/z: 1002.1 $(M+H)^+$.

Example 4

H-Glu-Val-Gln-Pns-Asp-Ala-Glu-Phe-OH (11)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 63%; purity, >98% by analytical HPLC (Rt, 18.12 min); TOF-MS m/z: 1015.1 $(M+H)^+$.

Example 5

H-Glu-Val-Glu-Pns-Asp-Ala-Glu-Phe-OH (12)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 48%; purity, >98% by analytical HPLC (Rt, 19.31 min); TOF-MS m/z: 1016.1 $(M+H)^+$.

Example 6

H-Glu-Val-Met-Pns-Asp-Ala-Glu-Phe-OH (13)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 51%; purity, >98% by analytical HPLC (Rt, 20.23 min); TOF-MS m/z: 1018.2 $(M+H)^+$.

Example 7

H-Glu-Val-Leu-Pns-Asp-Ala-Glu-Phe-OH (14)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 39%; purity, >98% by analytical HPLC (Rt, 18.96 min); TOF-MS m/z: 1000.2 $(M+H)^+$.

Example 8

H-Glu-Val-Lys-Pns-Asp-Ala-Glu-Phe-OH (15)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 88%; purity, >98% by analytical HPLC (Rt, 17.04 min); TOF-MS m/z: 1015.0 $(M+H)^+$.

Example 9

H-Glu-Leu-Leu-Pns-Asp-Ala-Glu-Phe-OH (16)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 58%; purity, >98% by analytical HPLC (Rt, 19.66 min); TOF-MS m/z: 1014.1 $(M+H)^+$.

Example 10

H-Glu-Ile-Leu-Pns-Asp-Ala-Glu-Phe-OH (17)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 68%; purity, >98% by analytical HPLC (Rt, 21.34 min); TOF-MS m/z: 1014.2 $(M+H)^+$.

Example 11

H-Glu-Phe-Leu-Pns-Asp-Ala-Glu-Phe-OH (18)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 58%; purity, >98% by analytical HPLC (Rt, 22.34 min); TOF-MS m/z: 1048.2 $(M+H)^+$.

Example 12

H-Glu-Met-Leu-Pns-Asp-Ala-Glu-Phe-OH (19)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 60%; purity, >98% by analytical HPLC (Rt, 19.00 min); TOF-MS m/z: 1032.0 $(M+H)^+$.

Example 13

H-Glu-Val-Leu-Pns-Ala-Ala-Glu-Phe-OH (20)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 43%; purity, >98% by analytical HPLC (Rt, 19.16 min); TOF-MS m/z: 956.11 $(M+H)^+$.

Example 14

H-Glu-Val-Leu-Pns-Asn-Ala-Glu-Phe-OH (21)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 44%; purity, >98% by analytical HPLC (Rt, 19.79 min); TOF-MS m/z: 999.22 (M+H)$^+$.

Example 15

H-Glu-Val-Leu-Pns-Glu-Ala-Glu-Phe-OH (22)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 36%; purity, >98% by analytical HPLC (Rt, 21.00 min); TOF-MS m/z: 1014.0 (M+H)$^+$.

Example 16

H-Glu-Val-Leu-Pns-Gln-Ala-Glu-Phe-OH (23)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 63%; purity, >98% by analytical HPLC (Rt, 23.15 min); TOF-MS m/z: 1013.0 (M+H)$^+$.

Example 17

H-Glu-Val-Leu-Pns-Dmt-Ala-Glu-Phe-OH (24)

Using Fmoc-Phe Wang resin (0.520 mmol/g) as a starting resin, and compound 7 and Fmoc-Dmt-OH, the title compound was synthesized according to the aforementioned procedure. The resulting crude product was purified by preparative HPLC to obtain the objective product as a white powder.

Yield, 21%; purity, >98% by analytical HPLC (Rt, 21.50 min); TOF-MS m/z: 1027.75 (M+H)$^+$.

Example 18

H-Glu-Val-Leu-Apns-Asp-Ala-Glu-Phe-OH (25)

Using Fmoc-Phe Wang resin (0.520 mmol/g) as a starting resin, and Fmoc-Apns-OH, the title compound was synthesized according to the aforementioned procedure. The resulting crude product was purified using preparative HPLC to obtain the objective product as a white powder.

Yield, 41%; purity, >98% by analytical HPLC (Rt, 18.74 min); TOF-MS m/z: 1000.1 (M+H)$^+$.

Example 19

H-Glu-Val-Leu-Apns-Ala-Ala-Glu-Phe-OH (26)

Using Fmoc-Phe Wang resin (0.520 mmol/g) as a starting resin, and Fmoc-Apns-OH, the title compound was synthesized according to the aforementioned procedure. The resulting crude product was purified using preparative HPLC to obtain the objective product as a white powder.

Yield, 36%; purity, >98% by analytical HPLC (Rt, 19.34 min); TOF-MS m/z: 956.29 (M+H)$^+$.

Example 20

H-Glu-Val-Leu-Apns-Asn-Ala-Glu-Phe-OH (27)

Using Fmoc-Phe Wang resin (0.520 mmol/g) as a starting resin, and Fmoc-Apns-OH, the title compound was synthesized according to the aforementioned procedure. The resulting crude product was purified using preparative HPLC to obtain the objective product as a white powder.

Yield, 63%; purity, >98% by analytical HPLC (Rt, 19.16 min); TOF-MS m/z: 999.13 (M+H)$^+$.

Example 21

H-Glu-Val-Leu-Apns-Glu-Ala-Glu-Phe-OH (28)

Using Fmoc-Phe Wang resin (0.520 mmol/g) as a starting resin, and Fmoc-Apns-OH, the title compound was synthesized according to the aforementioned procedure. The resulting crude product was purified using preparative HPLC to obtain the objective product as a white powder.

Yield, 59%; purity, >98% by analytical HPLC (Rt, 19.56 min); TOF-MS m/z: 1014.1 (M+H)$^+$.

Example 22

H-Glu-Val-Leu-Apns-Gln-Ala-Glu-Phe-OH (29)

Using Fmoc-Phe Wang resin (0.520 mmol/g) as a starting resin, and Fmoc-Apns-OH, the title compound was synthesized according to the aforementioned procedure. The resulting crude product was purified using preparative HPLC to obtain the objective product as a white powder.

Yield, 63%; purity, >98% by analytical HPLC (Rt, 19.15 min); TOF-MS m/z: 1013.1 (M+H)$^+$.

Example 23

H-Glu-Val-Leu-Apns-Dmt-Ala-Glu-Phe-OH (30)

Using Fmoc-Phe Wang resin (0.520 mmol/g) as a starting resin, and Fmoc-Apns-OH and Fmoc-Dmt-OH, the title compound was synthesized according to the aforementioned procedure. The resulting crude product was purified using preparative HPLC to obtain the objective product as a white powder.

Yield, 28%; purity, >98% by analytical HPLC (Rt, 20.74 min); TOF-MS m/z: 1028.8 (M+H)$^+$.

Example 24

H-Glu-Val-Leu-Pns-Ala-Val-Glu-Phe-OH (31)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 27%; purity, >98% by analytical HPLC (Rt, 21.75 min); TOF-MS m/z: 984.16 (M+H)$^+$.

Example 25

H-Glu-Val-Leu-Pns-Ala-Leu-Glu-Phe-OH (32)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 42%; purity, >98% by analytical HPLC (Rt, 22.54 min); TOF-MS m/z: 998.15 (M+H)$^+$.

Example 26

H-Glu-Val-Leu-Pns-Ala-Phe-Glu-Phe-OH (33)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 31%; purity, >98% by analytical HPLC (Rt, 22.90 min); TOF-MS m/z: 1032.0 (M+H)$^+$.

Example 27

H-Glu-Val-Leu-Pns-Ala-Glu-Glu-Phe-OH (34)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 58%; purity, >98% by analytical HPLC (Rt, 20.06 min); TOF-MS m/z: 1014.2 (M+H)$^+$.

Example 28

H-Glu-Val-Leu-Pns-Asp-Ala-Gln-Phe-OH (35)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 77%; purity, >98% by analytical HPLC (Rt, 19.47 min); TOF-MS m/z: 999.15 (M+H)$^+$.

Example 29

H-Glu-Val-Leu-Pns-Asp-Ala-Val-Phe-OH (36)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 27%; purity, >98% by analytical HPLC (Rt, 21.90 min); TOF-MS m/z: 970.18 (M+H)$^+$.

Example 30

H-Glu-Val-Leu-Pns-Asp-Ala-Leu-Phe-OH (37)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 47%; purity, >98% by analytical HPLC (Rt, 23.18 min); TOF-MS m/z: 984.05 (M+H)$^+$.

Example 31

H-Glu-Val-Leu-Pns-Asp-Ala-Phe-Phe-OH (38)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 49%; purity, >98% by analytical HPLC (Rt, 23.11 min); TOF-MS m/z: 1018.2 (M+H)$^+$.

Example 32

H-Glu-Val-Leu-Pns-Asp-Ala-Glu-OH (39)

Using Fmoc-Glu (OtBu) Wang resin (0.560 mmol/g) as a starting resin and compound 7, the title compound was synthesized according to the aforementioned procedure. The resulting crude product was purified using preparative HPLC to obtain the objective product as a white powder.

Yield, 37%; purity, >98% by analytical HPLC (Rt, 18.48 min); TOF-MS m/z: 852.87 (M+H)$^+$.

Example 33

H-Glu-Val-Leu-Pns-Asp-Ala-OH (40)

Using Fmoc-Ala Wang resin (0.536 mmol/g) as a starting resin and compound 7, the title compound was synthesized according to the aforementioned procedure. The resulting crude product was purified using preparative HPLC to obtain the objective product as a white powder.

Yield, 64%; purity, >98% by analytical HPLC (Rt, 16.50 min); TOF-MS m/z: 723.82 (M+H)$^+$.

Example 34

H-Glu-Val-Leu-Pns-Asp-OH (41)

Using Fmoc-Asp (OtBu) Wang resin (0.586 mmol/g) as a starting resin and compound 7, the title compound was synthesized according to the aforementioned procedure. The resulting crude product was purified using preparative HPLC to obtain the objective product as a white powder.

Yield, 40%; purity, >98% by analytical HPLC (Rt, 19.62 min); TOF-MS m/z: 652.57 (M+H)$^+$.

Example 35

H-Glu-Val-Leu-Pns-OH (42)

Using Fmoc-Pns Clt resin (0.582 mmol/g) as a starting resin, the title compound was synthesized according to the aforementioned procedure. The resulting crude product was purified using preparative HPLC to obtain the objective product as a white powder.

Yield, 39%; purity, >98% by analytical HPLC (Rt, 15.80 min); TOF-MS m/z: 537.64 (M+H)$^+$.

Example 36

H-Val-Leu-Pns-Asp-Ala-Glu-Phe-OH (43)

Using Fmoc-Phe Wang resin (0.520 mmol/g) as a starting resin and compound 7, the title compound was synthesized according to the aforementioned procedure. The resulting crude product was purified using preparative HPLC to obtain the objective product as a white powder.

Yield, 61%; purity, >98% by analytical HPLC (Rt, 21.15 min); TOF-MS m/z: 871.05 $(M+H)^+$.

Example 37

H-Leu-Pns-Asp-Ala-Glu-Phe-OH (44)

Using Fmoc-Phe Wang resin (0.520 mmol/g) as a starting resin and compound 7, the title compound was synthesized according to the aforementioned procedure. The resulting crude product was purified using preparative HPLC to obtain the objective product as a white powder.

Yield, 49%; purity, >98% by analytical HPLC (Rt, 18.03 min); TOF-MS m/z: 771.66 $(M+H)^+$.

Example 38

H-Pns-Asp-Ala-Glu-Phe-OH (45)

Using Fmoc-Phe Wang resin (0.520 mmol/g) as a starting resin and compound 7, the title compound was synthesized according to the aforementioned procedure. The resulting crude product was purified using preparative HPLC to obtain the objective product as a white powder.

Yield, 49%; purity, >98% by analytical HPLC (Rt, 16.12 min); TOF-MS m/z: 658.53 $(M+H)^+$.

Example 39

H-Gly-Val-Leu-Pns-Asp-Ala-Glu-Phe-OH (46)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 78%; purity, >98% by analytical HPLC (Rt, 18.68 min); TOF-MS m/z: 928.11 $(M+H)^+$.

Example 40

H-Glu-Gly-Leu-Pns-Asp-Ala-Glu-Phe-OH (47)

Using Fmoc-Phe Wang resin (0.520 mmol/g) as a starting resin and compound 7, the title compound was synthesized according to the aforementioned procedure. The resulting crude product was purified using preparative HPLC to obtain the objective product as a white powder.

Yield, 61%; purity, >98% by analytical HPLC (Rt, 18.88 min); TOF-MS m/z: 957.97 $(M+H)^+$.

Example 41

H-Glu-Val-Gly-Pns-Asp-Ala-Glu-Phe-OH (48)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 48%; purity, >98% by analytical HPLC (Rt, 16.90 min); TOF-MS m/z: 943.89 $(M+H)^+$.

Example 42

H-Glu-Val-Leu-Pns-Gly-Ala-Glu-Phe-OH (49)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 63%; purity, >98% by analytical HPLC (Rt, 18.84 min); TOF-MS m/z: 942.05 $(M+H)^+$.

Example 43

H-Glu-Val-Leu-Pns-Asp-Gly-Glu-Phe-OH (50)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 44%; purity, >98% by analytical HPLC (Rt, 18.22 min); TOF-MS m/z: 986.04 $(M+H)^+$.

Example 44

H-Glu-Val-Leu-Pns-Asp-Ala-Gly-Phe-OH (51)

Using Fmoc-Phe Wang resin (0.520 mmol/g) as a starting resin, and compound 7, the title compound was synthesized according to the aforementioned procedure. The resulting crude product was purified using preparative HPLC to obtain the objective product as a white powder.

Yield, 40%; purity, >98% by analytical HPLC (Rt, 19.21 min); TOF-MS m/z: 928.13 $(M+H)^+$.

Example 45

H-Glu-Val-Leu-Pns-Asp-Ala-Glu-Gly-OH (52)

Using Fmoc-Phe Wang resin (0.462 mmol/g) as a starting resin, and compound 7, the title compound was synthesized according to the aforementioned procedure. The resulting crude product was purified using preparative HPLC to obtain the objective product as a white powder.

Yield, 35%; purity, >98% by analytical HPLC (Rt, 15.66 min); TOF-MS m/z: 909.92 $(M+H)^+$.

Example 46

Boc-Pns-NH-Bzl (54)

To a solution of Boc-Pns-OH (650mg, 2.2 mmol) in DMF, were added HOBt.$H_2O$ (337 mg, 2.2 mmol), EDC.HCl (422 mg, 2.2 mmol) and benzylamine (219 μL, 2.0 mmol), and the mixture was stirred overnight. The reaction solution was concentrated under reduced pressure. The residue was dissolved in AcOEt and was washed with 10% citric acid, 5% $NaHCO_3$ and brine, and dried over anhydrous $MgSO_4$. The solvent was concentrated under reduced pressure to obtain the objective product as a white solid.

Yield, 799 mg (104%); mp, 138-140° C.; $^1$H NMR (DMSO-d$_6$) δ (ppm); 1.30 (s, 9H), 2.62-2.84 (m, 2H), 3.87 (m, 1H), 3.99 (m, 1H), 4.21-4.34 (m, 2H), 5.81 (d, 1H, J=6.0 Hz), 6.19 (d, 1H, J=9.0 Hz), 7.17-7.29 (m, 10H); HRMS (FAB$^+$) Calcd for C$_{22}$H$_{29}$N$_2$O$_4$ 385.2127 (M+H)$^+$. Found 385.2134.

Example 47

Boc-Leu-Pns-NH-Bzl (55)

The compound 54 (385 mg, 1.0 mmol) of Example 46 was dissolved in 4 N HCl/dioxane (3.0 mL), and the mixture was stirred at room temperature for 1 hour. The reaction mixture was concentrated under reduced pressure, and the residue was precipitated with ether to obtain a hydrochloride. The hydrochloride was dissolved in a DMF solution, and neutralized with TEA (140 μL, 1.0 mmol). Thereto were added HOBt.H$_2$O (169 mg, 1.1 mmol), Boc-Leu-OH.H$_2$O (274 mg, 1.1 mmol), and EDC.HCl (211 mg, 1.1 mmol), and the mixture was stirred overnight. The reaction solution was concentrated under reduced pressure, and the residue was dissolved in AcOEt. The solution was washed with 10% citric acid, 5% NaHCO$_3$, and brine, and dried over anhydrous MgSO$_4$. The residue was concentrated under reduced pressure to obtain the objective product as a white solid.

Yield, 507 mg (102%); mp, 151-154° C.; $^1$H NMR (DMSO-d$_6$) δ (ppm); 0.87 and 0.81 (each d, each 3H, J=6.6 Hz), 1.23-1.55 (m, 3H), 1.36 (s, 9H), 2.56-2.63 (m, 1H), 2.83 (dd, 1H, J=6.6, 13 Hz, ), 3.85 (m, 1H), 4.16 (dd, 1H, J=6.6, 15 Hz), 4.22 (m, 1H), 4.33 (dd, 1H, J=6.6, 15 Hz), 6.16 (d, 1H, J=6.0 Hz), 6.96 (d, 1H, J=9.0 Hz), 7.20-7.28 (m, 10H), 7.44 (d, 1H, J=9.3 Hz); HRMS (FAB$^+$) Calcd for C$_{28}$H$_{40}$N$_3$O$_5$ 498.2964 (M+H)$^+$. Found 498.2968.

Example 48

Boc-Val-Leu-Pns-NH-Bzl (56)

Using compound 55 of Example 47 and Boc-Val-OH, the title compound was synthesized in the same method as that for compound 55.

Yield, 94%; mp, 219-222° C.; $^1$H NMR (DMSO-d$_6$) δ (ppm); 0.76 and 0.82 (m, 13H), 1.36 (s, 9H), 1.49-1.61 (m, 1H), 1.81-2.00 (m, 1H), 2.66-2.68 (m, 1H), 2.76-2.83 (m, 1H), 3.72-3.90 (m, 2H), 4.11-4.36 (m, 4H), 6.09 (m, 1H), 6.76 (d, 1H, J=9.0 Hz), 7.18-7.28 (m, 10H), 7.56 (d, 1H, J=9.0 Hz), 7.80 (d, 1H, J=9.0 Hz); HRMS (FAB$^+$) Calcd for C$_{33}$H$_{49}$N$_4$O$_6$ 597.3652 (M+H)$^+$. Found 597.3655.

Example 49

H-Glu-Val-Leu-Pns-NH-Bzl (57, KMI-205)

Compound 56 (119 mg, 0.20 mmol) of Example 48 was dissolved in 4 N HCl/dioxane, and the solution was stirred at room temperature for 1 hour. The reaction solution was concentrated under reduced pressure, and the residue was precipitated with ether to obtain a hydrochloride. This hydrochloride was dissolved in a DMF solution and neutralized with TEA (28.0 μL, 0.20 mmol). Then HOBt.H$_2$O (33.7 mg, 0.22 mmol), Z-Glu (OtBu)-OH (74.2 mg, 0.22 mmol) and EDC.HCl (42.2 mg, 0.22 mmol) were added thereto, and the mixture was stirred overnight. The reaction solution was concentrated under reduced pressure, the residue was dissolved in AcOEt. The solution was washed with 10% citric acid, 5% NaHCO$_3$, and brine, and dried over anhydrous MgSO$_4$. The solvent was concentrated under reduced pressure, and the residue was crystallized from ether to obtain white crystals. The crystals were added to thioanisole (100 μL), and the mixture was dissolved in TFA (1.9 mL), followed by stirring at room temperature for 3 hours. The solvent was concentrated under reduced pressure, and the residue was crystallized from ether to obtain a crude product. A part thereof was purified with preparative HPLC to obtain the objective product as a white powder.

Yield, 5.5 mg (23%); mp, 147-150° C.; Rt, 24.68 min; $^1$H NMR (DMSO-d$_6$) δ (ppm); 0.76-0.87 (m, 13H), 1.23-1.49 (m, 3H), 1.81-2.00 (m, 2H), 2.26-2.31 (m, 2H), 2.61-2.83 (m, 2H), 3.81-3.90 (m, 2H), 4.12-4.35 (m, 5H), 6.09 (m, 1H), 7.18-7.26 (m, 10 H), 7.52 (d, 1H, J=9.0 Hz), 8.10-8.22 (m, 2H), 8.45 (d, 1H, J=9.0 Hz); HRMS (FAB$^+$) Calcd for C$_{33}$H$_{48}$N$_5$O$_7$ 626.3554 (M+H)$^+$. Found 626.3547.

Example 50

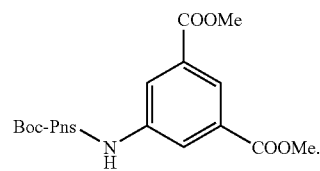

(58)

To a solution of Boc-Pns-OH (500 mg, 1.7 mmol) in DMF, were added 5-aminoisophthalic acid dimethyl ester (354 mg, 1.7 mmol), HOBt.H$_2$O (285 mg, 1.9 mmol), and EDC.HCl (357 mg, 1.9 mmol), and the mixture was stirred overnight. The reaction solution was concentrated under reduced pressure, and the residue was dissolved in AcOEt. The solution was washed with 10% citric acid, 5% NaHCO$_3$, and brine, and dried over anhydrous Na$_2$SO$_4$. The solvent was concentrated under reduced pressure to obtain the objective product as a white solid.

Yield, 786 mg (95%); mp, 180-183° C.; $^1$H NMR (DMSO-d$_6$) δ (ppm); 1.19 (s, 9H), 2.70-2.89 (m, 2H), 3.88 (s, 6H), 4.01-4.10 (m, 2H), 5.86 (d, 1H, J=6.0 Hz), 6.42 (d, 1H, J=9.6 Hz), 7.19-7.29 (m, 5H), 8.16 (s, 1H), 8.57 (m, 2H); HRMS (FAB$^+$) Calcd for C$_{25}$H$_{30}$N$_2$O$_8$Na 509.1900 (M+Na)$^+$. Found 509.1905.

Example 51

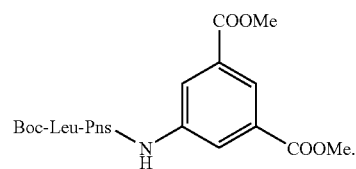

(59)

Compound 58 (786 mg, 1.6 mmol) of Example 50 was added to anisole (211 μL, 1.9 mmol), and the mixture was dissolved in 4 N HCl/dioxane (8.0 mL). The solution was stirred at room temperature for 1 hour. The reaction solution was concentrated under reduced pressure, and the residue was precipitated with ether to obtain a hydrochloride. The hydrochloride was dissolved in a DMF solution, and the solution was neutralized with TEA (225 μL, 1.6 mmol), and Boc-Leu-OH.H₂O (374 mg, 1.6 mmol). HOBt.H₂O (272 mg, 1.8 mmol), and EDC.HCl (341 mg, 1.8 mmol) were added thereto, followed by stirring overnight. The reaction solution was concentrated under reduced pressure, and the residue was dissolved in AcOEt. The solution was washed with 10% citric acid, 5% NaHCO₃, and brine, and dried with anhydrous Na₂SO₄. The solvent was concentrated under reduced pressure, and this was crystallized with ether to obtain the objective product as white crystals.

Yield, 865 mg (89%); mp, 208-209° C.; $^1$H NMR (DMSO-d₆) δ (ppm); 0.58 (dd, 6H, J=6.0, 25 Hz), 1.07-1.12 (m, 2H), 1.30 (brs, 1H), 1.34 (s, 9H), 2.69-2.94 (m, 2H), 3.84-3.87 (m, 7H), 3.99 (s, 1H), 4.32 (d, 1H, J=7.8 Hz), 6.35 (d, 1H, J=4.8 Hz), 6.78 (d, 1H, J=8.4 Hz), 7.22-7.27 (m, 5H), 7.59 (d, 1H, J=9.3 Hz), 8.16 (s, 1H), 8.60 (s, 2H); HRMS (FAB⁺) Calcd for $C_{31}H_{42}N_3O_9$ 600.2921 (M+H)⁺. Found 600.2914.

Example 52

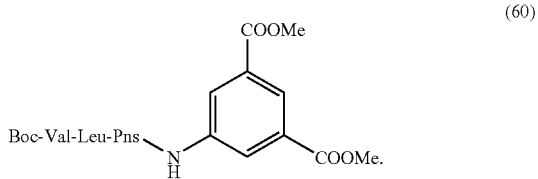

(60)

Using compound 59 of Example 51 and Boc-Val-OH, the title compound was synthesized in the same method as that for compound 59 of Example 51.

Yield, 95%; mp, 118-122° C.; $^1$H NMR (DMSO-d₆) δ (ppm); 0.54 (dd, 6H, J=6.6, 32 Hz), 0.74-0.78 (m, 6H), 1.11-1.23 (m, 2H), 1.37 (s, 9H), 1.46 (s, 1H), 1.86-1.91 (m, 1H), 2.70-2.92 (m, 2H), 3.71-3.76 (m, 1H), 3.87 (s, 6H), 3.96 (d, 1H, J=3.6 Hz), 4.32-4.37 (m, 2H), 6.29 (d, 1H, J=5.7 Hz), 6.72 (d, 1H, J=8.7 Hz), 7.18-7.32 (m, 5H), 7.65 (d, 1H, J=8.4 Hz), 7.81 (d, 1H, J=8.7 Hz), 8.15-8.16 (m, 1H), 8.59-8.60 (m, 2H); HRMS (FAB⁺) Calcd for $C_{36}H_{51}N_4O_{10}$ 699.3605 (M+H)⁺. Found 699.3610.

Example 53

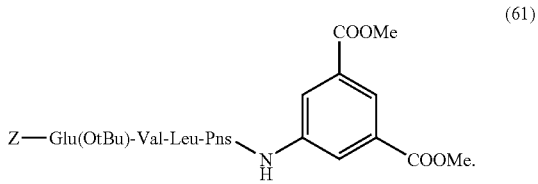

(61)

Using compound 60 of Example 52 and Z-Glu (OtBu)-OH, the title compound was synthesized according to the same manner as that of compound 59 of Example 51.

Yield, 73%; mp, 225-228° C.; $^1$H NMR (DMSO-d₆) δ (ppm); 0.54 (dd, 6H, J=6.3, 25 Hz), 0.76 (d, 6H, J=6.3 Hz), 1.12-1.14 (m, 2H), 1.26-1.42 (m, 1H), 1.36 (s, 9H), 1.69-1.87 (m, 3H), 2.20 (t, 2H, J=7.6 Hz), 2.72-2.92 (m, 2H), 3.87 (s, 6H), 3.96 (d, 1H, J=5.7 Hz), 4.04-4.15 (m, 2H), 4.31 (t, 2H, J=7.5 Hz), 5.01 (s, 2H), 6.29 (d, 1H, J=5.4 Hz), 7.20-7.33 (m, 10H), 7.47 (d, 1H, J=8.1 Hz), 7.70-7.73 (m, 2H), 7.91 (d, 1H, J=8.1 Hz), 8.16 (s, 1H), 8.59 (s, 2H); HRMS (FAB⁺) Calcd for $C_{48}H_{63}N_5O_{13}Na$, 940.4320; (M+Na)⁺. Found 940.4311.

Example 54

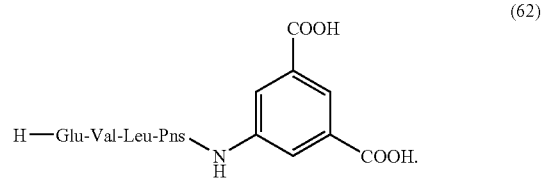

(62)

Compound 61 (76.5 mg, 0.083 mmol) of Example 53 was dissolved in MeOH, and 4N NaOH (208 µL, 0.83 mmol) was added thereto under ice-cooling, followed bt stirring at room temperature overnight. The reaction solution was acidified with citric acid, and concentrated under reduced pressure. The residue was dissolved in AcOEt, washed with 10% citric acid and brine, and dried over anhydrous Na₂SO₄. The solvent was concentrated under reduced pressure, thioanisole (100 µL) was added to the residue, and the mixture was dissolved again in TFA (5.0 mL), followed by stirring. After 6 hours, the reaction solution was concentrated under reduced pressure, and the residue was crystallized from ether to obtain a crude product. A part thereof was purified by preparative HPLC to obtain the objective product as a white powder.

Yield, 6.6 mg (11%); mp, 198-203° C.; Rt, 18.74 min; $^1$H NMR (DMSO-d₆) δ (ppm); 0.47 (dd, 6H, J=6.3, 28 Hz), 0.82 (d, 6H, J=6.9 Hz), 1.11-1.23 (m, 3H), 1.86-1.91 (m, 3H), 2.27 (t, 2H, J=8.1 Hz), 2.72-2.92 (m, 2H), 3.85 (t, 1H, J=6.0 Hz), 3.96 (brs, 1H), 4.17 (t, 1H, 7.8 Hz), 4.32-4.34 (m, 2H), 6.28 (brs, 1H), 7.20-7.29 (m, 5H), 7.79 (d, 1H, J=9.0 Hz), 8.04 (d, 1H, J=8.1 Hz), 8.14 (s, 1H), 8.39 (d, 1H, J=8.4 Hz), 8.50 (s, 2H); HRMS (FAB⁺) Calcd for $C_{34}H_{46}N_5O_{11}$ 700.3194 (M+H)⁺. Found 700.3188.

Example 55

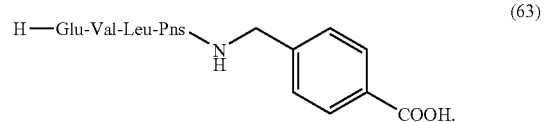

(63)

Using Fmoc-NH—CH₂—C₆H₄—CO-Clt resin (0.492 mmol/g) as a starting resin, and compound 7, the title compound was synthesized according to the aforementioned procedure. The resulting crude product was purified using preparative HPLC to obtain the objective product as a white powder.

Yield, 52%; purity, >98% by analytical HPLC (Rt, 19.05 min); TOF-MS m/z: 670.70 (M+H)⁺.

Example 56

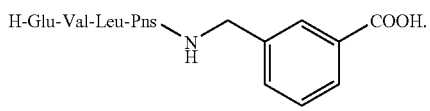
(64)

Using Fmoc-NH—CH$_2$—C$_6$H$_4$—CO-Clt resin (0.606 mmol/g) as a starting resin, and compound 7, the title compound was synthesized according to the aforementioned procedure. The resulting crude product was purified using preparative HPLC to obtain the objective product as a white powder.

Yield, 76%; purity, >98% by analytical HPLC (Rt, 19.44 min); TOF-MS m/z: 670.77 (M+H)$^+$.

Example 57

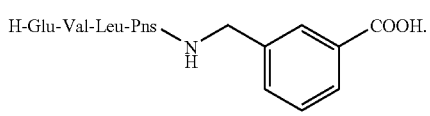
(65)

Using Fmoc-NH—C$_6$H$_4$—CO-Clt resin (0.612 mmol/g) as a starting resin, and compound 7, the title compound was synthesized according to the aforementioned procedure. The resulting crude product was purified using preparative HPLC to obtain the objective product as a white powder.

Yield, 56%; purity, >98% by analytical HPLC (Rt, 19.91 min); TOF-MS m/z: 656.73 (M+H)$^+$.

Example 58

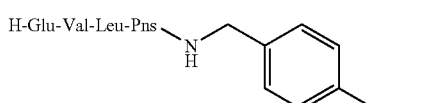
(66)

Using Fmoc-NH—C$_6$H$_4$—CO-Clt resin (0.505 mmol/g) as a starting resin, and compound 7, the title compound was synthesized according to the aforementioned procedure. The resulting crude product was purified using preparative HPLC to obtain the objective product as a white powder.

Yield, 45%; purity, >98% by analytical HPLC (Rt, 19.95 min); TOF-MS m/z: 656.74 (M+H)$^+$.

Example 59 glt-Val-Leu-Pns-Asp-Ala-Gly-Phe-OH (67)

Using Fmoc-Glu (OtBu) Wang resin (0.560 mmol/g) as a starting resin, compound 7 and gultaric anhydride, the title compound was synthesized according to the aforementioned procedure. The resulting crude product was purified using preparative HPLC to obtain the objective product as a white powder.

Yield, 22%; purity, >98% by analytical HPLC (Rt, 19.94 min); TOF-MS m/z: 959.81 (M+Na)$^+$.

Example 60

H-Gln-Val-Leu-Pns-Asp-Ala-Gly-Phe-OH (68)

Using Fmoc-Glu (OtBu) Wang resin (0.560 mmol/g) as a starting resin, and compound 7, the title compound was synthesized according to the aforementioned procedure. The resulting crude product was purified using preparative HPLC to obtain the objective product as a white powder.

Yield, 47%; purity, >98% by analytical HPLC (Rt, 16.82 min); TOF-MS m/z: 851.81 (M+H)$^+$.

Example 61

H-Asp-Val-Leu-Pns-Asp-Ala-Gly-Phe-OH (69)

Using Fmoc-Glu (OtBu) Wang resin (0.560 mmol/g) as a starting resin, and compound 7, the title compound was synthesized according to the aforementioned procedure. The resulting crude product was purified using preparative HPLC to obtain the objective product as a white powder.

Yield, 32%; purity, >98% by analytical HPLC (Rt, 17.82 min); TOF-MS m/z: 834.00 (M+H)$^+$.

Example 62

H-homoGlu-Val-Leu-Pns-Asp-Ala-Gly-Phe-OH (70)

Using Fmoc-Glu (OtBu) Wang resin (0.560 mmol/g) as a starting resin, compound 7 and Fmoc-homoGlu(OtBu)-OH[21], the title compound was synthesized according to the aforementioned procedure. The resulting crude product was purified using preparative HPLC to obtain the objective product as a white powder.

Yield, 22%; purity, >98% by analytical HPLC (Rt, 17.67 min); TOF-MS m/z: 866.94 (M+H)$^+$.

Example 63

β-ODap-Val-Leu-Pns-Asp-Ala-Gly-Phe-OH (71)

Using Fmoc-Glu (OtBu) Wang resin (0.560 mmol/g) as a starting resin, compound 7, Boc-Dap (Fmoc)-OH and 2-(tert-butoxy)-2-oxoacetic acid[22], the title compound was synthesized according to the aforementioned procedure. The resulting crude product was purified using preparative HPLC to obtain the objective product as a white powder.

Yield, 18%; purity, >98% by analytical HPLC (Rt, 17.39 min); TOF-MS m/z: 881.82 (M+H)$^+$.

Example 64

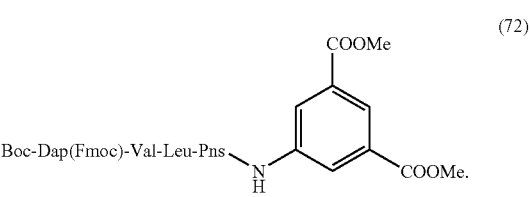
(72)

Using compound 60 of Example 52 and Boc-Dap (Fmoc)-OH, the title compound was synthesized in the same method as that for compound 59 of Example 51.

Yield, 84%; mp, 198-202° C.; $^1$H NMR (DMSO-d$_6$) δ (ppm); 0.53 (dd, 6H, J=6.6, 26 Hz), 0.77 (t, 6H, J=6.3 Hz), 1.07-1.20 (m, 2H), 1.33 (brs, 1H), 1.36 (s, 9H), 1.88-1.99 (m, 1H), 2.70-2.91 (m, 2H), 3.26 (brs, 2H), 3.90 (s, 6H), 3.97 (d, 1H, J=4.2 Hz), 4.01-4.07 (m, 1H), 4.18-4.31 (m, 6H), 6.30 (d, 1H, J=5.4 Hz), 6.99 (d, 1H, J=7.8 Hz), 7.21 (d, 1H, J=8.4 Hz), 7.25-7.42 (m, 9H), 7.58 (d, 1H, J=8.1 Hz), 7.67 (d, 2H, J=7.2 Hz), 7.74 (d, 1H, J=8.4 Hz), 7.88 (d, 2H, J=7.5 Hz), 7.94 (d, 1H, J=8.1 Hz), 8.15 (s, 1H), 8.59 (s, 2H); HRMS (FAB$^+$) Calcd for $C_{54}H_{67}N_6O_{13}$ 1007.4766 (M+H)$^+$. Found 1007.4760.

Example 65

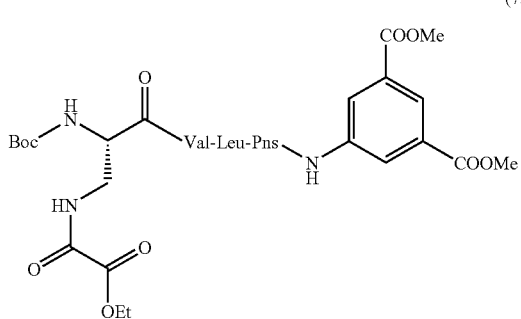

(73)

Compound 72 (60.0 mg, 0.060 mmol) of Example 64 was dissolved in 20% diethylamine/DMF, and the mixture was stirred at room temperature for 20 minutes, and concentrated under reduced pressure. The residue was dissolved in AcOEt, and the solution was washed with 5% NaHCO$_3$, and brine, and dried over anhydrous Na$_2$SO$_4$. The solvent was concentrated under reduced pressure, and the residue was dissolved in DMF again. TEA (16.6 µL, 0.12 mmol) and chloroformic acid ethyl ester (14.5 µL, 0.13 mmol) were added thereto, and the mixture was stirred at room temperature overnight. The reaction solution was concentrated under reduced pressure, and the residue was crystallized from ether to obtain the objective product as a white crystal.

Yield, 64.7 mg (123%); mp, 143-148° C.; $^1$H NMR (DMSO-d$_6$) δ (ppm); 0.53 (dd, 6H, J=6.3, 24 Hz), 0.75 (t, 6H, J=6.0 Hz), 1.16-1.36 (m, 15H), 1.87-1.93 (m, 1H), 2.73-2.89 (m, 4H), 3.87 (s, 6H), 3.96-3.97 (m, 1H), 4.11-4.23 (m, 4H), 4.30 (t, 2H, J=8.1 Hz), 6.36 (d, 1H, J=5.7 Hz), 7.15 (d, 1H, J=7.8 Hz), 7.23-7.29 (m, 5H), 7.62 (d, 1H, J=7.8 Hz), 7.74 (d, 1H, J=8.7 Hz), 7.94 (d, 1H, J=8.7 Hz), 8.16 (s, 1H), 8.59 (s, 2H), 8.78 (brs, 1H); HRMS (FAB$^+$) Calcd for $C_{43}H_{61}N_6O_{14}$ 885.4246 (M+H)$^+$. Found 885.4243.

Example 66

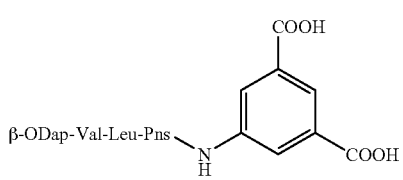

(74)

Compound 73 (34.7 mg, 0.039 mmol) of Example 65 was dissolved in DMF, and 4N NaOH (98.0 µL, 0.39 mmol) was added thereto under ice-cooling, followed by stirring at room temperature overnight. The reaction solution was acidified with citric acid, and concentrated under reduced pressure, and the residue was dissolved in AcOEt. The solution was washed with 10% citric acid, and brine, and dried with anhydrous Na$_2$SO$_4$. The solvent was concentrated under reduced pressure, and anisole (5.11 µL, 0.047 mmol) was added to the residue. The mixture was dissolved in 4N HCl/dioxane (3.0 mL) again, and the solution was stirred. After 1 hour, the reaction solution was concentrated under reduced pressure, and the residue was crystallized from ether to obtain a crude product. A part thereof was purified by preparative HPLC to obtain the objective product as a white powder.

Yield, 3.7 mg (14%); mp, 220-224° C.; Rt, 18.55 min; $^1$H NMR (DMSO-d$_6$) δ (ppm); 0.54 (dd, 6H, J=6.3, 23 Hz), 0.74-0.82 (m, 6H), 1.16-1.23 (m, 3H), 1.90-1.99 (m, 2H), 2.27 (brs, 1H), 2.72-2.89 (m, 2H), 3.96-4.00 (m, 2H), 4.16 (t, 1H, J=7.2 Hz), 4.30 (t, 2H, J=7.5 Hz), 7.21 (d, 1H, J=6.6 Hz), 7.27-7.29 (m, 5H), 7.84 (d, 1H, J=8.7 Hz), 7.98 (d, 1H, J=8.4 Hz), 8.06 (d, 1H, J=8.1 Hz), 8.14 (s, 1H), 8.50 (s, 2H), 8.59 (brs, 1H); HRMS (FAB$^+$) Calcd for $C_{34}H_{45}N_6O_{12}$ 729.3095 (M+H)$^+$. Found 729.3103.

Example 67

Experiment Regarding Measurement of BACE1 Inhibitory Activity

Enzyme Used in Measurement

As an enzyme having β-secretase activity, recombinant human BACE-1 (rhBACE-1) purchased from R&D systems (Minneapolis, Minn.) was used. rhBACE-1 is expressed as only an extracellular region (amino acid 1-460 residues) of recombinant human β-secretase, with a His tag at its carboxyl terminal in murine myeloma cell line, NS0. Purified secreted rhBACE1 is a mixture of a pro entity (about 75 kDa) and a mature entity (about 72 kDa). The purity is >90% (as determined by SDS-PAGE and visualized by silver stain), and enzyme activity is exhibited under the weak acidity (pH 3.5-5.5).

Assessment of Enzyme Inhibitory Activity

Enzyme inhibitory activity of an inhibitor was assessed by quantitating an N-terminal fragment produced aftercleaving the substrate with BACE1 by reverse HPLC using (7-methoxycoumarin-4-yl)acetyl-Ser-Glu-Val-Asn-Leu-Asp-Ala-Glu-Phe-Arg-Lys(2,4-dinitrophenyl)-Arg-Arg-NH$_2$ purchased from Peptide Institute (Osaka, Japan) as a substrate for BACE1. To 40 µL of 62.5 mM 2-(N-morpholino) ethansulfonic acid (MES)-CH$_3$COOH—NaOH buffer (pH 5.0), were added 1 µL of a solution of an inhibitor diluted with DMSO (100 µM), 4 µL of rhBACE-1 (6.25 ng/µL), and 5 µL of an aqueous solution (50% DMSO) of 250 µM substrate (7-methoxycoumarin-4-yl)acetyl-Ser-Glu-Val-Asn-Leu-Asp-Ala-Glu-Phe-Arg-Lys(2,4-dinitrophenyl)-Arg-Arg-NH$_2$ to initiate an enzyme reaction. After incubation at 37° C. for 60 minutes, 20 µL of 20% trichloroacetic acid was added to stop the reaction. And, inhibition % was calculated by measuring a fluorescent intensity of the N-terminal fragment (Ex, 328 nm; Em, 393 nm) using reverse phase HPLC (linear gradient of MeCN in aqueous TFA; flow rate, 1.0 mL/min).

BACE1 Inhibitory Activity

Enzyme inhibitory activity of an inhibitor was assessed by quantitating a N-terminal fragment produced after cleavage of a substrate with BACE1 by reverse phase HPLC using (7-methoxycoumarin-4-yl)acetyl-Ser-Glu-Val-Asn-Leu-Asp-Ala-Glu-Phe-Arg-Lys(2,4-dinitrophenyl)-Arg-Arg-$NH_2$ purchased from Peptide Institute (Osaka, Japan) as a substrate for BACE1. Recombinant human BACE-1 purchased from R&D systems (Minneapolis, Minn.) was used. To 40 μL of 62.5 mM 2-(N-morpholino)ethansulfonic acid (MES)-$CH_3COOH$—NaOH buffer (pH 5.0), were added 1 μL of a solution of an inhibitor diluted with DMSO (100 μM), 4 μL of BACE1 (6.25 ng/μL), and 5 μL of an aqueous solution (50% DMSO) of 250 μM substrate (7-methoxycoumarin-4-yl)acetyl-Ser-Glu-Val-Asn-Leu-Asp-Ala-Glu-Phe-Arg-Lys(2,4-dinitrophenyl)-Arg-Arg-$NH_2$ to initiate an enzyme reaction. After incubation at 37° C. for 60 minutes, 20 μL of 20% trichloroacetic acid was added to stop a reaction. Inhibition % was calculated by measuring a fluorescent intensity of the N-terminal fragment (Ex, 328 nm; Em, 393 nm) using reverse phase HPLC (linear gradient of MeCN in aqueous TFA; flow rate, 1.0 mL/min).

Results are shown in the following table.

TABLE 1

| Example Number | Activity | Example Number | Activity |
|---|---|---|---|
| 127 | 100 | 142 | 89.83 |
| 185 | 100 | 7 | 89.65 |
| 186 | 100 | 76 | 89.49 |
| 187 | 100 | 172 | 89.45 |
| 189 | 100 | 163 | 88.31 |
| 135 | 99.77 | 184 | 88.13 |
| 66 | 99.75 | 77 | 87.92 |
| 134 | 99.56 | 173 | 86.06 |
| 137 | 99.47 | 78 | 85.85 |
| 188 | 99.46 | 79 | 85.32 |
| 136 | 99.43 | 166 | 84.88 |
| 190 | 99.35 | 179 | 83.67 |
| 125 | 99.07 | 58 | 83.67 |
| 126 | 98.93 | 80 | 83.24 |
| 68 | 98.83 | 81 | 82.89 |
| 167 | 98.77 | 181 | 82.52 |
| 177 | 98.50 | 174 | 81.83 |
| 69 | 98.36 | 82 | 81.76 |
| 54 | 98.32 | 57 | 81.46 |
| 70 | 98.31 | 43 | 81.23 |
| 71 | 97.89 | 149 | 80.13 |
| 124 | 97.28 | 83 | 80.13 |
| 63 | 96.66 | 84 | 79.08 |
| 72 | 95.01 | 27 | 78.43 |
| 148 | 93.76 | 156 | 78.28 |
| 73 | 93.01 | 182 | 75.72 |
| 171 | 91.80 | 85 | 75.23 |
| 150 | 90.80 | 86 | 74.98 |
| 74 | 90.52 | 146 | 74.74 |
| 75 | 90.42 | 131 | 74.08 |
| 165 | 73.69 | 26 | 60.23 |
| 178 | 73.43 | 168 | 60.03 |
| 87 | 72.25 | 138 | 59.62 |
| 32 | 71.60 | 147 | 59.46 |
| 162 | 71.54 | 96 | 59.25 |
| 133 | 71.49 | 97 | 59.11 |
| 160 | 71.33 | 98 | 58.41 |
| 88 | 70.42 | 99 | 58.04 |
| 154 | 69.89 | 29 | 57.47 |
| 89 | 69.77 | 130 | 57.22 |
| 155 | 69.70 | 151 | 57.00 |
| 90 | 69.04 | 100 | 56.93 |
| 143 | 68.96 | 42 | 56.72 |
| 91 | 68.90 | 30 | 56.57 |
| 132 | 68.08 | 44 | 56.30 |
| 141 | 67.49 | 101 | 56.12 |
| 45 | 66.79 | 55 | 55.98 |
| 31 | 66.56 | 28 | 55.88 |
| 158 | 66.10 | 103 | 54.60 |
| 153 | 65.79 | 15 | 54.52 |
| 92 | 65.37 | 104 | 54.42 |
| 93 | 64.84 | 105 | 54.04 |
| 161 | 64.74 | 13 | 53.71 |

TABLE 1-continued

| Example Number | Activity | Example Number | Activity |
|---|---|---|---|
| 164 | 64.12 | 128 | 53.57 |
| 56 | 64.05 | 18 | 53.38 |
| 34 | 63.71 | 106 | 52.95 |
| 94 | 61.80 | 183 | 52.15 |
| 95 | 61.66 | 107 | 52.14 |
| 169 | 61.57 | 180 | 51.43 |
| 123 | 61.38 | 108 | 51.32 |
| 129 | 61.04 | 145 | 50.49 |
| 170 | 60.53 | 109 | 50.03 |

Example 68

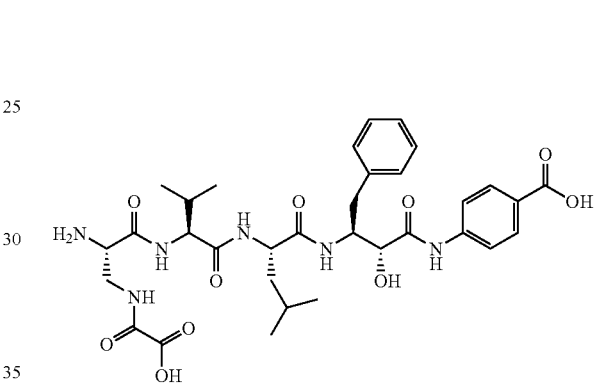

The above compound was prepared in the same manner as in Example 55.

Yield 14.1 mg (68%), TOF-MS: 685.87

Example 69

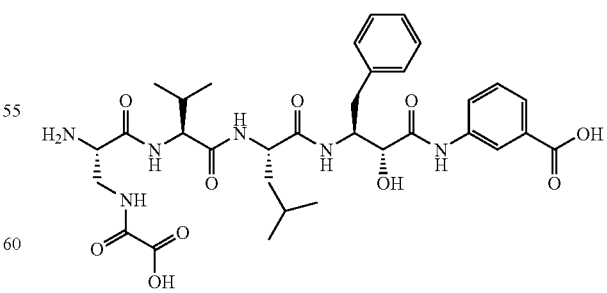

The above compound was prepared in the same manner as in Example 55.

Yield 4.0 mg (46%), TOF-MS: 685.75

Example 70
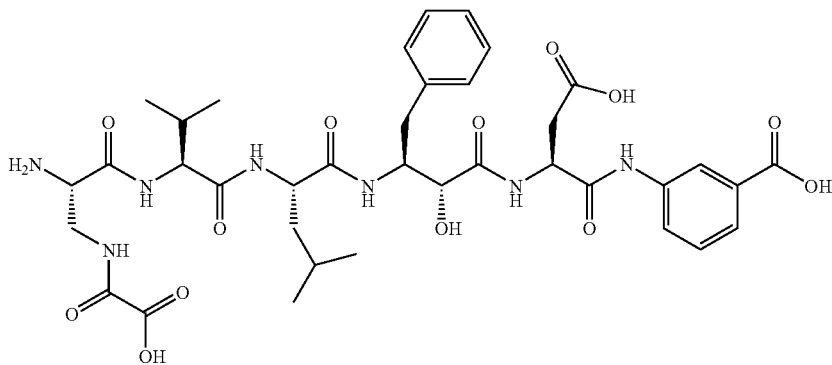
The above compound was prepared in the same manner as in Example 55.
Yield 3.7 mg (37%), TOF-MS: 800.91
Example 71
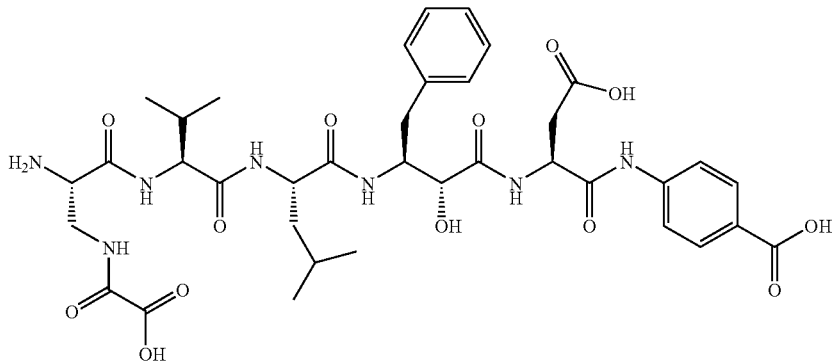
The above compound was prepared in the same manner as in Example 55.
Yield 3.7 mg (19%), TOF-MS: 800.84
Example 72
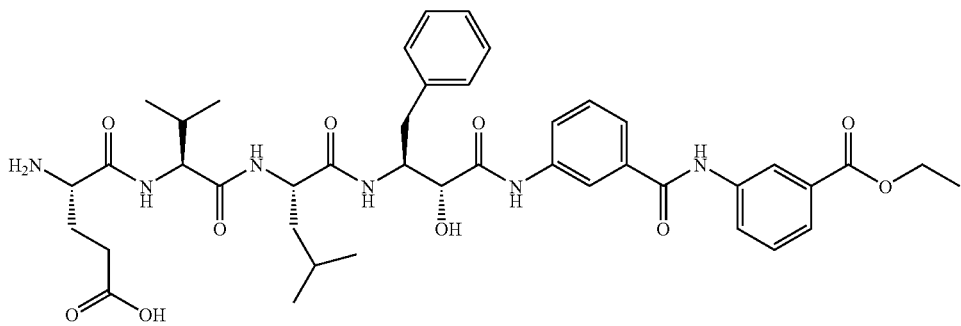
The above compound was prepared in the same manner as in Examples 50-54.
Yield 2.5 mg (5%), TOF-MS: 803.60

Example 73
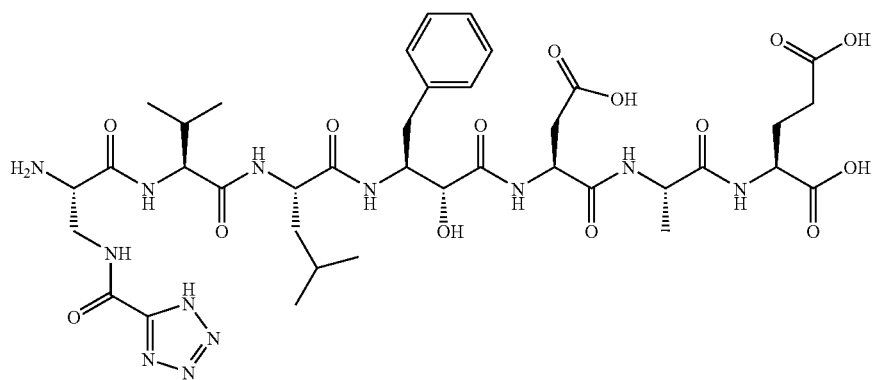
The above compound was prepared in the same manner as in Example 1.
Yield 4.8 mg (14%), TOF-MS: 906.03
Example 74
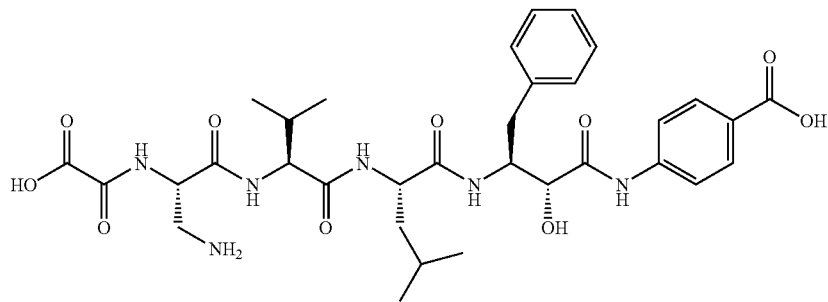
The above compound was prepared in the same manner as in Example 55.
Yield 8.1 mg (31%), TOF-MS: 685.84
Example 75
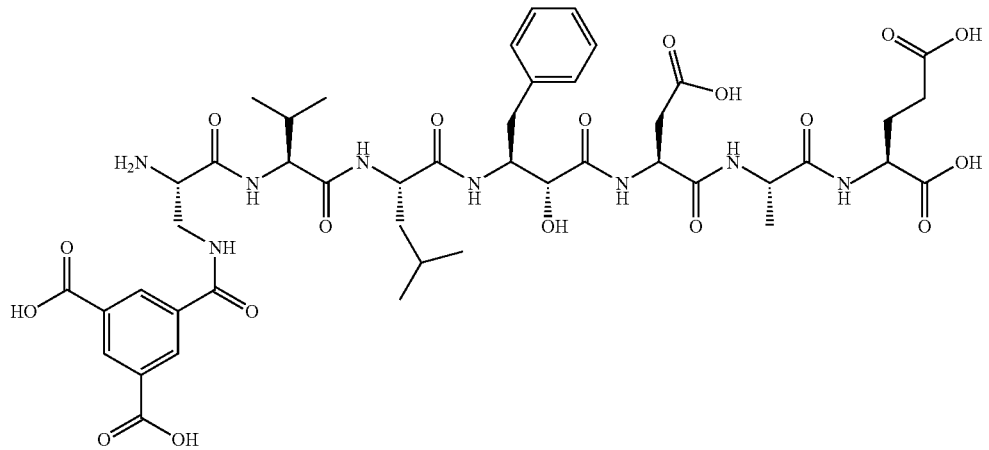

The above compound was prepared in the same manner as in Example 1.
Yield 12.5 mg (42%), TOF-MS: 1002.04
Example 76
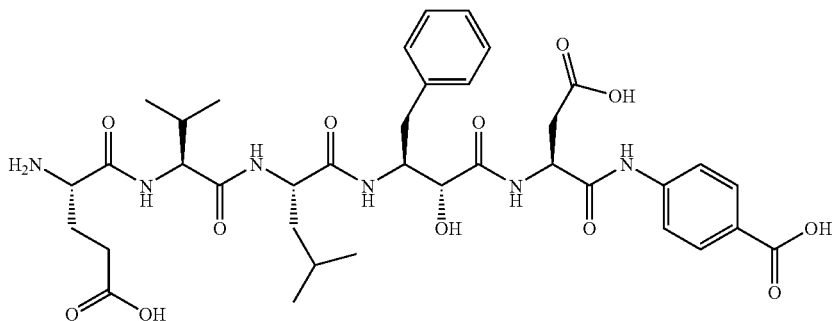
The above compound was prepared in the same manner as in Example 55.
Yield 1.0 mg (4%), TOF-MS: 771.73
Example 77
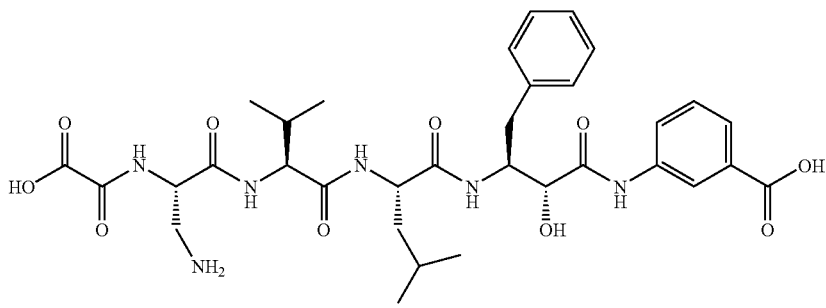
The above compound was prepared in the same manner as in Example 55.
Yield 5.0 mg (58%), TOF-MS: 685.85
Example 78
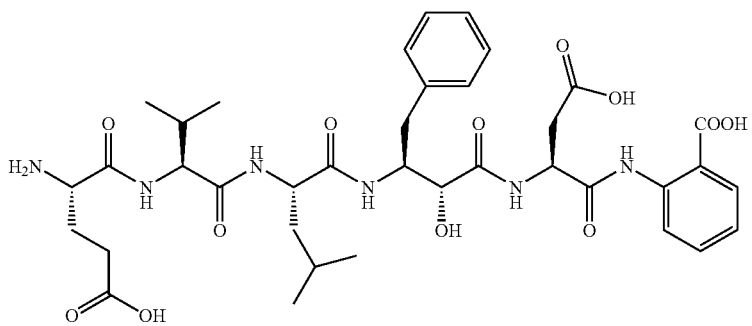
The above compound was prepared in the same manner as in Example 55.
Yield 0.3 mg (1%), TOF-MS: 771.92

Example 79
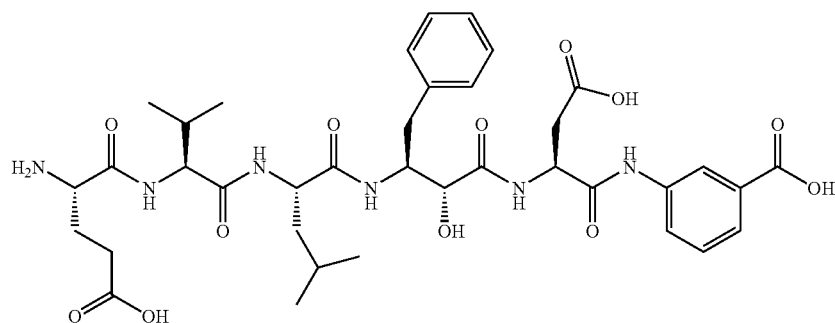
The above compound was prepared in the same manner as in Example 55.
Yield 10.5 mg (32%), TOF-MS: 771.53
Example 80
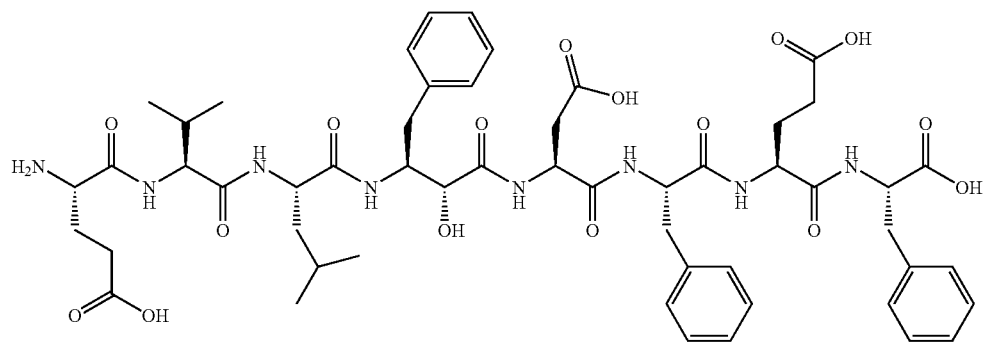
The above compound was prepared in the same manner as in Example 1.
Yield 11.9 mg (48%), TOF-MS: 1076.02

Example 81
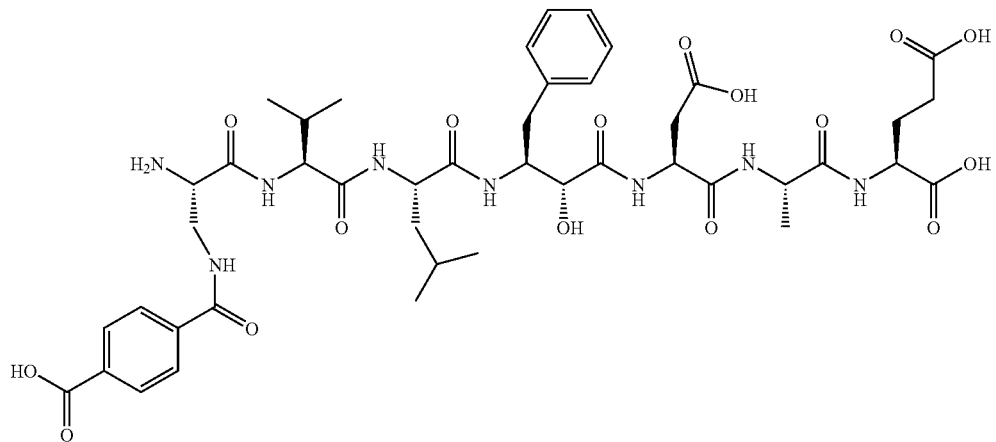
The above compound was prepared in the same manner as in Example 1.
Yield 13.8 mg (39%), TOF-MS: 957.01
Example 82
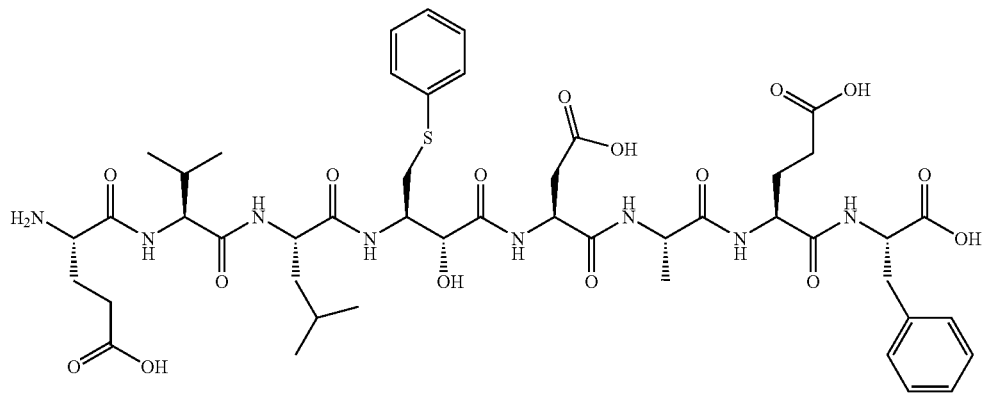
The above compound was prepared in the same manner as in Example 1.
Yield 11.6 mg (26%), TOF-MS: 1032.15

Example 83
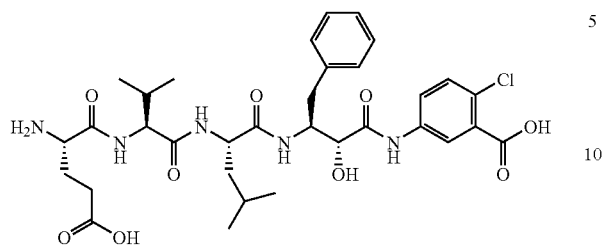
The above compound was prepared in the same manner as in Example 55.
Yield 1.0 mg (8%), TOF-MS: 691.08
Example 84
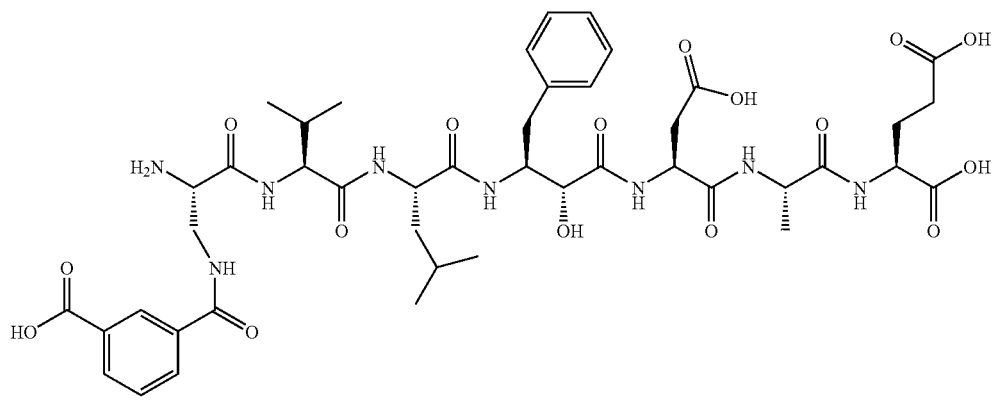
The above compound was prepared in the same manner as in Example 1.
Yield 10.1 mg (24%), TOF-MS: 957.24
Example 85
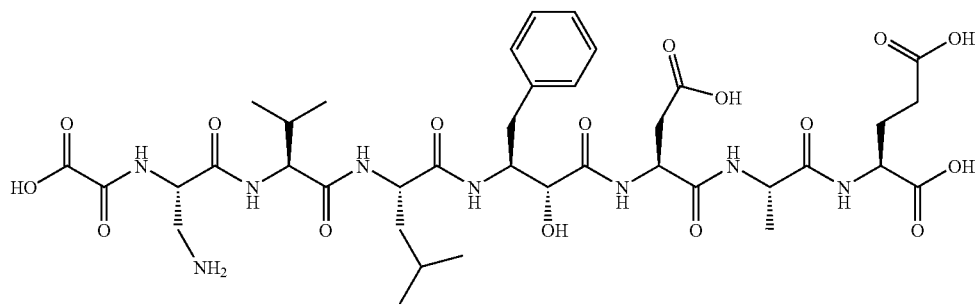
The above compound was prepared in the same manner as in Example 1.
Yield 19.6 mg (52%), TOF-MS: 881.70

Example 86
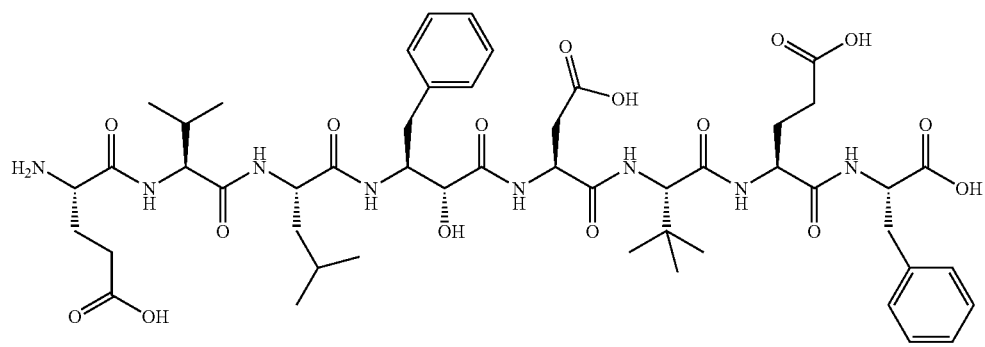
The above compound was prepared in the same manner as in Example 1.
Yield 26.3 mg (28%), TOF-MS: 1042.28
Example 87
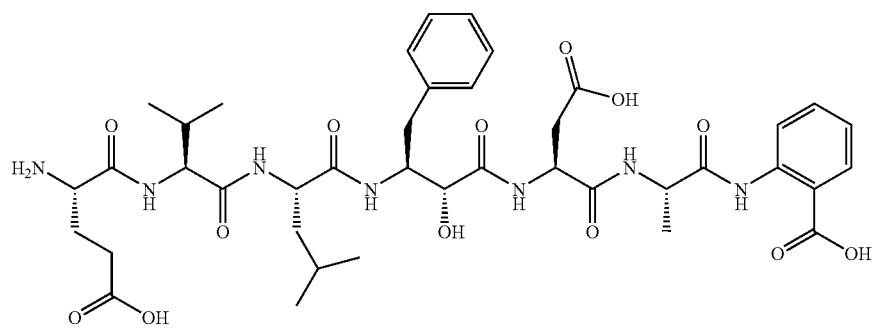
The above compound was prepared in the same manner as in Example 55.
Yield 3.3 mg (4%), TOF-MS: 842.83
Example 88
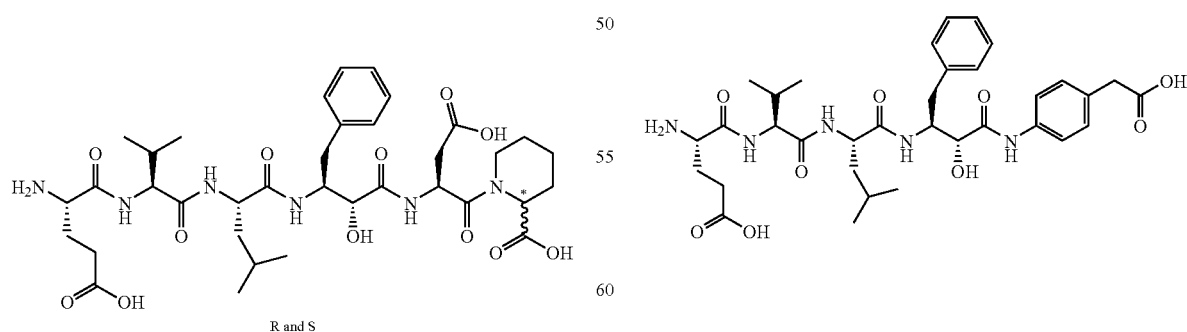
The above compound was prepared in the same manner as in Example 55.
Yield 5.4 mg (12%), TOF-MS: 763.82
Example 89
The above compound was prepared in the same manner as in Example 55.
Yield 18.0 mg (42%), TOF-MS: 670.40

Example 90
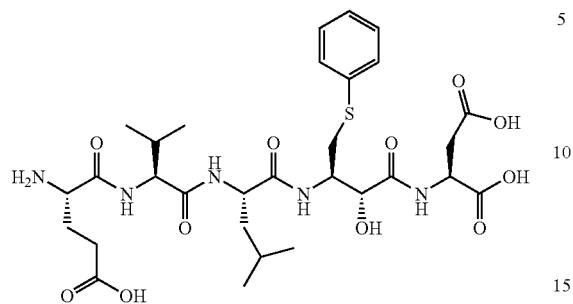
The above compound was prepared in the same manner as in Example 1.
Yield 18.2 mg (52%), TOF-MS: 684.71
Example 91
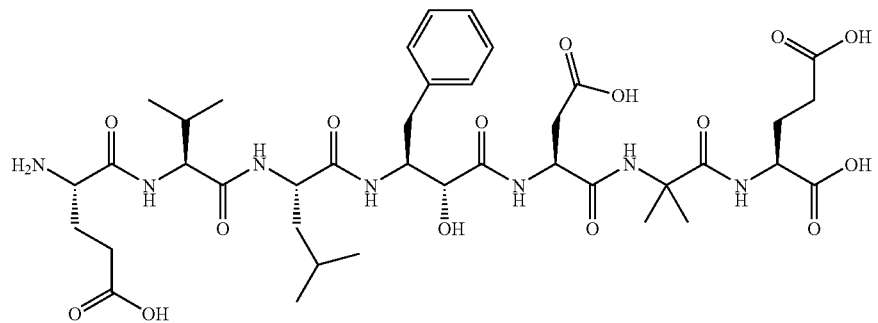
The above compound was prepared in the same manner as in Example 1.
Yield 20.4 mg (39%), TOF-MS: 866.82
Example 92
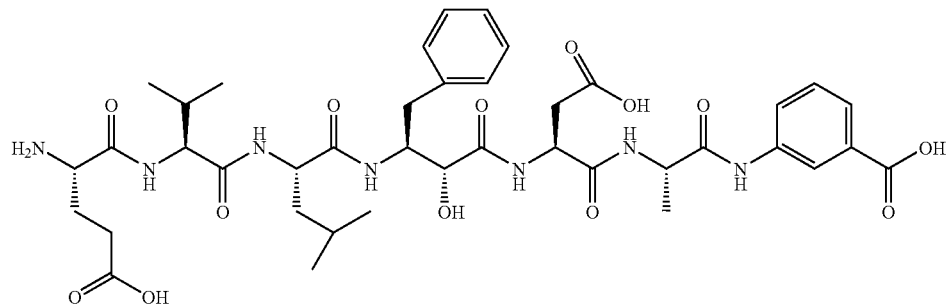
The above compound was prepared in the same manner as in Example 55.
Yield 22.7 mg (67%), TOF-MS: 842.34

Example 93
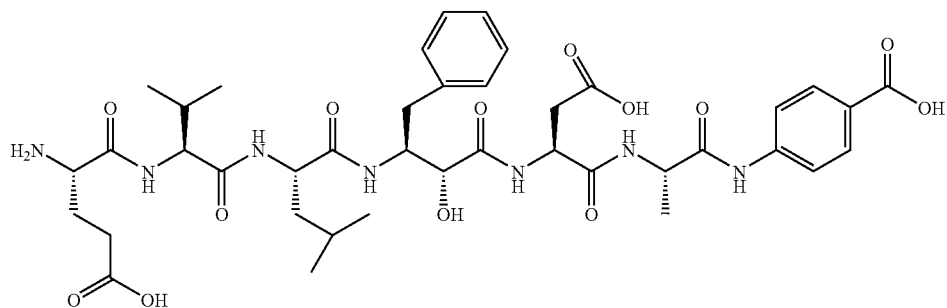
The above compound was prepared in the same manner as in Example 55.
Yield 32.0 mg (79%), TOF-MS: 842.92
Example 94
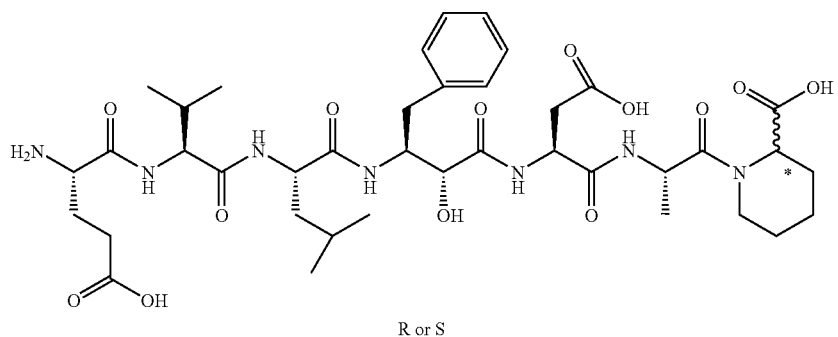
The above compound was prepared in the same manner as in Example 55.
Yield 7.9 mg (19%), TOF-MS: 834.87
Example 95
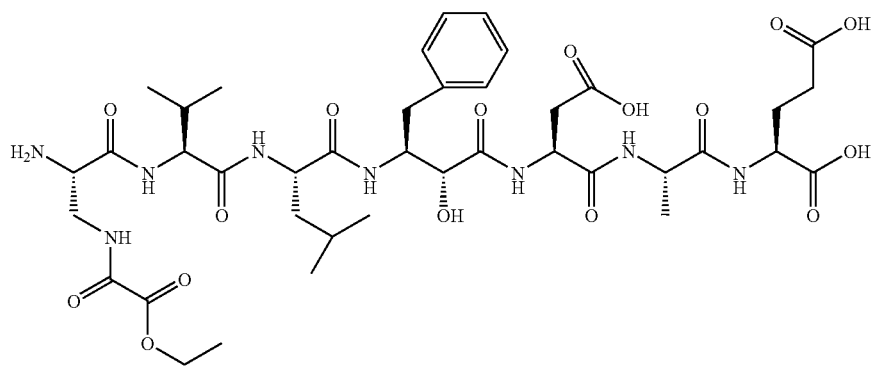
The above compound was prepared in the same manner as in Example 1.
Yield 17.7 mg (33%), TOF-MS: 909.82

Example 96
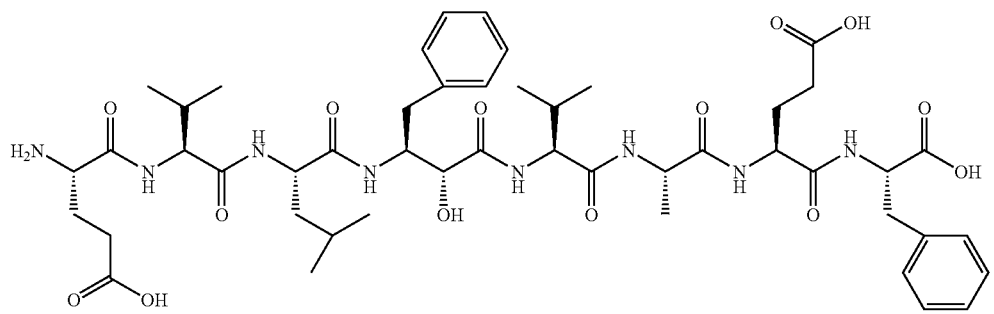
The above compound was prepared in the same manner as in Example 1.
Yield 32.2 mg (51%), TOF-MS: 984.18
Example 97
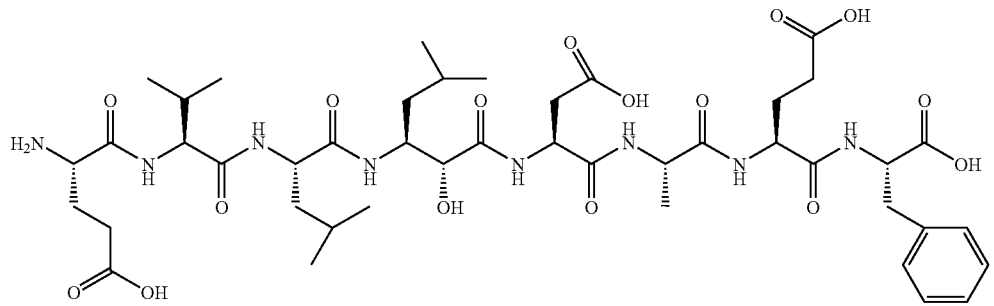
The above compound was prepared in the same manner as in Example 1.
Yield 22.1 mg (48%), TOF-MS: 966.19
Example 98
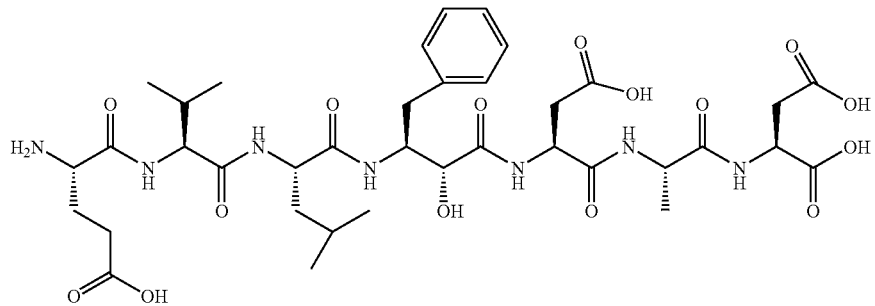
The above compound was prepared in the same manner as in Example 1.
Yield 19.9 mg (60%), TOF-MS: 838.94

Example 99
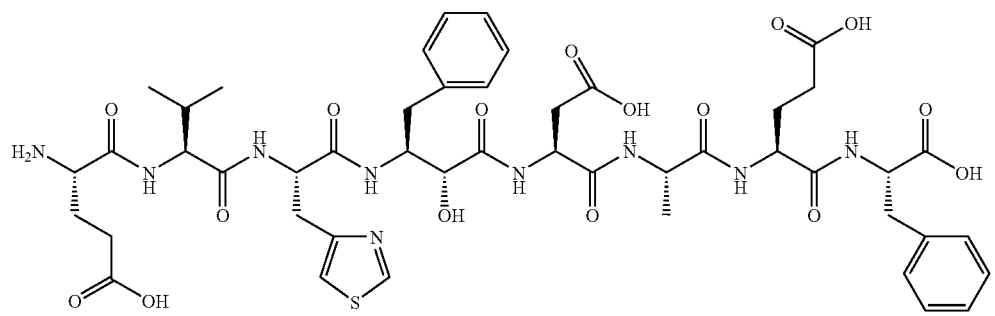
The above compound was prepared in the same manner as in Example 1.
Yield 18.9 mg (34%), TOF-MS: 1041.14
Example 100
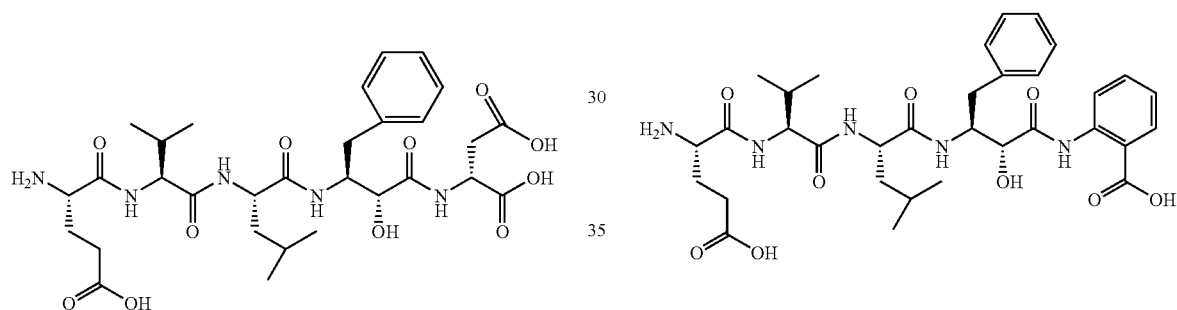
The above compound was prepared in the same manner as in Example 1.
Yield 23.9 mg (65%), TOF-MS: 652.65
Example 101
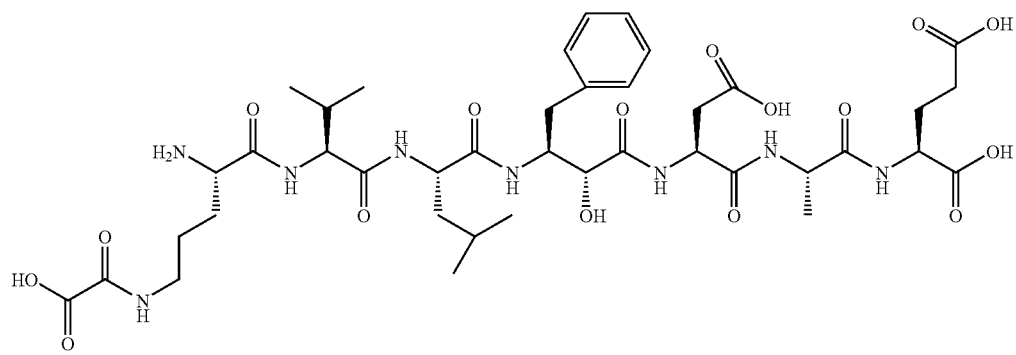
The above compound was prepared in the same manner as in Example 1.
Yield 9.3 mg (24%), TOF-MS: 909.12
Example 102
The above compound was prepared in the same manner as in Example 55.
Yield 3.2 mg (32%), TOF-MS: 656.79

Example 103
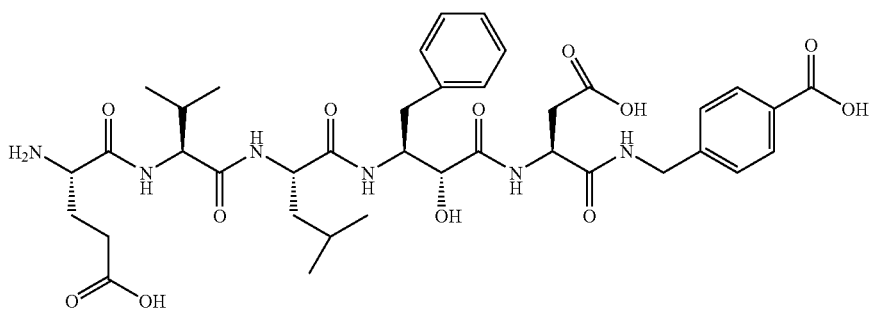
The above compound was prepared in the same manner as in Example 55.
Yield 17.2 mg (32%), TOF-MS: 785.79
Example 104
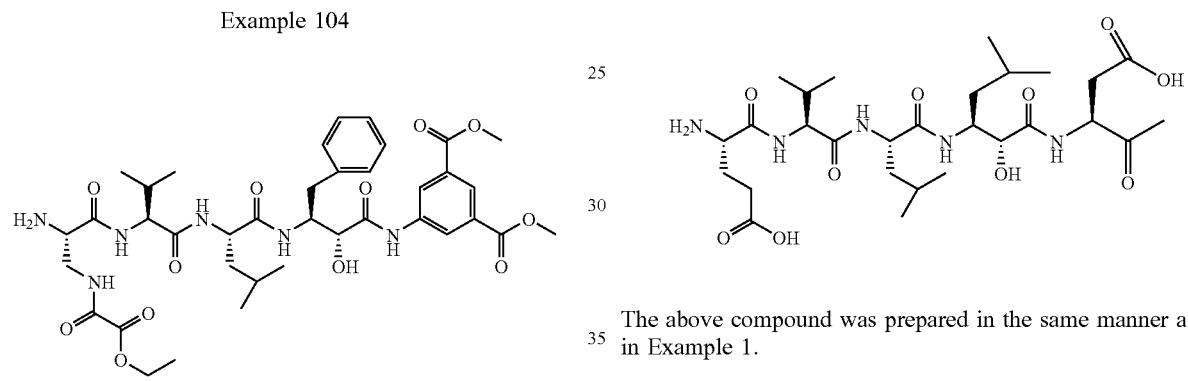
The above compound was prepared in the same manner as in Example 55.
Yield 11.0 mg (30%), TOF-MS: 785.24
Example 105
The above compound was prepared in the same manner as in Example 1.
Yield 13.3 mg (40%), TOF-MS: 618.89
Example 106
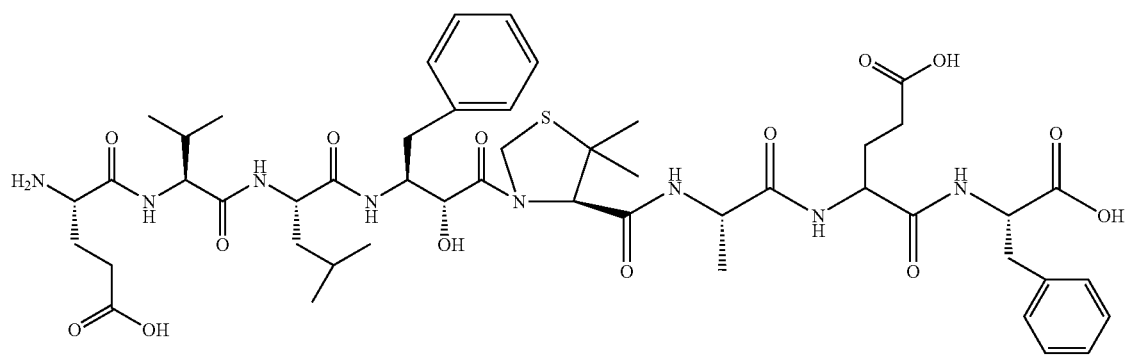

The above compound was prepared in the same manner as in Example 1.
Yield 11.2 mg (21%), TOF-MS: 1027.75
Example 107
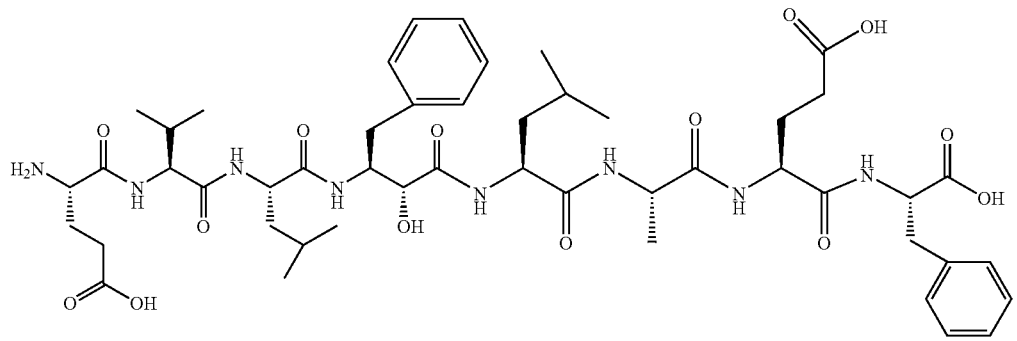
The above compound was prepared in the same manner as in Example 1.
Yield 32.2 mg (75%), TOF-MS: 998.60
Example 108
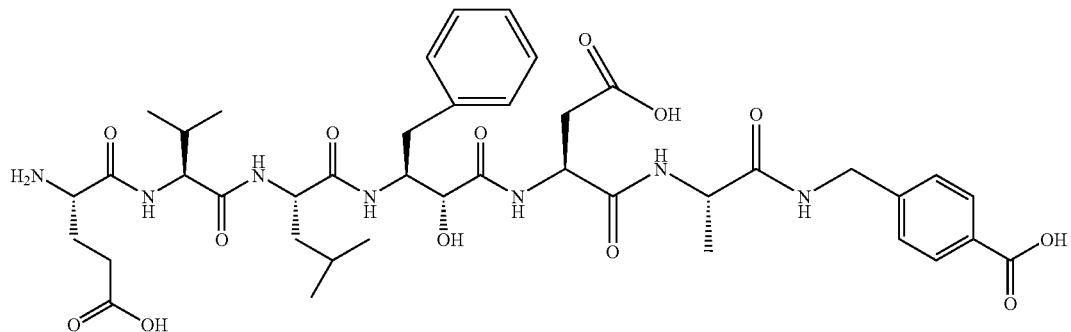
The above compound was prepared in the same manner as in Example 55.
Yield 22.3 mg (45%), TOF-MS: 856.94
Example 109
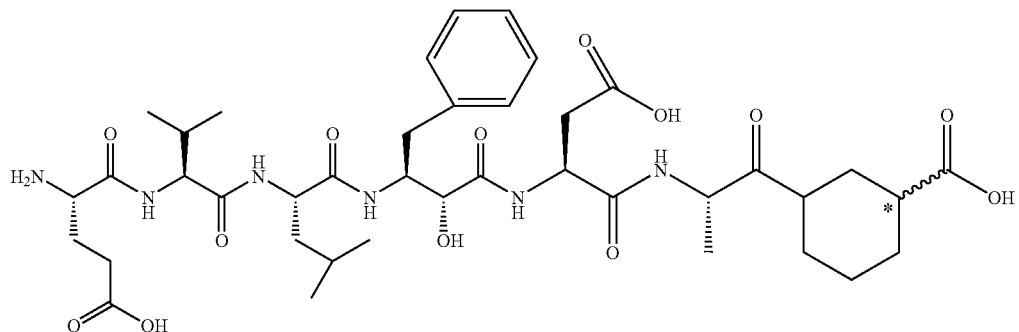
R and S The above compound was prepared in the same manner as in Example 55.
Yield 2.8 mg (10%), TOF-MS: 834.89
Example 110
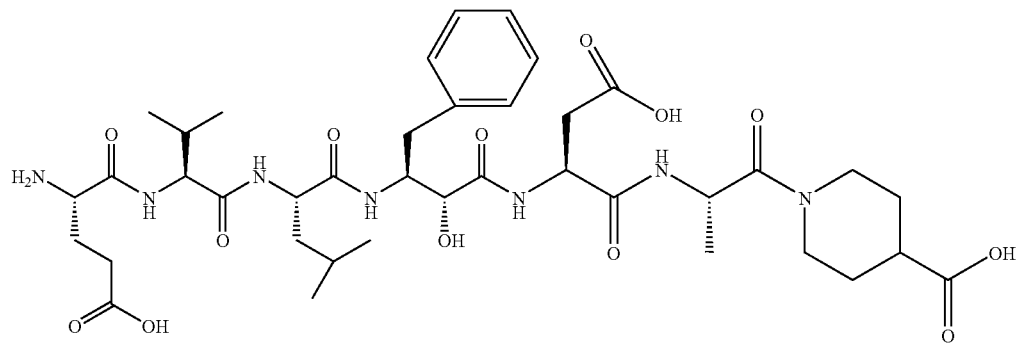
The above compound was prepared in the same manner as in Example 55.
Yield 0.1 mg (10%), TOF-MS: 834.97
Example 111
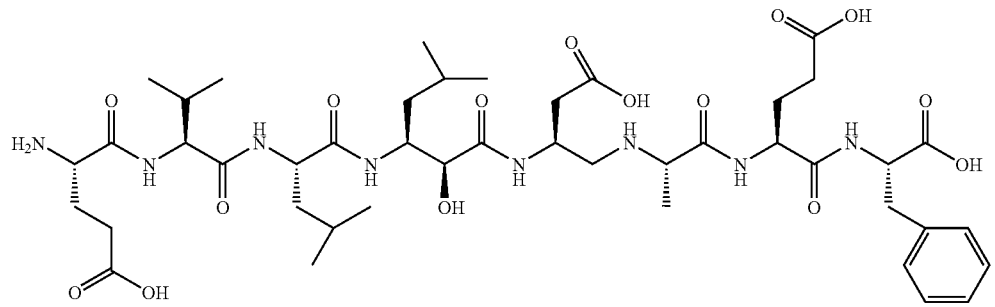
The above compound was prepared in the same manner as in Example 1.
Yield 11.0 mg (29%), TOF-MS: 965.99
Example 112
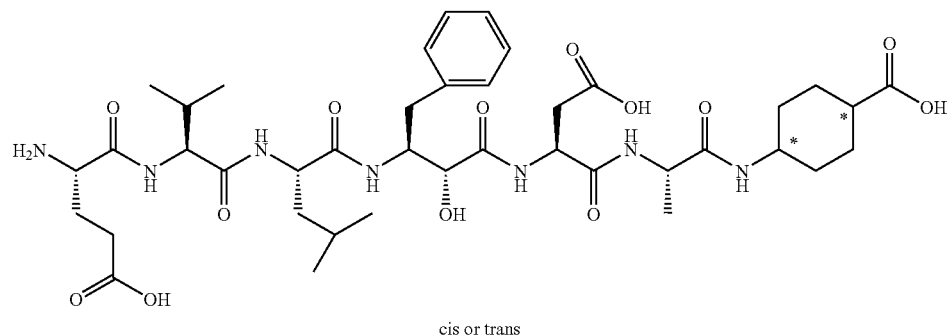
cis or trans The above compound was prepared in the same manner as in Example 55.
Yield 24.4 mg (47%), TOF-MS: 848.85
Example 113
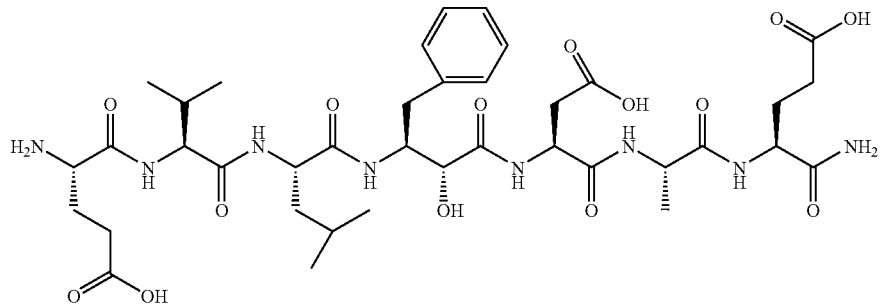
The above compound was prepared in the same manner as in Example 1.
Yield 26.9 mg (55%), TOF-MS: 851.91
Example 114
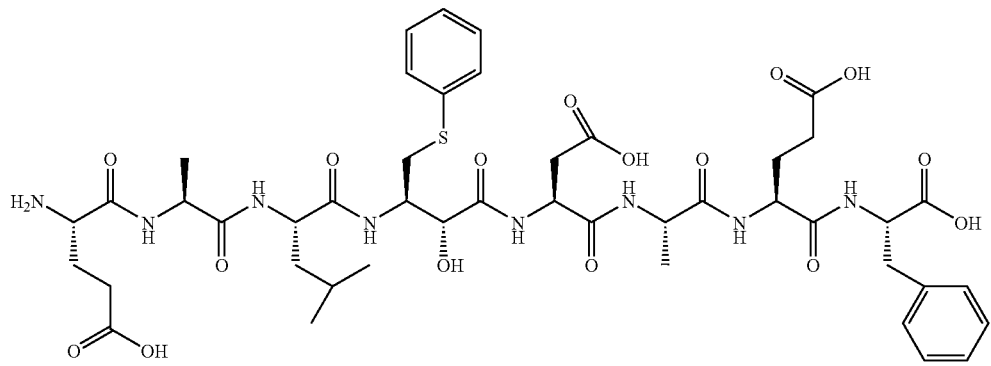
Yield 7.8 mg (23%), TOF-MS: 1004.07
Example 115
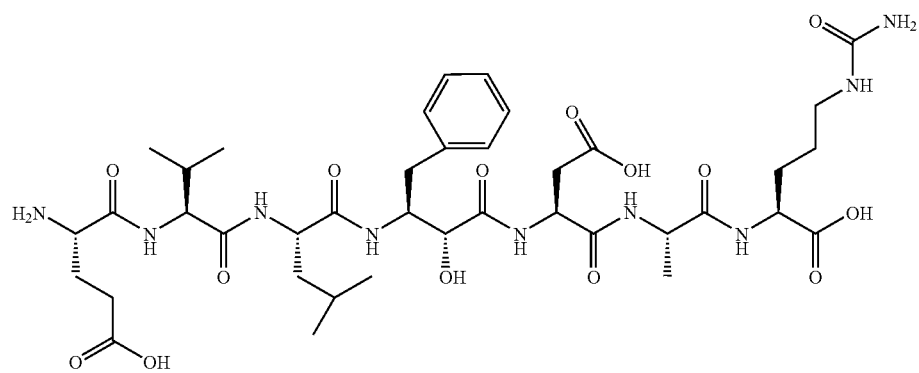

The above compound was prepared in the same manner as in Example 1.
Yield 12.4 mg (18%), TOF-MS: 880.88
Example 116
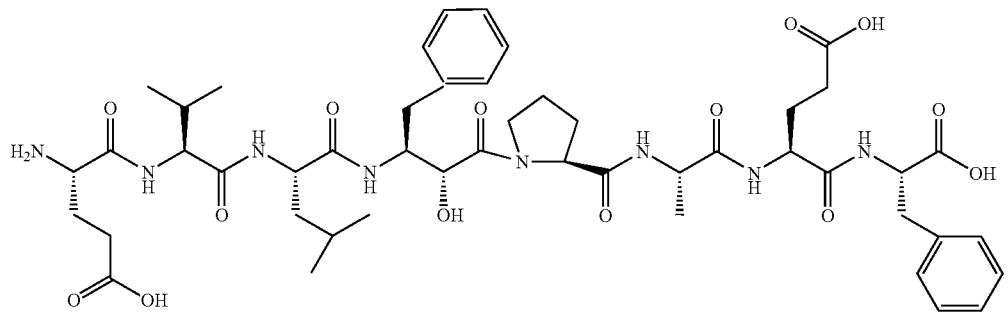
The above compound was prepared in the same manner as in Example 1.
Yield 8.8 mg (16%), TOF-MS: 982.36
Example 117
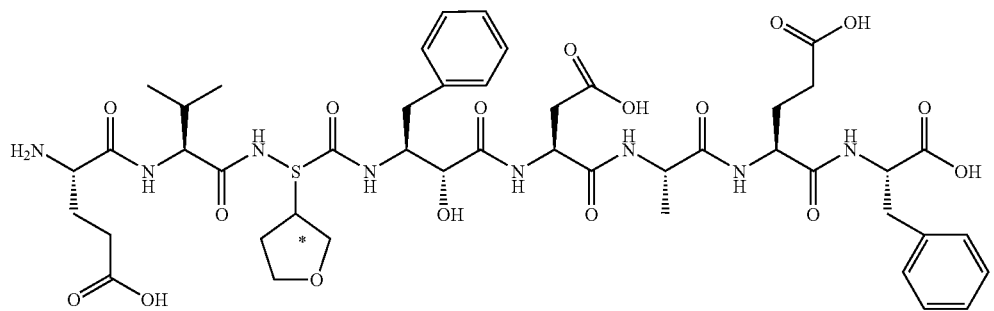
R and S
The above compound was prepared in the same manner as in Example 1.
Yield 13.4 mg (25%), TOF-MS: 1014.38
Example 118
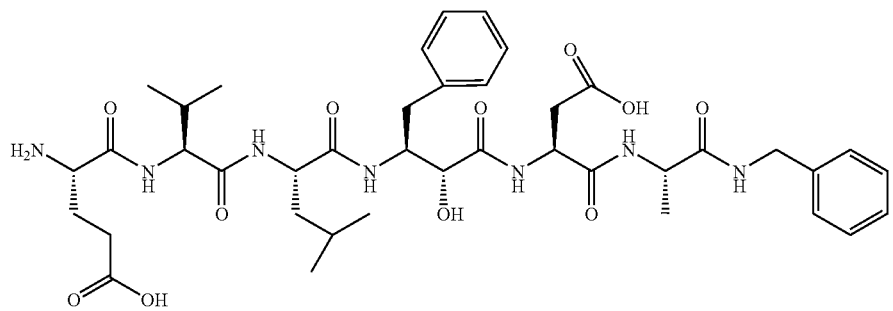
The above compound was prepared in the same manner as in Examples 50-54.
Yield 2.6 mg (25%), TOF-MS: 812.96

Example 119
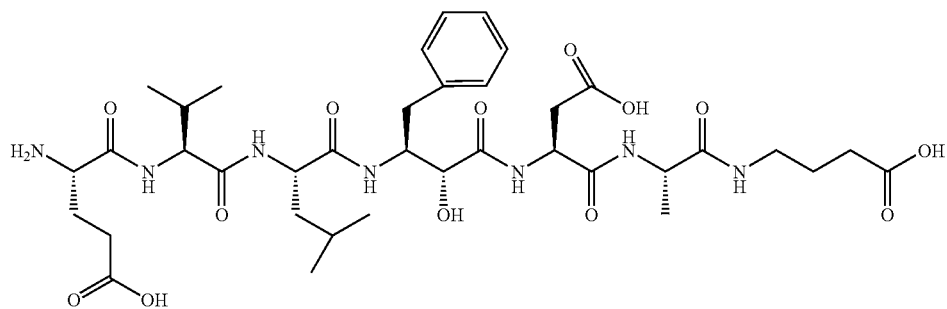
The above compound was prepared in the same manner as in Example 1.
Yield 27.7 mg (77%), TOF-MS: 808.56
Example 120
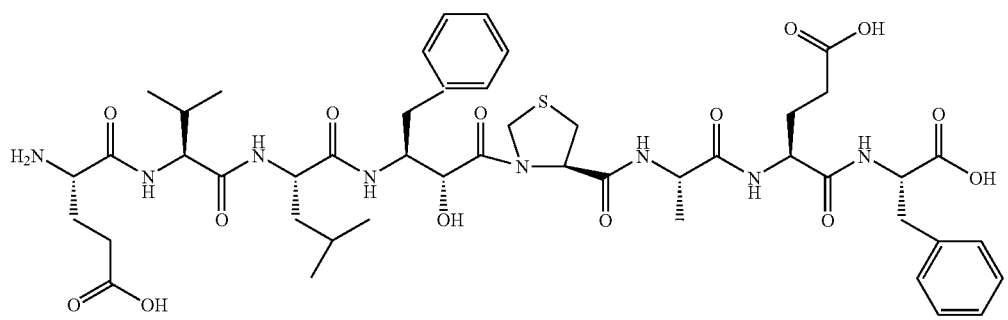
The above compound was prepared in the same manner as in Example 1.
Yield 12.1 mg (20%), TOF-MS: 1000.11
Example 121
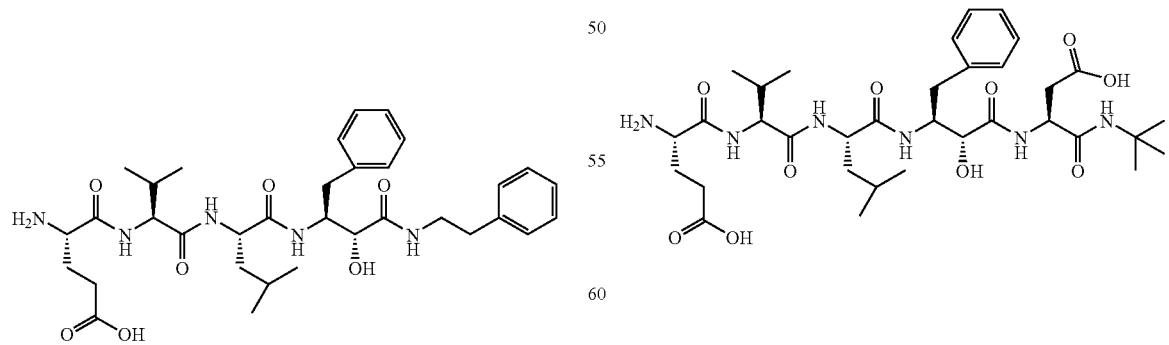
The above compound was prepared in the same manner as in Examples 46-49.
Yield 3.9 mg (34%), TOF-MS: 640.87
Example 122
The above compound was prepared in the same manner as in Examples 46-49.
Yield 21.2 mg (49%), TOF-MS: 707.78

Example 123

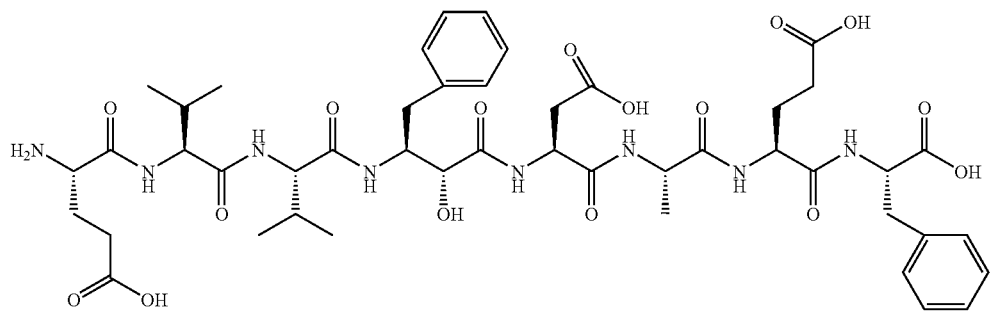

The above compound was prepared in the same manner as in Example 1.

Yield 7.3 mg (72%), TOF-MS: 986.12

Example 124

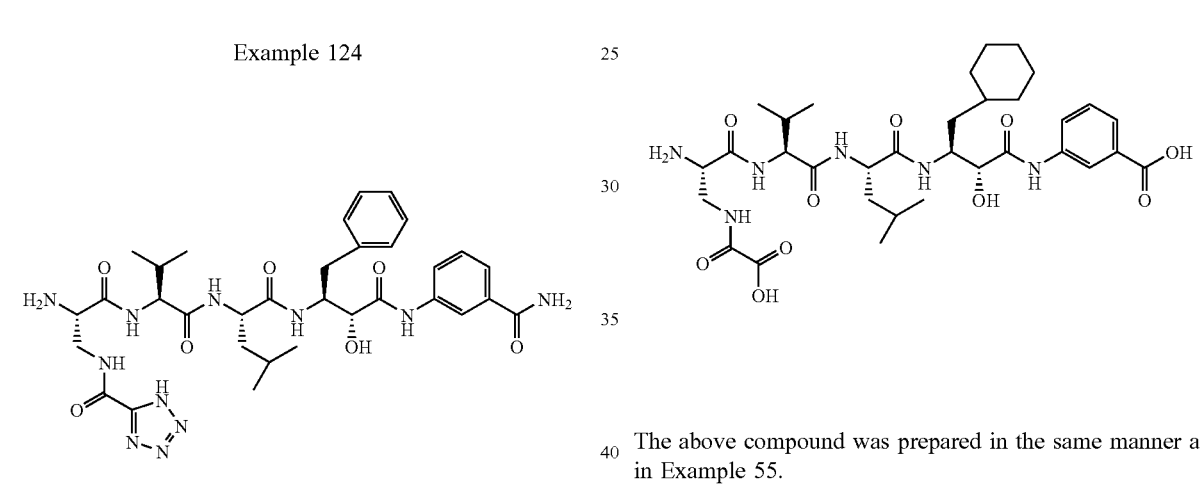

The above compound was prepared in the same manner as in Examples 46-49.

Yield 5.7 mg (57%), TOF-MS: 708.81

Example 125

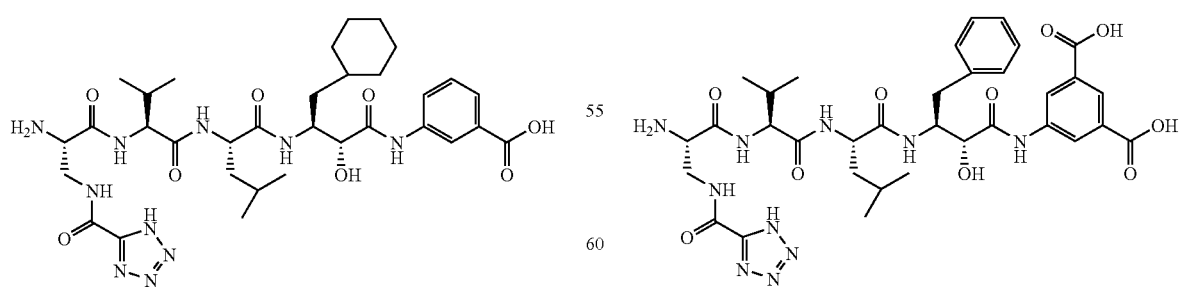

The above compound was prepared in the same manner as in Example 55.

Yield 0.6 mg (7.4%), TOF-MS: 709.73

Example 126

The above compound was prepared in the same manner as in Example 55.

Yield 4.1 mg (25%), TOF-MS: 691.73

Example 127

The above compound was prepared in the same manner as in Examples 55-54.

Yield 4.1 mg (19%), TOF-MS: 753.92

Example 128

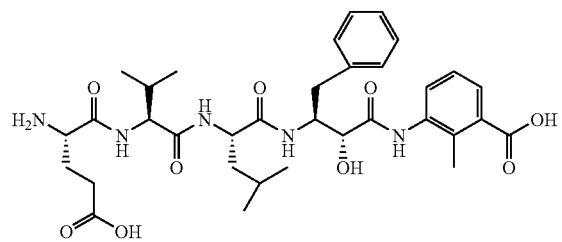

The above compound was prepared in the same manner as in Example 55.

Yield 15.0 mg (14%), TOF-MS: 670.86

Example 129

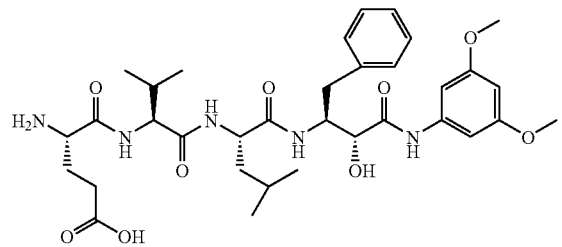

The above compound was prepared in the same manner as in Examples 46 to 49.

Yield 30.0 mg (20%), TOF-MS: 672.97

Example 130

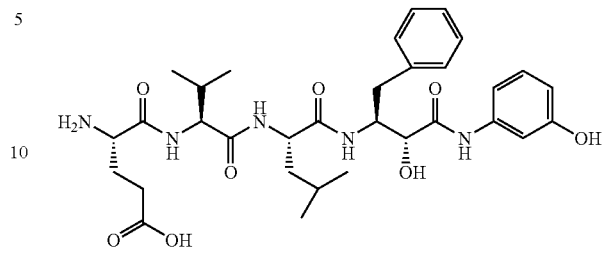

The above compound was prepared in the same manner as in Examples 46 to 49.

Yield 3.2 mg (6.4%), TOF-MS: 628.66

Example 131

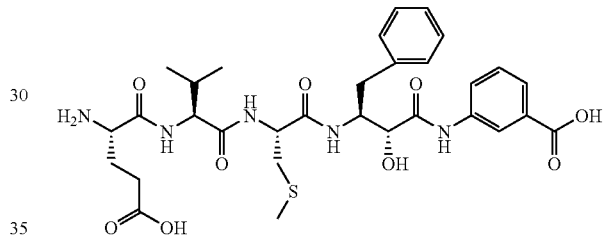

The above compound was prepared in the same manner as in Example 55.

Yield 8.6 mg (46%), TOF-MS: 660.79

Example 132

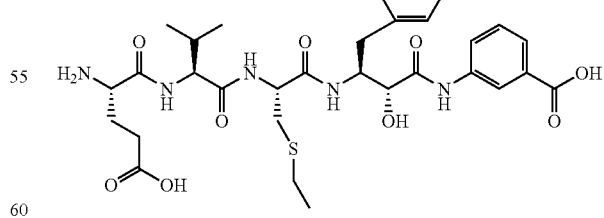

The above compound was prepared in the same manner as in Example 55.

Yield 5.8 mg (29%), TOF-MS: 674.83

Example 133
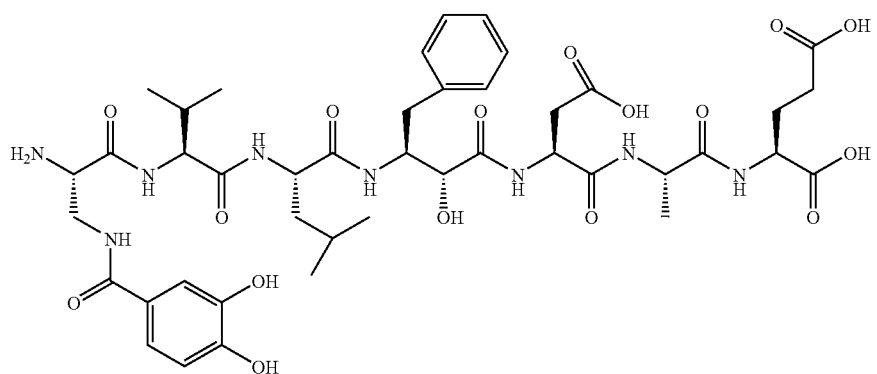
The above compound was prepared in the same manner as in Example 1.
Yield 4.2 mg (13%), TOF-MS: 945.88
Example 134
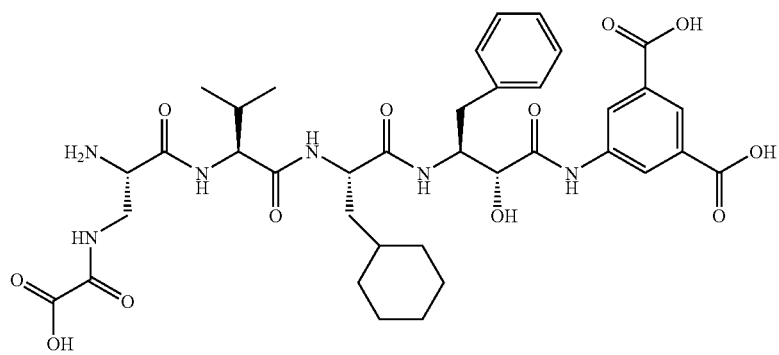
The above compound was prepared in the same manner as in Examples 50-54.
Yield 4.6 mg (46%), TOF-MS: 769.88
Example 135
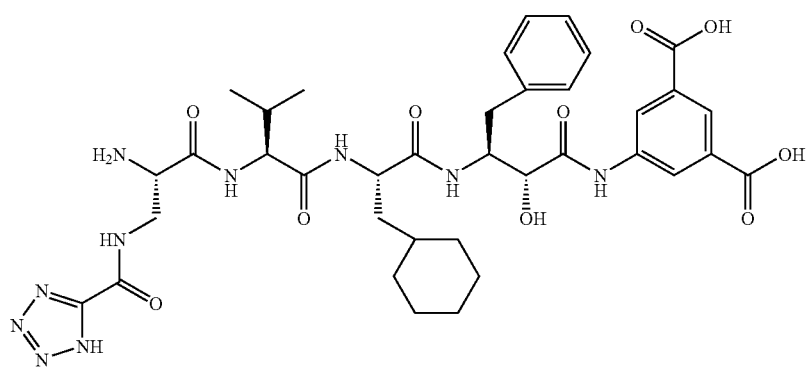

The above compound was prepared in the same manner as in Examples 50-54.
Yield 5.6 mg (50%), TOF-MS: 793.89
Example 136
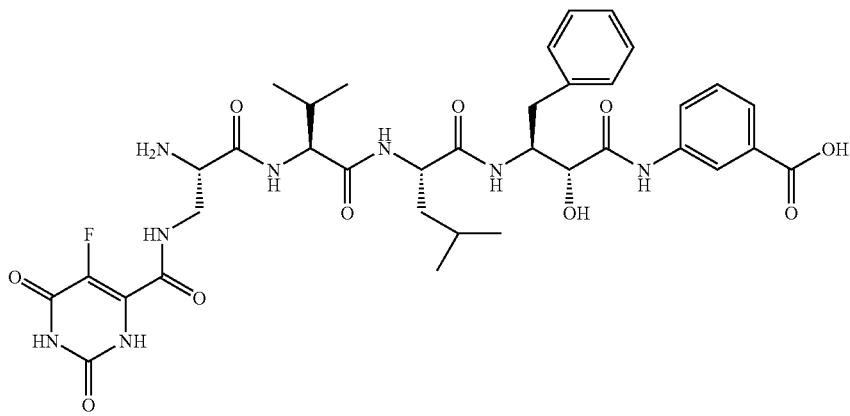
The above compound was prepared in the same manner as in Example 55.
Yield 6.2 mg (35%), TOF-MS: 769.79
Example 137
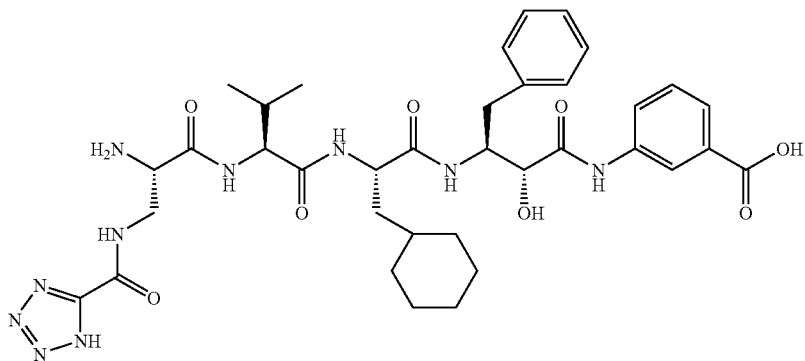
The above compound was prepared in the same manner as in Example 55.
Yield 2.1 mg (9%), TOF-MS: 749.93

Example 138
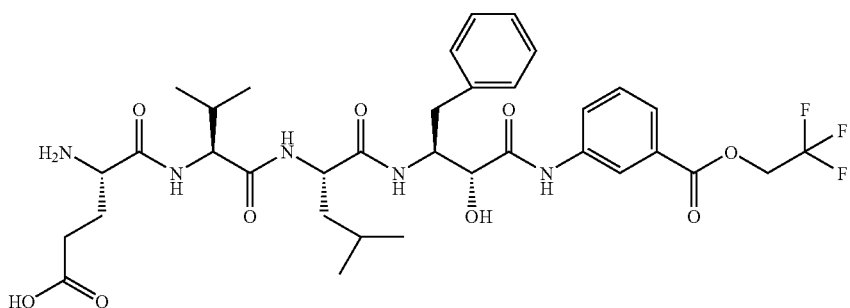
The above compound was prepared in the same manner as in Examples 46-49.
Yield 4.4 mg (44%), TOF-MS: 738.92
Example 139
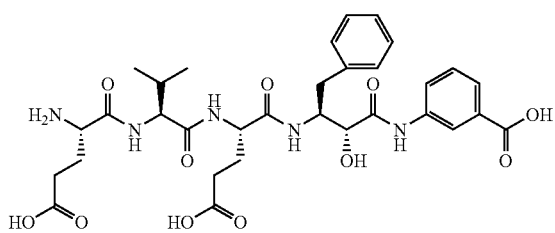
The above compound was prepared in the same manner as in Example 55.
Yield 7.7 mg (57%), TOF-MS: 672.78
Example 140
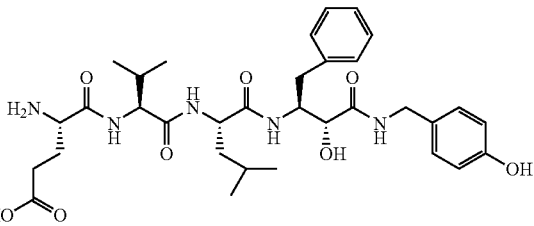
The above compound was prepared in the same manner as in Examples 46-49.
Yield 2.5 mg (9.3%), TOF-MS: 642.77
Example 141
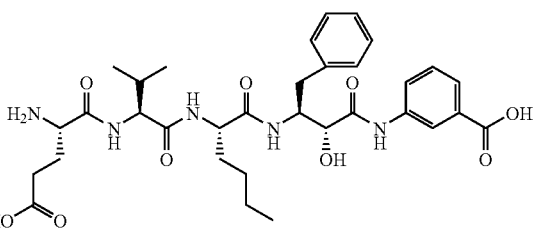
The above compound was prepared in the same manner as in Example 55.
Yield 6.1 mg (16%), TOF-MS: 656.75

Example 142
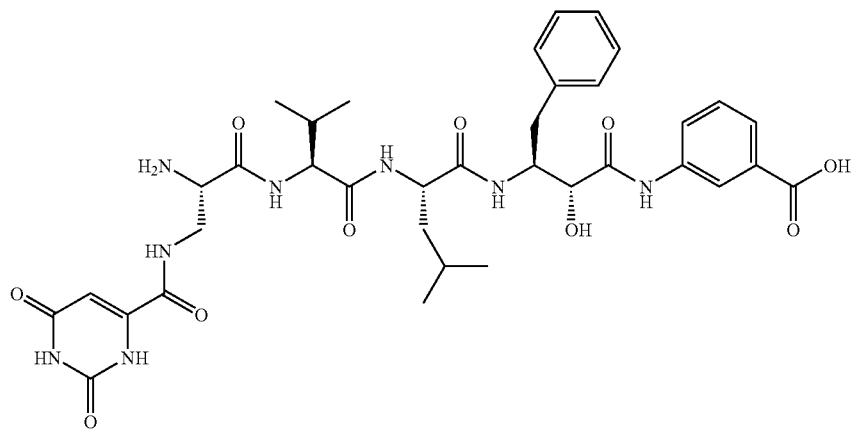
The above compound was prepared in the same manner as in Example 55.
Yield 6.5 mg (43%), TOF-MS: 751.96
Example 143
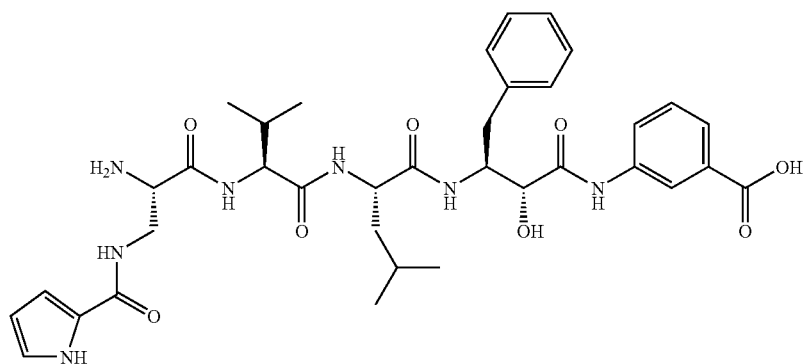
The above compound was prepared in the same manner as in Example 55.
Yield 3.5 mg (17%), TOF-MS: 706.85

Example 144
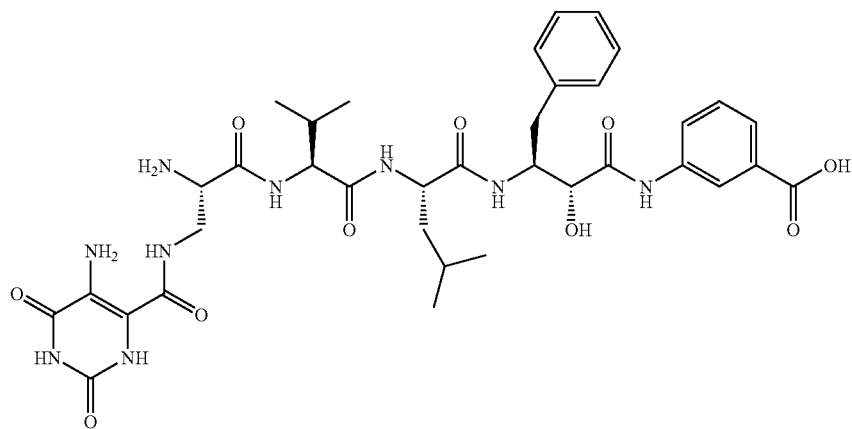
The above compound was prepared in the same manner as in Example 55.
Yield 5.6 mg (42%), TOF-MS: 766.81
Example 145
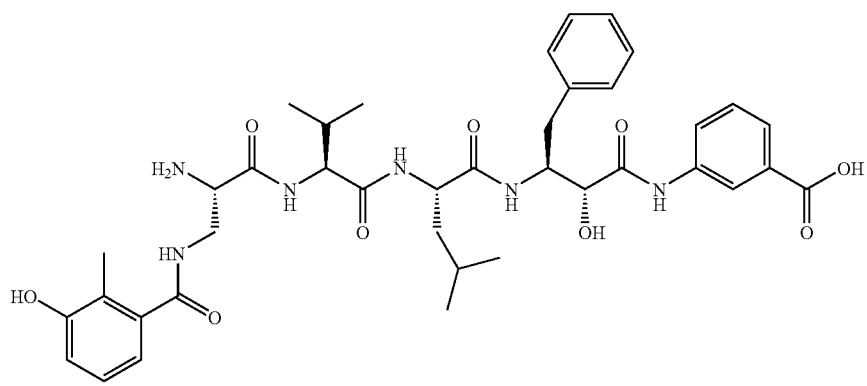
The above compound was prepared in the same manner as in Example 55.
Yield 4.8 mg (26%), TOF-MS: 747.84

Example 146
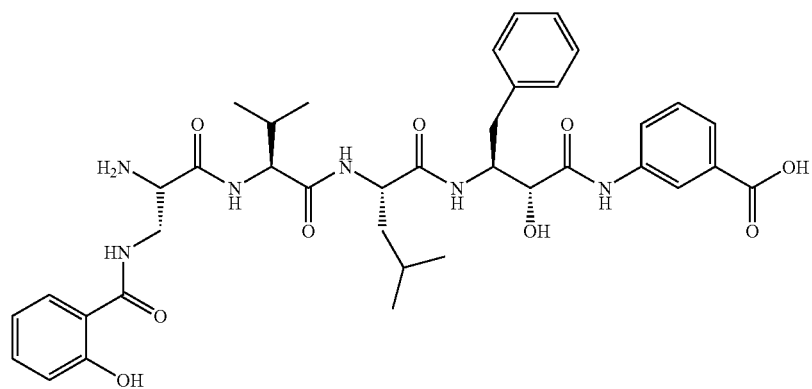
The above compound was prepared in the same manner as in Example 55.
Yield 3.1 mg (16%), TOF-MS: 733.87
Example 147
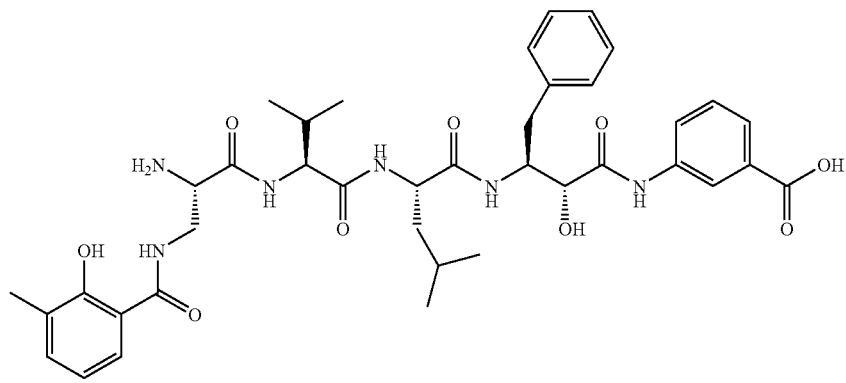
The above compound was prepared in the same manner as in Example 55.
Yield 4.5 mg (29%), TOF-MS: 748.00

Example 148
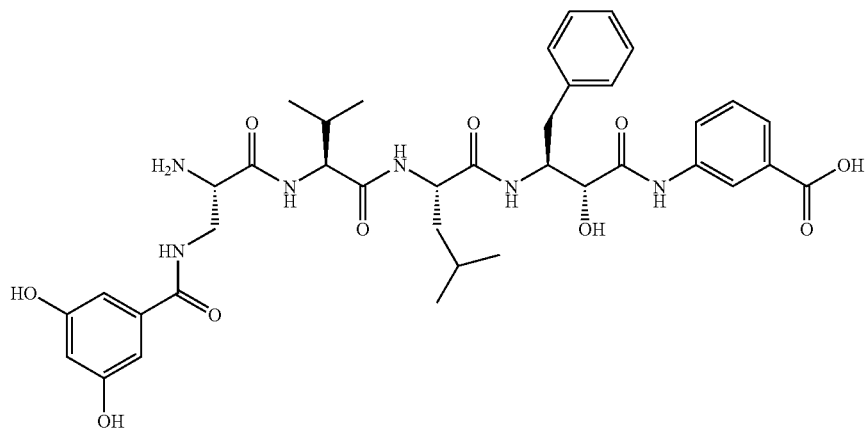
The above compound was prepared in the same manner as in Example 55.
Yield 3.3 mg (19%), TOF-MS: 749.88
Example 149
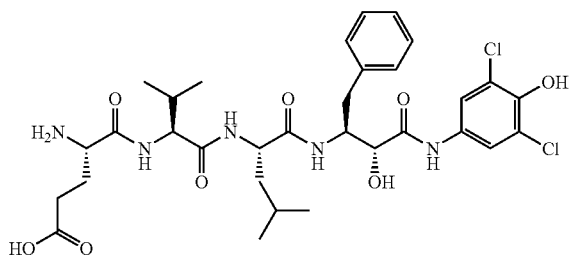
The above compound was prepared in the same manner as in Examples 46-49.
Yield 10.0 mg (6.5%), TOF-MS: 698.67
Example 150
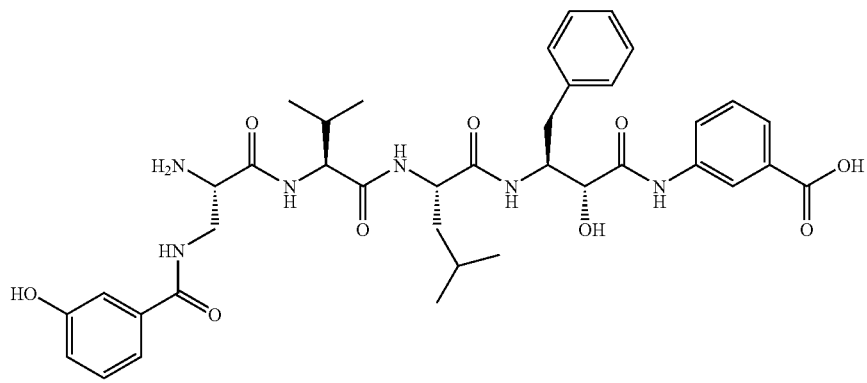
The above compound was prepared in the same manner as in Example 55.
Yield 7.3 mg (58%), TOF-MS: 733.93

Example 151
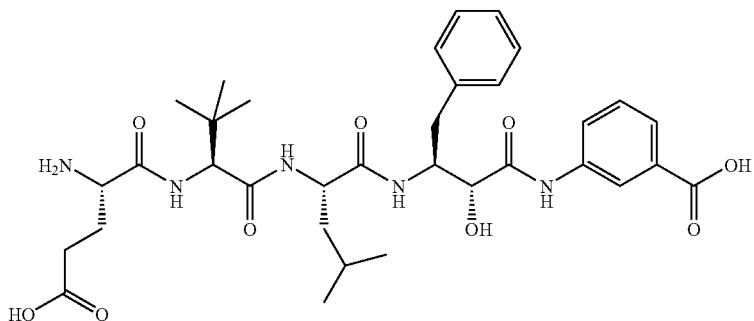
The above compound was prepared in the same manner as in Example 55.
Yield 7.3 mg (53%), TOF-MS: 670.62
Example 152
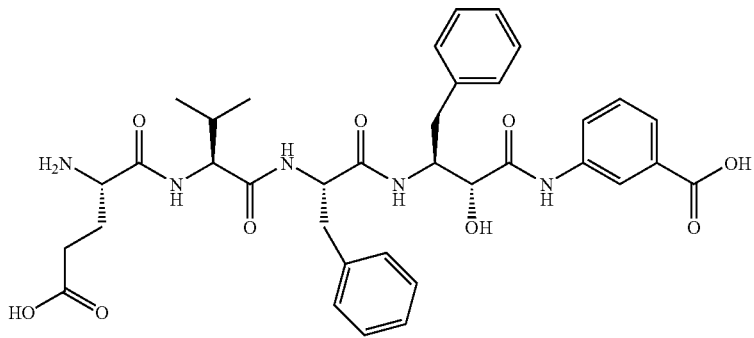
The above compound was prepared in the same manner as in Example 55.
Yield 6.3 mg (48%), TOF-MS: 690.64
Example 153
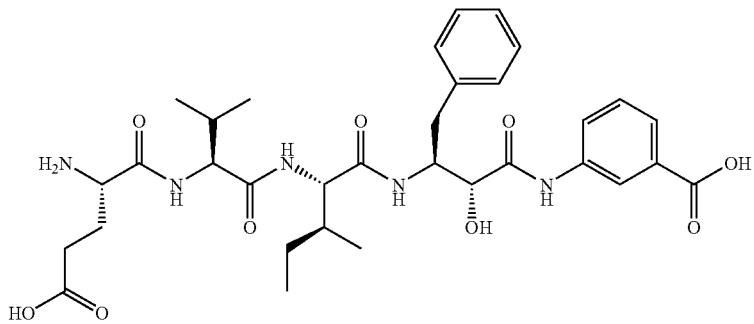
The above compound was prepared in the same manner as in Example 55.
Yield 6.2 mg (44%), TOF-MS: 656.78

Example 154
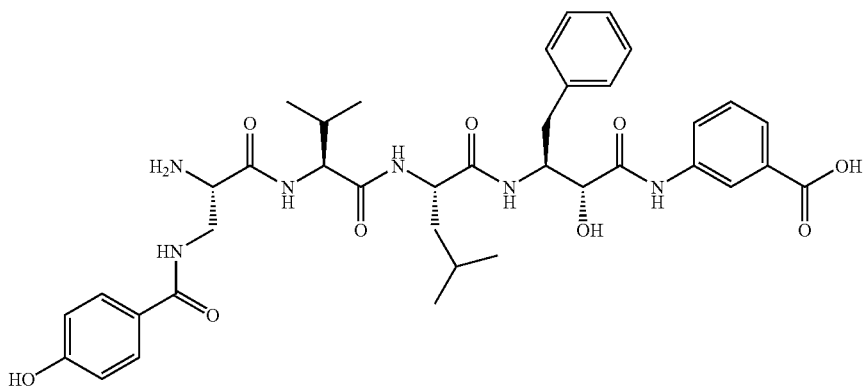
The above compound was prepared in the same manner as in Example 55.
Yield 5.3 mg (53%), TOF-MS: 733.93
Example 155
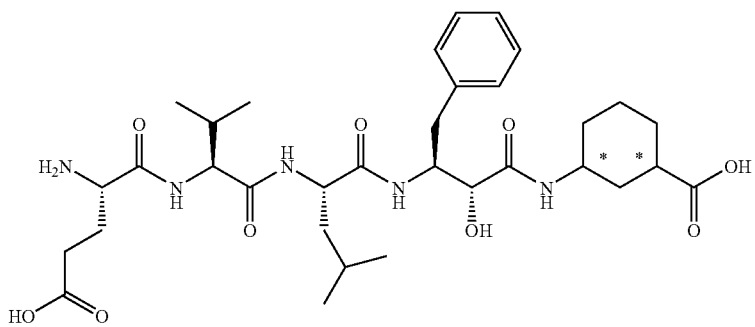
*SS and RR (trans)
The above compound was prepared in the same manner as in Example 55.
Yield 2.2 mg (4.6%), TOF-MS: 662.86
Example 156
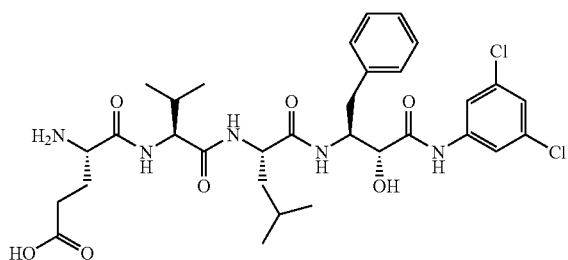
The above compound was prepared in the same manner as in Examples 46-49.
Yield 35 mg (23%), TOF-MS: 682.81

Example 157
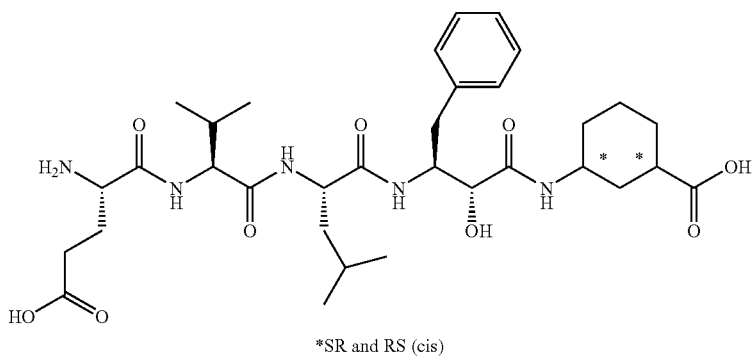
*SR and RS (cis)
The above compound was prepared in the same manner as in Example 55.
Yield 3.0 mg (5.5%), TOF-MS: 662.91
Example 158
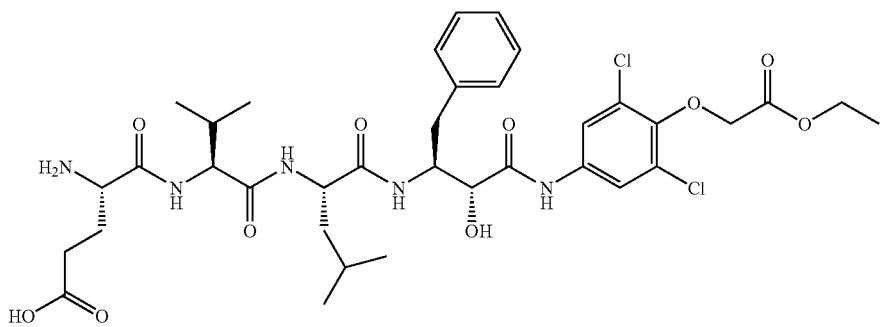
The above compound was prepared in the same manner as in Examples 46-49.
Yield 40 mg (23%), TOF-MS: 782.89
Example 159
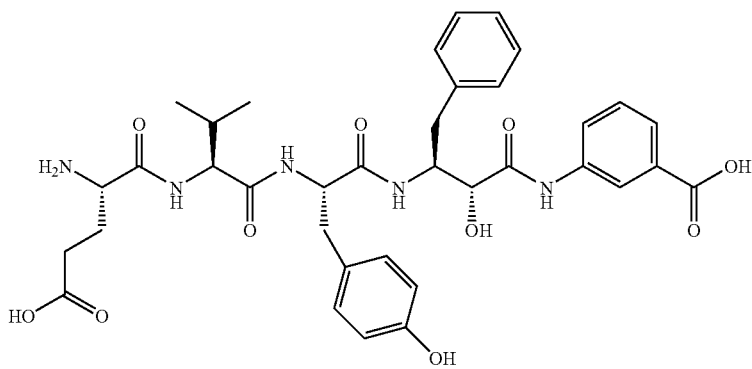
The above compound was prepared in the same manner as in Example 55.
Yield 4.9 mg (40%), TOF-MS: 706.87

Example 160
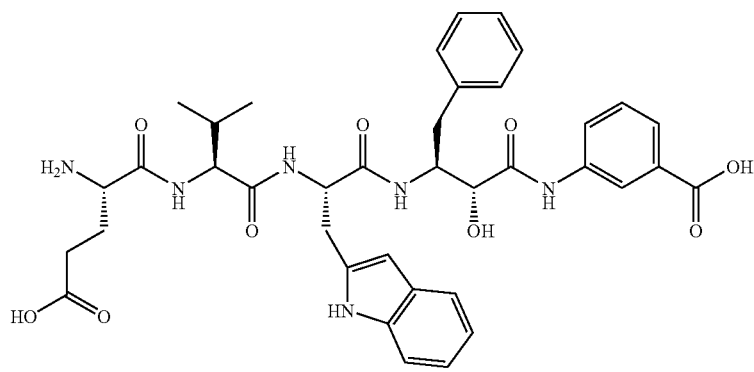
The above compound was prepared in the same manner as in Example 55.
Yield 3.9 mg (32%), TOF-MS: 729.87
Example 161
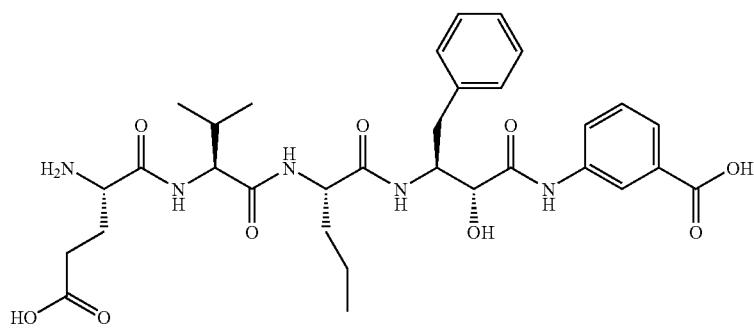
The above compound was prepared in the same manner as in Example 55.
Yield 6.2 mg (52%), TOF-MS: 642.87
Example 162
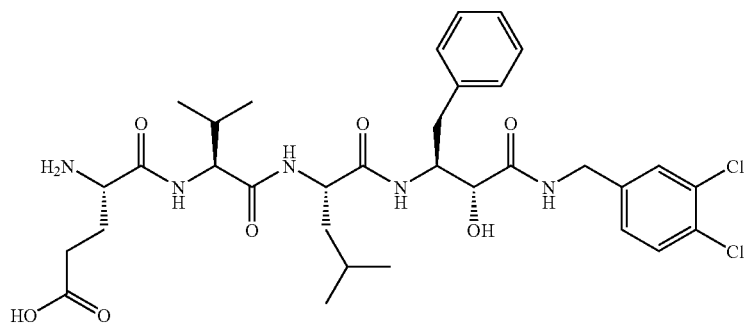
The above compound was prepared in the same manner as in Examples 46-49.
Yield 50.0 mg (33%), TOF-MS: 694.87

Example 163
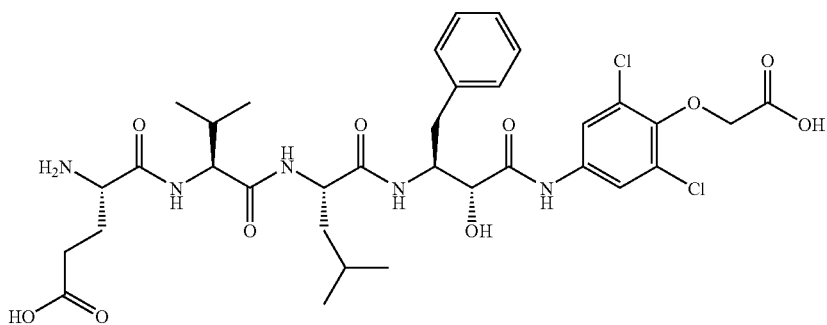
The above compound was prepared in the same manner as in Examples 50-54.
Yield 10.0 mg (6.0%), TOF-MS: 756.58
Example 164
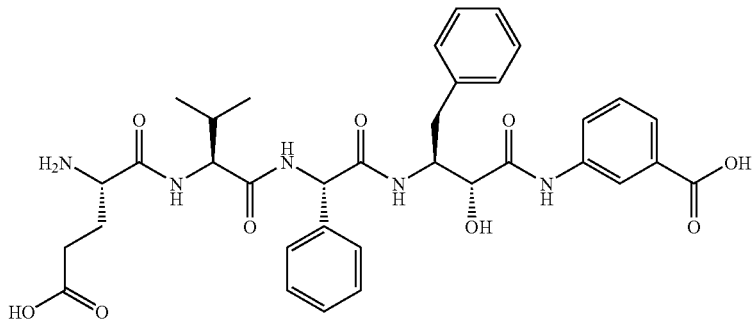
The above compound was prepared in the same manner as in Example 55.
Yield 4.5 mg (48%), TOF-MS: 676.62
Example 165
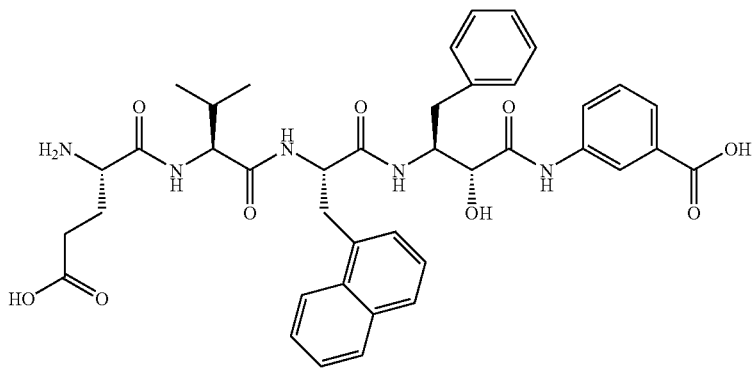
The above compound was prepared in the same manner as in Example 55.
Yield 6.4 mg (62%), TOF-MS: 740.75

Example 166
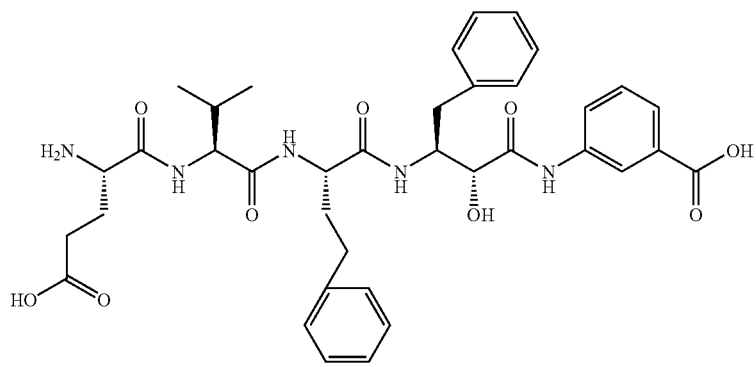
The above compound was prepared in the same manner as in Example 55.
Yield 6.6 mg (53%), TOF-MS: 704.87
Example 167
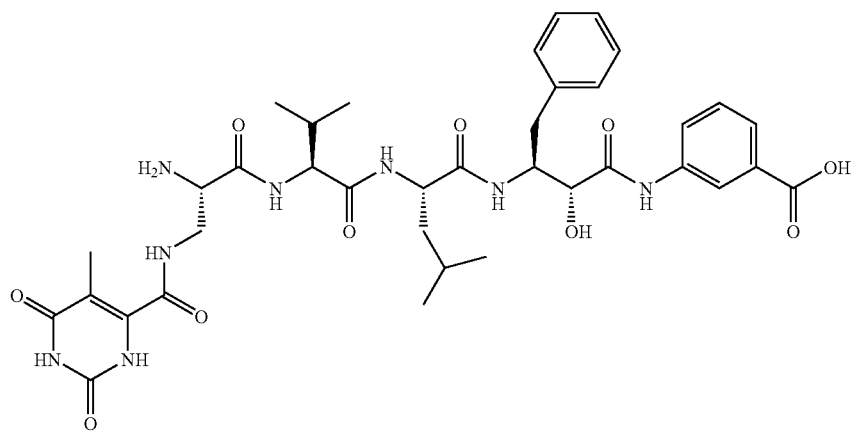
The above compound was prepared in the same manner as in Example 55.
Yield 3.7 mg (44%), TOF-MS: 877.78

Example 168
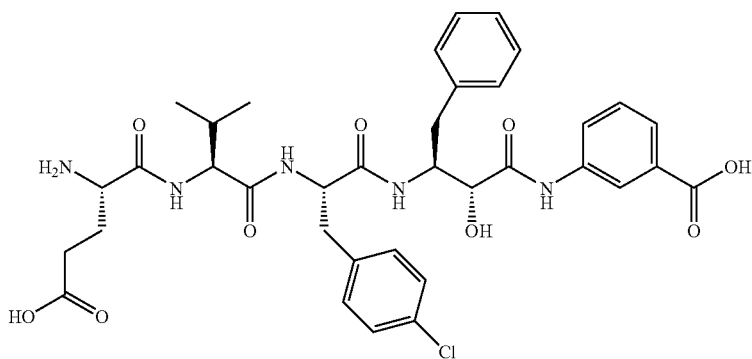
The above compound was prepared in the same manner as in Example 55.
Yield 1.3 mg (8%), TOF-MS: 725.02
Example 169
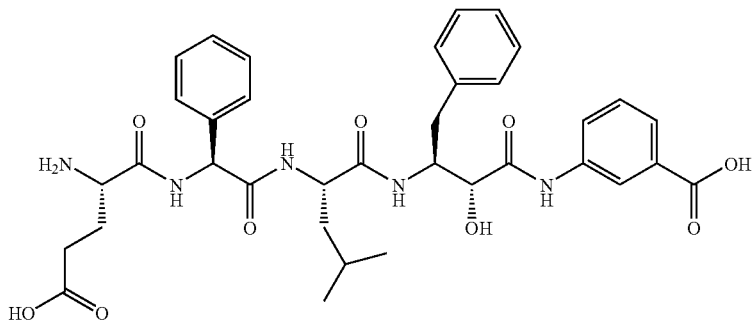
The above compound was prepared in the same manner as in Example 55.
Yield 6.0 mg (58%), TOF-MS: 690.72
Example 170
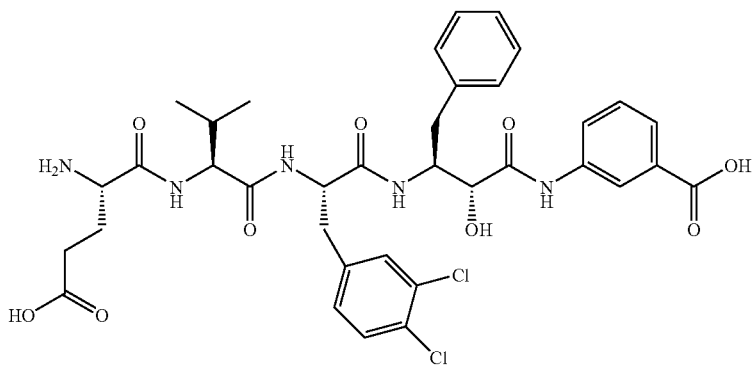
The above compound was prepared in the same manner as in Example 55.
Yield 5.2 mg (34%), TOF-MS: 758.80

Example 171
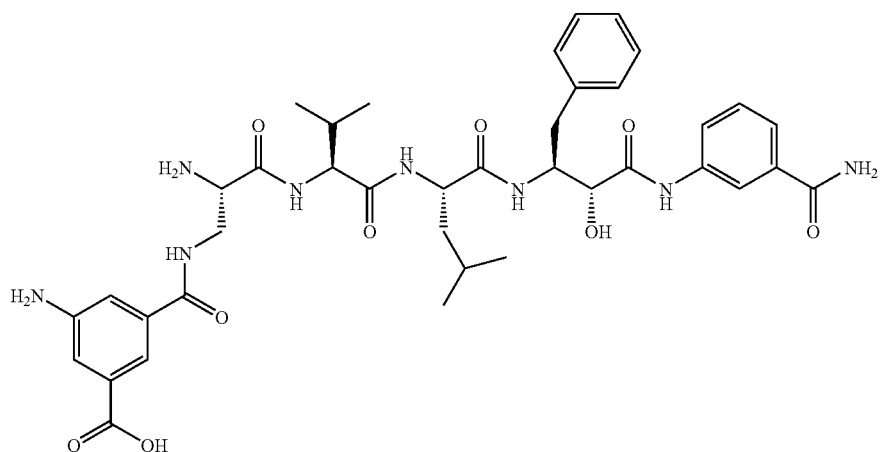
The above compound was prepared in the same manner as in Examples 46-49.
Yield 3.1 mg (13%), TOF-MS: 775.89
Example 172
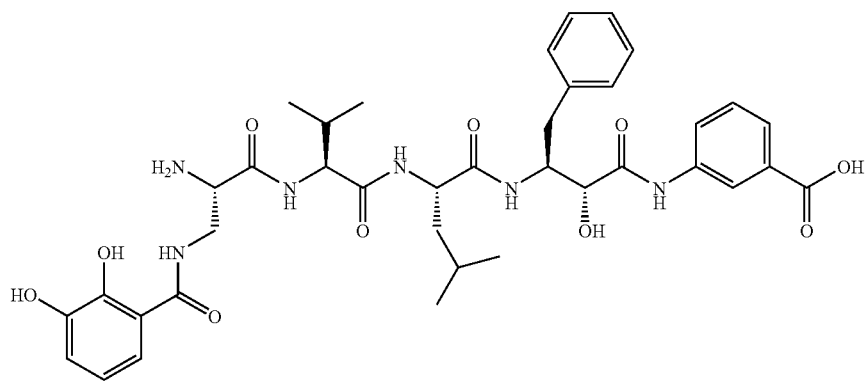
The above compound was prepared in the same manner as in Example 55.
Yield 4.1 mg (44%), TOF-MS: 749.82

Example 173
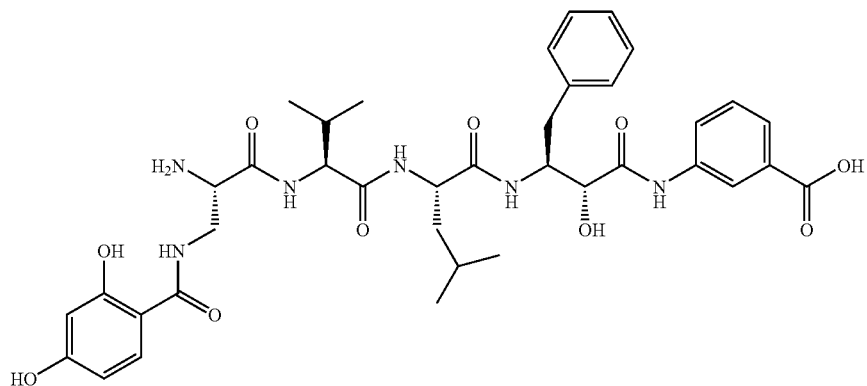
The above compound was prepared in the same manner as in Example 55.
Yield 4.7 mg (47%), TOF-MS: 749.85
Example 174
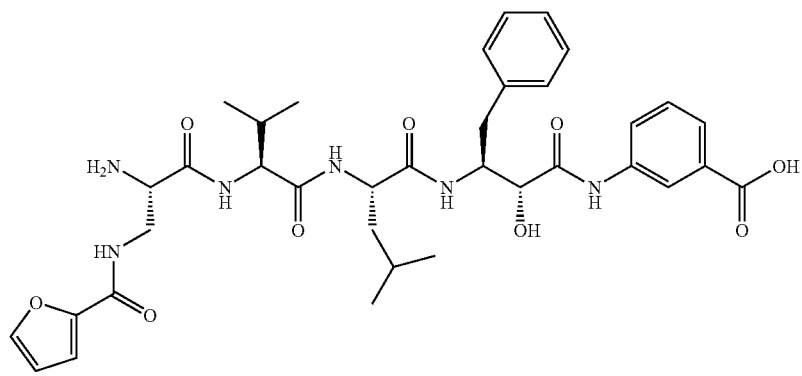
The above compound was prepared in the same manner as in Example 55.
Yield 5.5 mg (56%), TOF-MS: 707.76

Example 175
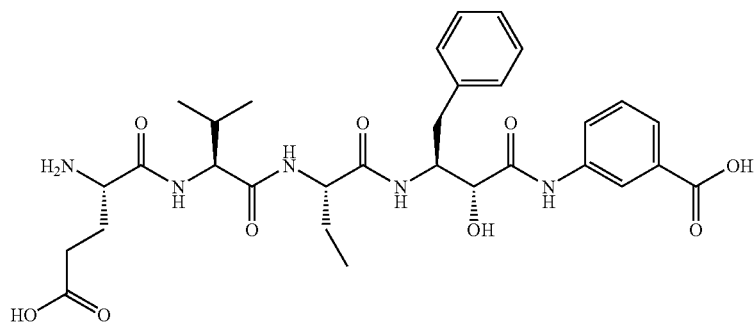
The above compound was prepared in the same manner as in Example 55.
Yield 4.1 mg (39%), TOF-MS: 628.66
Example 176
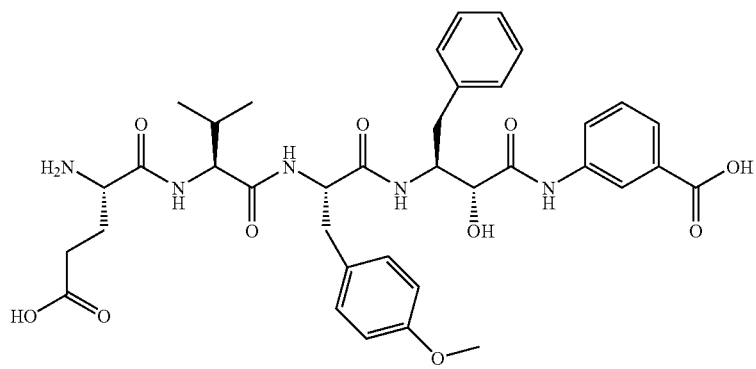
The above compound was prepared in the same manner as in Example 55.
Yield 4.8 mg (47%), TOF-MS: 720.91

Example 177
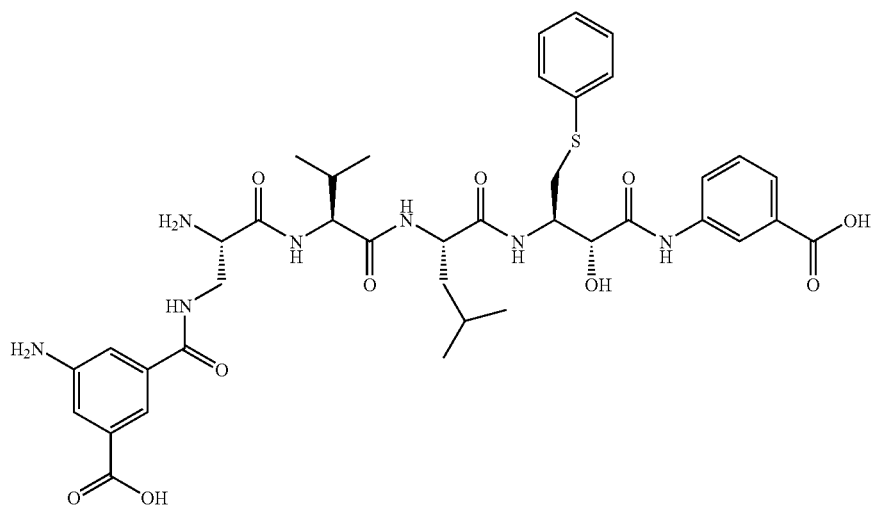
The above compound was prepared in the same manner as in Example 55.
Yield 0.77 mg (2.1%), TOF-MS: 808.99
Example 178
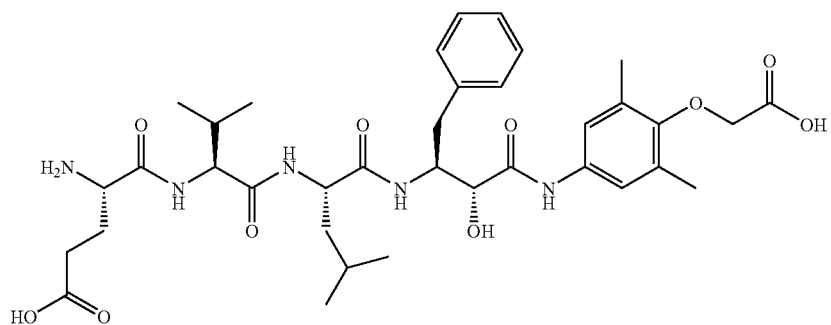
The above compound was prepared in the same manner as in Examples 50-54.
Yield 0.4 mg (1.4%), TOF-MS: 714.83

Example 179
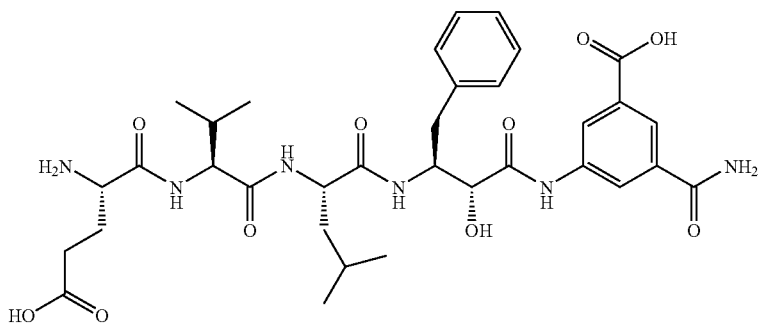
The above compound was prepared in the same manner as in Examples 50-54.
Yield 0.03 mg (0.2%), TOF-MS: 699.71
Example 180
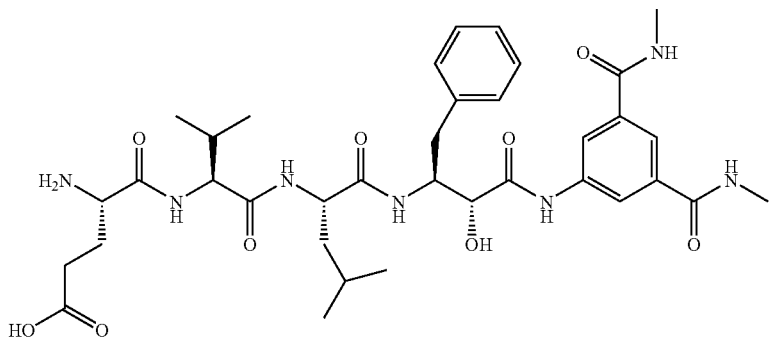
The above compound was prepared in the same manner as in Examples 50-54.
Yield 30.0 mg (19%), TOF-MS: 726.86

Example 181
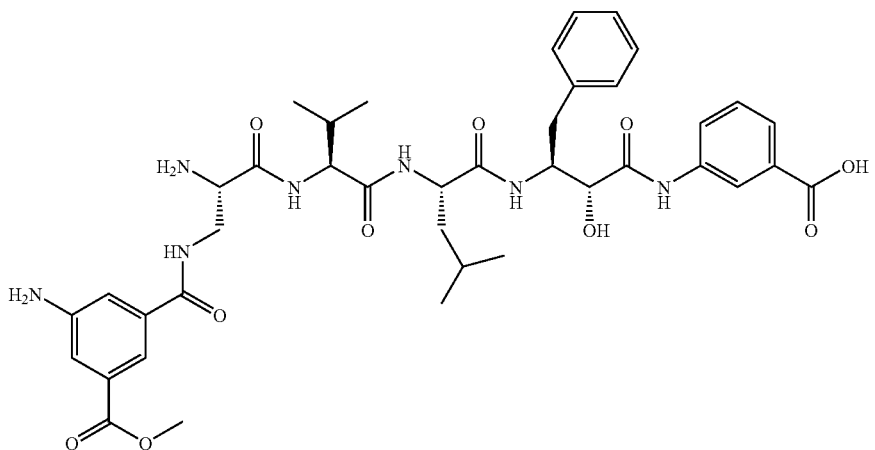
The above compound was prepared in the same manner as in Example 55.
Yield 4.4 mg (14%), TOF-MS: 790.92
Example 182
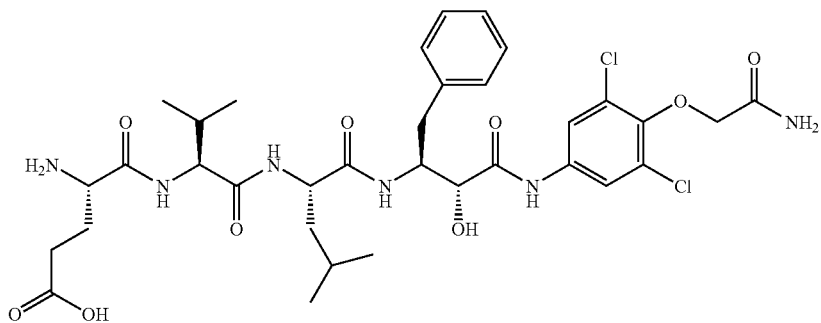
The above compound was prepared in the same manner as in Examples 46-49.
Yield 5.0 mg (5.0%), TOF-MS: 755.65

Example 183
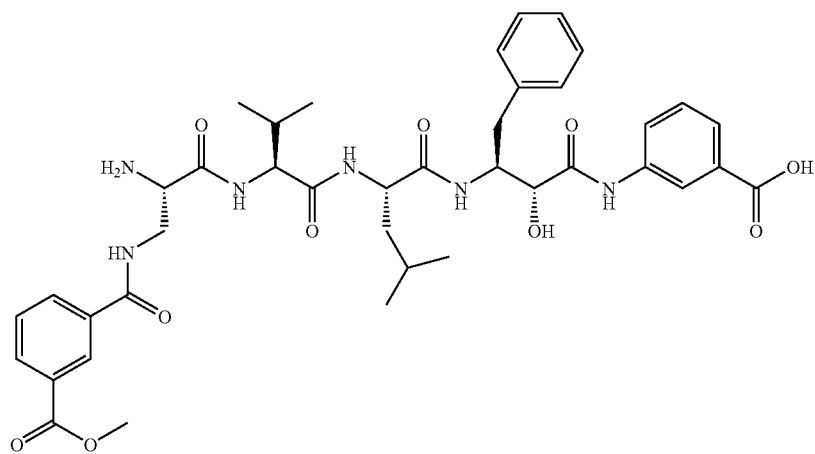
The above compound was prepared in the same manner as in Example 55.
Yield 4.2 mg (12%), TOF-MS: 775.97
Example 184
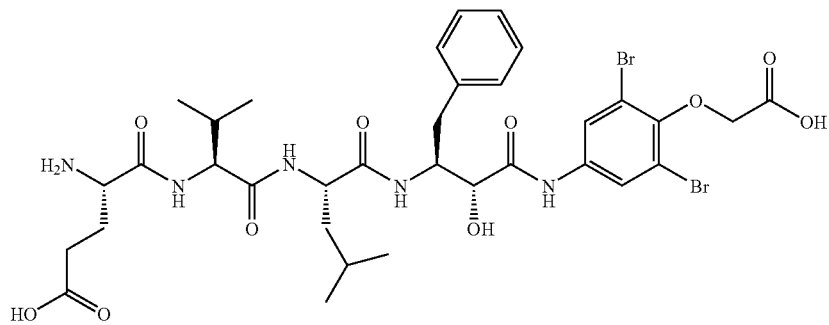
The above compound was prepared in the same manner as in Examples 50-54.
Yield 15 mg (8.1%), TOF-MS: 844.72

Example 185
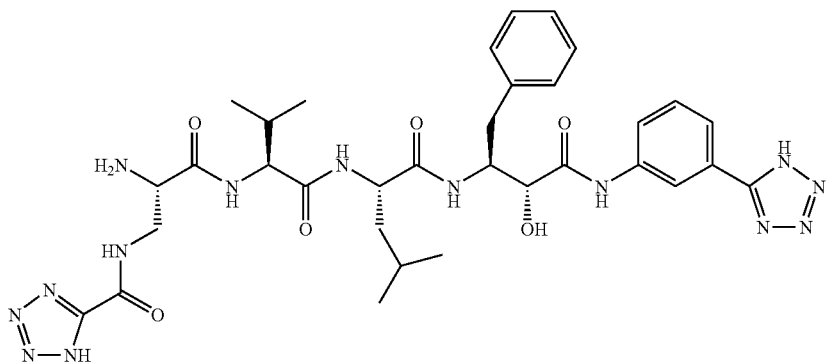
The above compound was prepared in the same manner as in Example 55.
Yield 4.5 mg (36%), TOF-MS: 733.98
Example 186
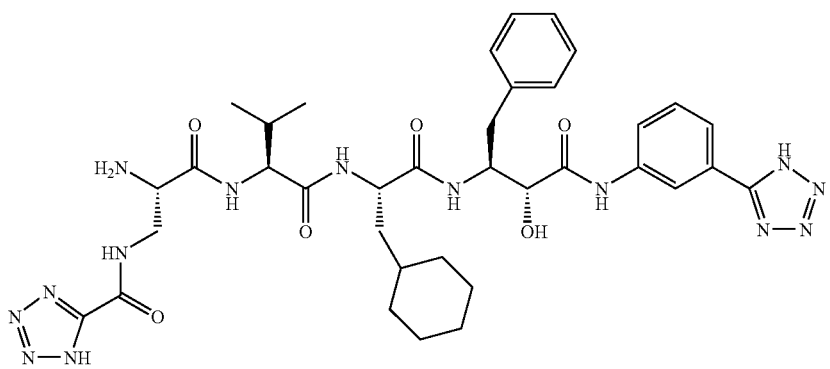
The above compound was prepared in the same manner as in Example 55.
Yield 4.9 mg (43%), TOF-MS: 777.82

Example 187
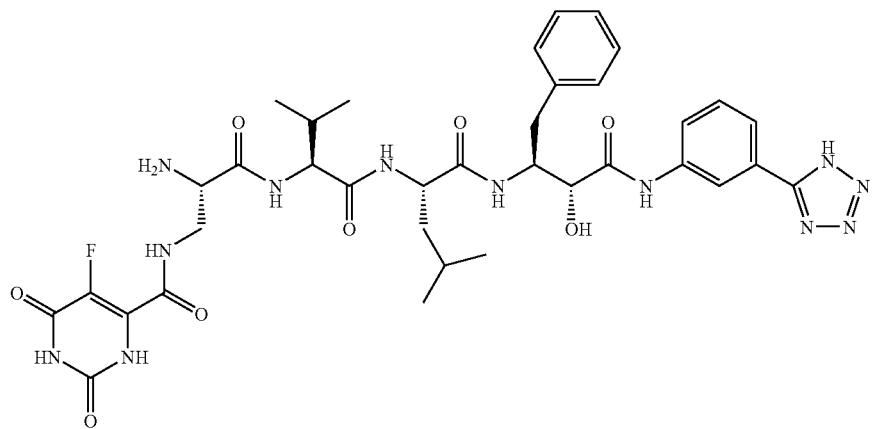
The above compound was prepared in the same manner as in Example 55.
Yield 7.0 mg (55%), TOF-MS: 793.87
Example 188
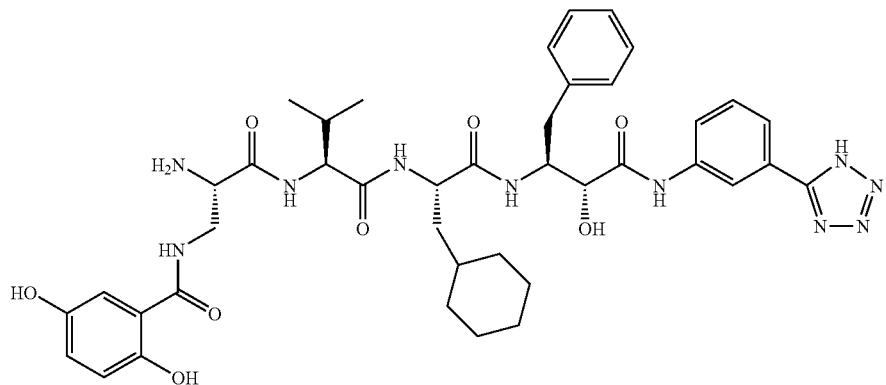
The above compound was prepared in the same manner as in Example 55.
Yield 5.1 mg (40%), TOF-MS: 813.88

Example 189
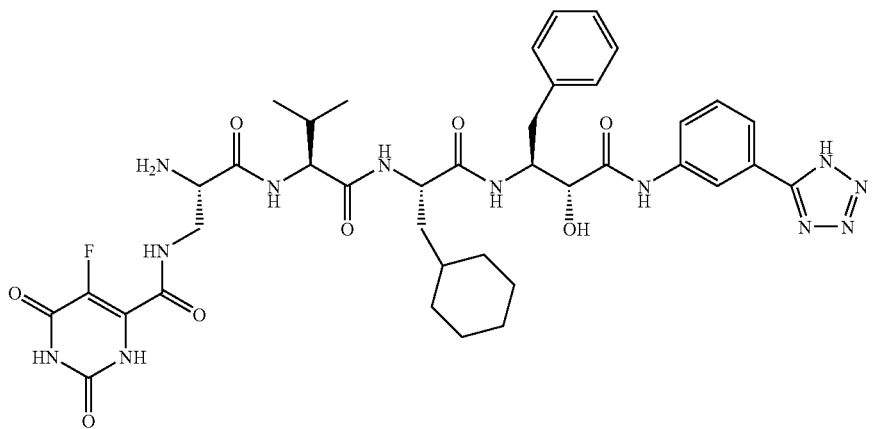
The above compound was prepared in the same manner as in Example 55.
Yield 6.9 mg (54%), TOF-MS: 833.98
Example 190
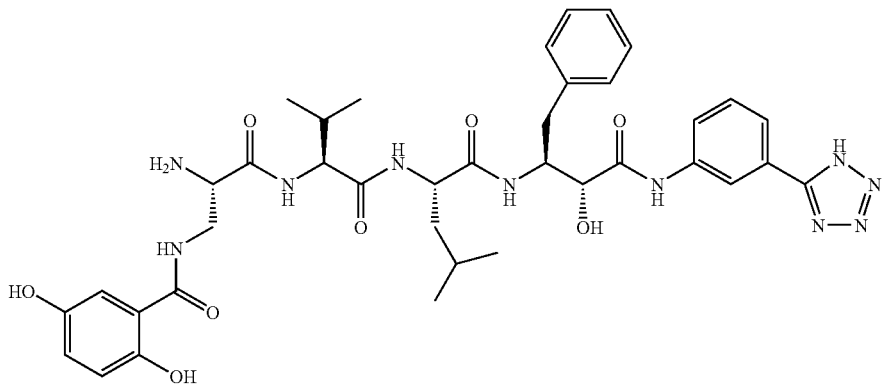
The above compound was prepared in the same manner as in Example 55.
Yield 5.0 mg (38%), TOF-MS: 773.94

Example 191

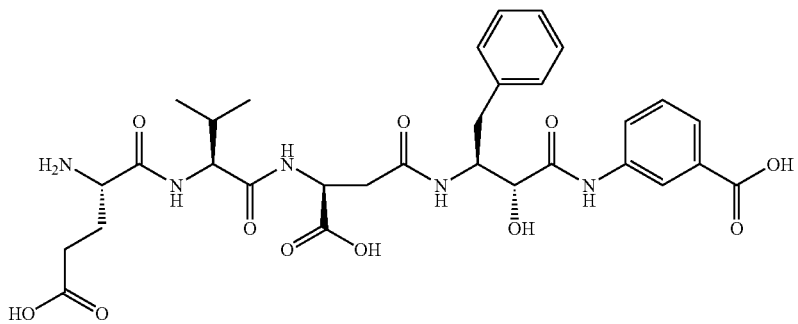

The above compound was prepared in the same manner as in Example 55.
Yield 6.4 mg (47%), TOF-MS: 658.66

Example 192

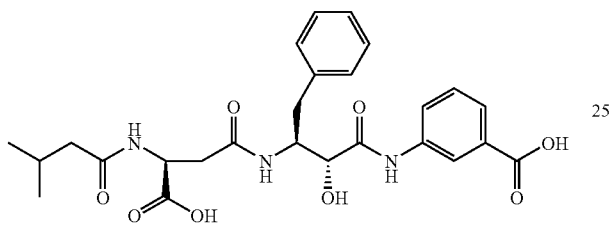

The above compound was prepared in the same manner as in Example 55.
Yield 7.1 mg (32%), TOF-MS: 514.44

---

The invention claimed is:

1. A compound represented by the general formula (1):

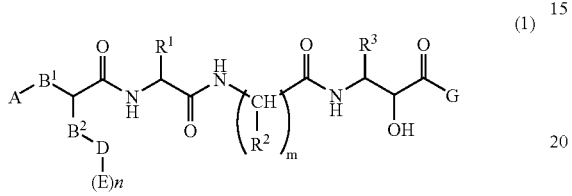

(1)

wherein A is amino group, or amino group protected with a protecting group which can be degraded in a living body, $B^1$ and $B^2$ are each a single bond or alkylene of 1 to 3 carbon atoms optionally substituted with $R^4$, in which $R^4$ is halogen atom; alkyl of 1 to 6 carbon atoms; alkenyl of 2 to 6 carbon atoms; alkynyl of 2 to 6 carbon atoms; cycloalkyl of 3 to 7 carbon atoms; optionally substituted heterocycle; optionally substituted aralkyl; or optionally substituted aryl, and the substituent thereof is alkyl of 1 to 6 carbon atoms, alkenyl of 2 to 6 carbon atoms, alkynyl of 2 to 6 carbon atoms, cycloalkyl of 3 to 7 carbon atoms, or aryl, D is a single bond, —NHCO— or NHCO—$R^5$—, in which $R^5$ is alkylene of 1 to 6 carbon atoms; alkenylene of 2 to 6 carbon atoms; alkynylene of 2 to 6 carbon atoms; cycloalkylene of 3 to 7 carbon atoms; optionally substituted heterocycle; optionally substituted aralkylene; or optionally substituted arylene, and the substituent thereof is halogen atom, alkyl of 1 to 6 carbon atoms, alkenyl of 2 to 6 carbon atoms, alkynyl of 2 to 6 carbon atoms, cycloalkyl of 3 to 7 carbon atoms, or aryl, E is —COOH, a group equivalent to COOH, hydrogen atom, hydroxy group, amino group, halogen atom, or —COOCH$_3$, n is an integer of 1 to 3, m is an integer of 1 to 3, G is hydroxy group, amino acid residue, a peptide constructed of 2 to 4 amino acids, or a group represented by the formula

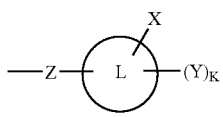

in which Z is —NH—, -Asp-Ala-NH—, -Asp-Ala-, —NH-CZ$^1$(Z$^2$)-, -Asp-NH—, -Asp-NH-CZ$^1$(Z$^2$)-, or —NH-CZ$^1$(Z$^2$)-CZ$^1$(Z$^2$)-, Ring L is a 5- to 10-membered ring optionally containing a heteroatom and/or unsaturated bond, $Z^1$ and $Z^2$ are each hydrogen atom, hydroxy group, amino group, cyano group, nitro group, alkyl of 1 to 6 carbon atoms, or halogen atom, X is hydrogen atom, —COOH, a group equivalent to COOH, —CONHR$^6$, —OCH$_2$COOR$^6$, —OCH$_2$CONHR$^6$, hydroxy group, —PO$_4$H, —SO$_3$H, -CZ$^1$(Z$^2$)-X' or a group represented by the formula:

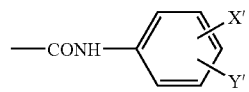

in which X' is hydrogen atom, —COOH, a group equivalent to COOH, —CONHR$^6$, —OCH$_2$COOR$^6$, —OCH$_2$CONHR$^6$, hydroxy group, —PO$_4$H, or —SO$_3$H, Y and Y' are each hydrogen atom, —COOH, a group equivalent to COOH, —CONHR$^6$, —OR$^6$, —PO$_4$H, —SO$_3$H, halogen atom, or methyl, in which $R^6$ is an alkyl of 1 to 4 carbon atoms optionally substituted with halogen atom, or hydrogen atom, and k is an integer of 1 to 4, and $R^1$, $R^2$ and $R^3$ are each —COOH, a group equivalent to COOH, alkyl of 1 to 6 carbon atoms, alkenyl of 2 to 6 carbon atoms, alkynyl of 2 to 6 carbon atoms, cycloalkyl of 3 to 7 carbon atoms, or alkyl of 1 to 6 carbon atoms substituted with any of phenyl, phenylthio, alkylthio of 1 to 6 carbon atoms, —COOH or heterocycle, provided that the phenyl, phenylthio and heterocycle may be substituted with an alkyl of 1 to 6 carbon atoms, hydroxy group, nitro, a halogen atom, —SO$_3$H or —PO$_4$H or a pharmaceutically acceptable salt thereof, or a prodrug thereof.

2. The compound of claim 1, wherein in the general formula (1), $B^1$ and $B^2$ are each a single bond, or alkylene of 1 to 3 carbon atoms optionally substituted with $R^4$, in which $R^4$ is halogen atom; alkyl of 1 to 6 carbon atoms; alkenyl of 2 to 6 carbon atoms; alkynyl of 2 to 6 carbon atoms; cycloalkyl of 3 to 7 carbon atoms; optionally substituted heterocycle; optionally substituted aralkyl; or optionally substituted aryl, and the substituent thereof is alkyl of 1 to 6 carbon atoms, alkenyl of 2 to 6 carbon atoms, alkynyl of 2 to 6 carbon atoms, cycloalkyl of 3 to 7 carbon atoms, or aryl, D is a single bond, —NHCO— or —NHCO—$R^5$—, in which $R^5$ is alkylene of 1 to 6 carbon atoms; alkenylene of 2 to 6 carbon atoms; alkynylene of 2 to 6 carbon atoms; cycloalkylene of 3 to 7 carbon atoms; optionally substituted heterocycle; optionally substituted aralkylene; or optionally substituted arylene, and the substituent thereof is halogen atom, alkyl of 1 to 6 carbon atoms, alkenyl of 2 to 6 carbon atoms, alkynyl of 2 to 6 carbon atoms, cycloalkyl of 3 to 7 carbon atoms, or aryl, E is —COOH or a group equivalent to COOH, hydrogen atom, hydroxy group, amino group, halogen atom, or —COOCH$_3$, n is an integer of 1 to 3, m is 1, G is hydroxy group, or a group represented by the formula:

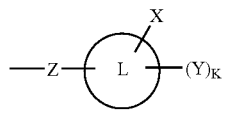

in which Z is —NH—, -Asp-Ala-NH—, -Asp-Ala-, —NH-CZ$^1$(Z$^2$)-, -Asp-NH—, -Asp-NH-CZ$^1$(Z$^2$)-, or —NH-CZ$^1$(Z$^2$)-CZ$^1$(Z$^2$)-, Ring L is a 5- to 10-membered ring optionally containing a heteroatom and/or unsaturated bond, Z$^1$ and Z$^2$ are each hydrogen atom, hydroxy group, amino group, cyano group, nitro group, alkyl of 1 to 6 carbon atoms, or halogen atom, X is hydrogen atom, —COOH, a group equivalent to COOH, —CONHR$^6$, —OCH$_2$COOR$^6$, —OCH$_2$CONHR$^6$, hydroxy group, —PO$_4$H, —SO$_3$H, -CZ$^1$(Z$^2$)-X' or a group represented by the formula:

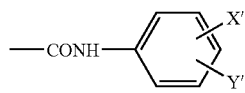

where X' is hydrogen atom, —COOH, a group equivalent to COOH, —CONHR$^6$, —OCH$_2$COOR$^6$, —OCH$_2$CONHR$^6$, hydroxy group, —PO$_4$H, or —SO$_3$H, Y and Y' are each hydrogen atom, a group equivalent to COOH, —CONHR$^6$, —OR$^6$, —PO$_4$H, —SO$_3$H, halogen atom, or methyl, in which R$^6$ is alkyl of 1 to 4 carbon atoms optionally substituted with halogen atom, or hydrogen atom, k is an integer of 1 to 4, and R$^1$, R$^2$ and R$^3$ are each alkyl of 1 to 6 carbon atoms, alkenyl of 2 to 6 carbon atoms, alkynyl of 2 to 6 carbon atoms, cycloalkyl of 3 to 7 carbon atoms, or alkyl of 1 to 6 carbon atoms substituted with any of phenyl, phenylthio, alkylthio of 1 to 6 carbon atoms, or heterocycle, provided that the phenyl, phenylthio and heterocycle may be substituted with alkyl of 1 to 6 carbon atoms, hydroxy group, nitro, halogen atom, —SO$_3$H or —PO$_4$H, or a pharmaceutically acceptable salt thereof, or a prodrug thereof.

3. The compound of claim 1, wherein in the general formula (1),

B$^1$ is a single bond or methylene,

B$^2$ is a single bond or alkylene of 1 to 3 carbon atoms,

D is a single bond, —NHCO—, a group represented by the formula:

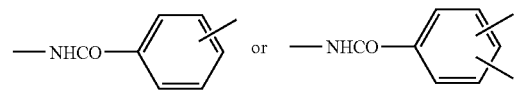

in which the benzene ring may be substituted with halogen atom, amino group, alkyl of 1 to 6 carbon atoms, alkenyl of 2 to 6 carbon atoms, alkynyl of 2 to 6 carbon atoms, cycloalkyl of 3 to 7 carbon atoms, or aryl, a group represented by the following formula:

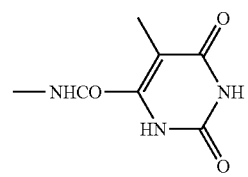

a group represented by the following formula:

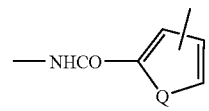

in which Q is oxygen atom or NH,

E is hydrogen atom, hydroxy group, amino group, halogen atom, —COOH, —COOCH$_3$ or tetrazole ring, n is an integer of 1 or 2, m is 1, R$^1$ is alkyl of 1 to 6 carbon atoms, alkenyl of 2 to 6 carbon atoms, alkynyl of 2 to 6 carbon atoms, cycloalkyl of 3 to 7 carbon atoms, or aryl, R$^2$ is alkyl of 1 to 6 carbon atoms, phenyl, naphthyl, isobutyl, 2-carbamoylethyl, 2-methylthioethyl, methylthiomethyl, 2-ethylthioethyl, ethylthiomethyl, naphthylmethyl, phenethyl, 4-thiazolylmethyl, 4-imidazolylmethyl, 3-tetrahydrofuranyl, 3-indolylmethyl, cyclohexylmethyl, or benzyl in which the benzene ring may be substituted with halogen atom, hydroxy group, or alkyloxy group of 1 to 6 carbon atoms, and G is any one of the group represented by the following formulas:

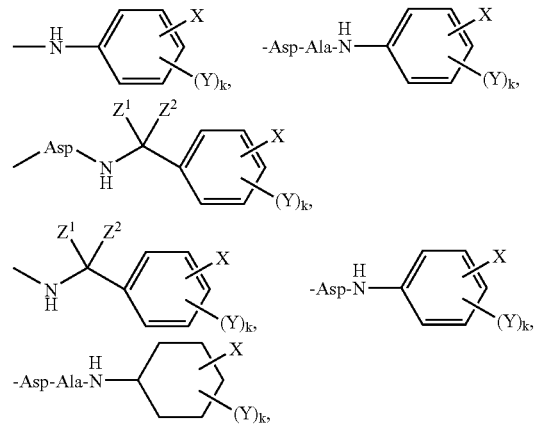

-continued

[chemical structures]

in which X and X' are each hydrogen atom, —COOH, —CONHR$^6$, —OCH$_2$COOR$^6$, —OCH$_2$CONHR$^6$, hydroxy group, —PO$_4$H, —SO$_3$H or tetrazole ring, Y and Y' are each hydrogen atom, —COOH, —CONHR$^6$, —OR$^6$, —PO$_4$H, —SO$_3$H, halogen atom, methyl or tetrazole ring, R$^6$ is alkyl of 1 to 2 carbon atoms optionally substituted with halogen atom, or hydrogen atom, k is an integer of 1 or 2, and Z$^1$ and Z$^2$ are each hydrogen, hydroxy group, amino group, cyano group, nitro group, alkyl of 1 to 6 carbon atoms, or halogen atom, or a pharmaceutically acceptable salt thereof, or a prodrug thereof.

4. The compound of claim 1, wherein in the general formula (1),

B$^1$ is a single bond,

B$^2$ is alkylene of 1 to 2 carbon atoms,

D is a single bond, —NHCO—, or a group represented by the following formula:

[chemical structures]

E is hydrogen atom, hydroxy group, halogen atom, —COOH or tetrazole ring, n is an integer of 1 or 2, m is 1, R$^1$ is isopropyl, R$^2$ is isobutyl or cyclohexylmethyl, R$^3$ is benzyl, isobutyl, phenylthiomethyl or cyclohexylmethyl, and G is any one of the group represented by the following formulas:

[chemical structures]

in which X and X' are each —COOH, —CONH$_2$, hydroxy group, —OCH$_2$COOH or tetrazole ring, Y and Y' are each hydrogen atom, COOH, CONH$_2$, halogen atom, methyl or tetrazole ring, k is an integer of 1 or 2, and Z$^1$ and Z$^2$ are each hydrogen atom, or a pharmaceutically acceptable salt thereof, or a prodrug thereof.

5. The compound of claim 1, wherein in the general formula (1), a partial structure other than G is a group represented by the formula:

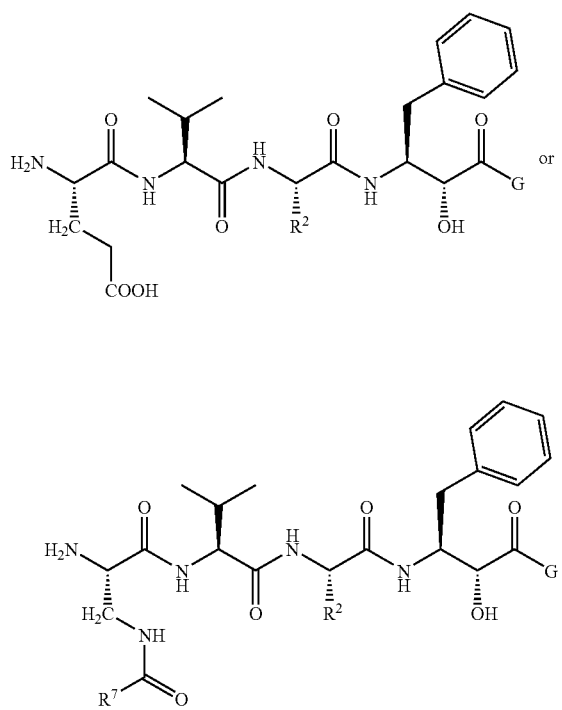

R² is isobutyl or cyclohexylmethyl,
R⁷ is a group represented by the following formula:

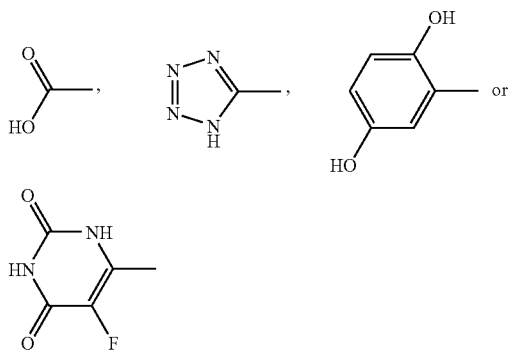

and
G is a group represented by the following formula:

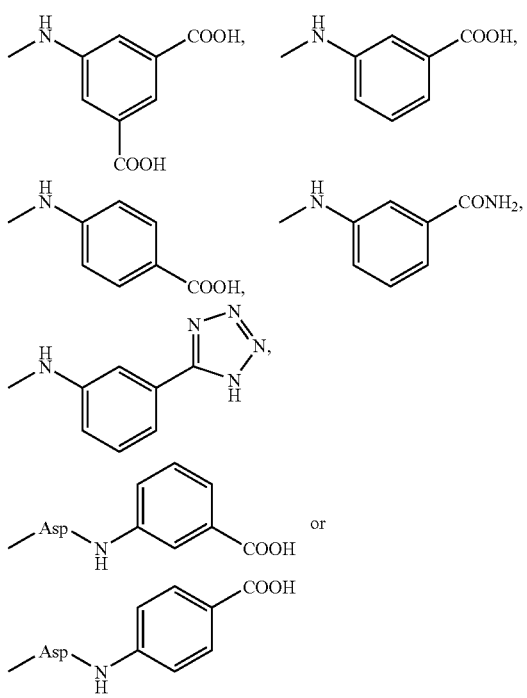

or a pharmaceutically acceptable salt thereof, or a prodrug thereof.

6. The compound of claim 1, which has a molecular weight of 1100 or lower.

7. A pharmaceutical composition comprising the compound of claim 1 as an active ingredient and a pharmaceutically acceptable carrier.

8. An agent for treating Alzheimer's disease, comprising the compound of claim 1 as an active ingredient.

9. An agent for promoting secretion of sAPPα, comprising the compound of claim 1 as an active ingredient.

10. A method for treating Alheimer's disease, which comprises administering an effective amount of the compound of claim 1 to a mammal in need thereof.

* * * * *